United States Patent
Neidle et al.

(10) Patent No.: US 7,312,082 B2
(45) Date of Patent: Dec. 25, 2007

(54) CRYSTAL STRUCTURE OF G-QUADRUPLEX CONTAINING A POTASSIUM ION

(75) Inventors: Stephen Neidle, London (GB); Gary N. Parkinson, London (GB)

(73) Assignee: Cancer Research Technology Limited, London (GB)

( * ) Notice: Subject to any disclaimer, the term of this patent is extended or adjusted under 35 U.S.C. 154(b) by 507 days.

(21) Appl. No.: 10/405,085

(22) Filed: Apr. 2, 2003

(65) Prior Publication Data

US 2004/0018483 A1    Jan. 29, 2004

(30) Foreign Application Priority Data

Apr. 2, 2002   (GB) ................................. 0207623.0

(51) Int. Cl.
    G01N 31/00    (2006.01)
    A01N 43/42    (2006.01)
    C07H 21/04    (2006.01)
(52) U.S. Cl. .................... 436/4; 514/297; 536/23.5
(58) Field of Classification Search ..................... None
    See application file for complete search history.

(56) References Cited

U.S. PATENT DOCUMENTS

| | | | |
|---|---|---|---|
| 7,160,896 B2 | 1/2007 | Neidle et al. | |
| 2004/0005686 A1* | 1/2004 | Kurumbail et al. | 435/194 |

FOREIGN PATENT DOCUMENTS

WO    WO02/08193    1/2002

OTHER PUBLICATIONS

"Encyclopedia of Molecular Biology," Creighton, T., John Wiley and Sons, Inc. New York, 1999, p. 586.*
Haider et al. (2002) J. Mol. Biol. 320:189-200.*
"Introduction to Protein Structure Second Edition", Branden and Tooze, Garland Publishing Inc., New York, 1999, p. 375.*
Kang et al. (1992) Nature 356:126-131.*
Hackett, J. A., Feldser, D. M. & Greider, C. W. Telomere dysfunction increases mutation rate and genomic instability. Cell 106, 275-286 (2001).
Smith, F. W. & Feigon, J. Quadruplex structure of oxytricha telomeric DNA oligonucleotides. Nature 356, 164-168 (1992).
Wang, Y. & Patel, D. J. Guanine residues in d($T_2AG_3$) and d($T_2G_4$) form parallel-stranded potassium cation stabilized G-quadruplexes with anti glycosidic torsion angles in solution. Biochemistry 31, 8112-8119 (1992).
Horvath, M. P. & Schultz, S. C. DNA G-quartets in a 1.86 Å resolution structure of an Oxytricha nova telomeric protein-DNA complex. J. Mol. Biol. 310, 367-377 (2001).
Dubrana, K., Perrod, S. & Gasser, S. M. Turning telomeres off and on. Curr. Opin. Cell Biol. 13, 281-289 (2001).
Wang, Y. & Patel, D. J. Solution structure of the human telomeric repeat d[$AG_3(T_2AG_3)_3$] G-tetraplex. Structure 1, 263-282 (1993).
Cimino-Reale, G. et al. The length of telomeric G-rich strand 3'-overhang measured by oligonucleotide ligation assay. Nucleic Acids Res. 29, E35 (2001).
Simonsson, T. G-quadruplex DNA structures—variations on a theme. Biol. Chem. 382, 621-628 (2001).
Phillips, K., Dauter, Z., Murchie, A. I., Lilley, D. M. & Luisi, B. The crystal structure of a parallel-stranded guanine tetraplex at 0.95 Å resolution. J. Mol. Biol. 273, 171-82 (1997).
Mergny, J.-L. & Hélène, C. G-quadruplex DNA: a target for drug design. Nature Genetics 4, 1366-1367 (1998).
Bearss, D. J., Hurley, L. H. & Von Hoff, D. D. Telomere maintenance mechanisms as a target for drug development. Oncogene 19, 6632-6641 (2000).
Gowan, S. M., Heald, R., Stevens, M. F. & Kelland, L. R. Potent inhibition of telomerase by small-molecule pentacyclic acridines capable of interacting with G-quadruplexes. Mol. Pharmacol. 60, 981-988 (2001).
Read, M. A. et al. Structure-based design of selective and potent G quadruplex-mediated telomerase inhibitors. Proc. Natl. Acad. Sci. USA 98, 4844-4849 (2001).
Sun, H., Yabuki, A. & Maizels, N. A human nuclease specific for G4 DNA. Proc. Natl. Acad. Sci. USA 98, 12444-12449 (2001).
Li, J-L. et al. Inhibition of the Bloom's and Werner's Syndrome Helicases by G-Quadruplex Interacting Ligands. Biochemistry 40, 15194-15202 (2001).
Smith, F. W., Schultze, P. & Feigon, J. Solution structures of unimolecular quadruplexes formed by oligonucleotides containing Oxytricha telomere repeats. Structure 3, 997-1008 (1995).
Balagurumoorthy, P. B. & Brahmachari, S. K. Structure and stability of human telomeric sequence. J. Biol. Chem. 269, 21858-21869 (1994).
Wang, Y. & Patel, D. J. Solution structure of the tetrahymena telomeric repeat d($T_2G_4$)$_4$. Structure 2, 1141-1156 (1994).
Read, M. A. et al. Molecular modeling studies on G-quadruplex complexes of telomerase inhibitors: Structure-activity relationships. J. Med. Chem. 42, 4538-4546 (1999).
Harrison, R. J., Gowan, S. M., Kelland, L. R. & Neidle, S. Human telomerase inhibition by substituted acridine derivatives. Bioorg. Med. Chem. Lett. 9, 2463-2468 (1999).
Han, H., Langley, D. R., Rangan, A. & Hurley, L. H. Selective interactions of cationic porphyrins with G-quadruplex structures. J. Amer. Chem. Soc. 123, 8902-8913 (2001).
Mergny, J. L. et al. Telomerase inhibitors based on quadruplex ligands selected by a fluorescence assay. Proc. Natl. Acad. Sci. USA 98, 3062-3067 (2001).
Koeppel, F. et al. Ethidium derivatives bind to G-quartets, inhibit telomerase and act as fluorescent probes for quadruplexes. Nucleic Acids Res. 29, 1087-1096 (2001).

(Continued)

Primary Examiner—David J. Steadman
(74) Attorney, Agent, or Firm—Nixon & Vanderhye P.C.

(57) ABSTRACT

The present invention relates to a crystal structure of G-quadruplexes and its use. The invention provides a crystal of an intramolecular G-quadruplex structure having a hexagonal space group P6, and unit cell dimensions a=b=56.7 and c=42.1; α=β=90°, γ=120° and a crystal of G-quadruplex having the three dimensional atomic coordinates of Table 1 or Table 2. These structures may be used in a computer-based method for the analysis of the interaction of a molecular structure with a G-quadruplex.

2 Claims, 7 Drawing Sheets

OTHER PUBLICATIONS

Fedoroff, O. Y., et al., NMR-Based model of a telomerase-inhibiting compound bound to G-quadruplex DNA. *Biochemistry* 37, 12367-12374 (1998).

Read, M. A. & Neidle, S. Structural characterization of a guanine-quadruplex ligand complex. *Biochemistry* 39, 13422-13432 (2000).

Otwinowski, Z. M. & Manor, W. Processing of X-ray diffraction data collected in oscillation mode. *Methods Enzymol.* 276, 307-326 (1997).

Brünger, A. T. et al. Crystallography & NMR system: A new software suite for macromolecular structure determination. *Acta. Crystallogr. D* 54, 905-921 (1998).

Sheldrick, G. M. & Schneider, T. R. SHELX-97: high-resolution refinement. *Methods Enzymol.* 276, 319-343 (1997).

Cambilleau, C. & Horjales, E. *J. Mol. Graphics* 5, 175-177 (1987).

Gowan et al (Molecular Pharmacology, vol. 61, No. 5 (2002), pp. 1154-1162.

* cited by examiner

External TTA loop

External TTA loop

Added TTA loop 10.3 Å rise

33°

SEQUENCE LISTING

<160> NUMBER OF SEQ ID NOS: 3

<210> SEQ ID NO 1
<211> LENGTH: 22
<212> TYPE: DNA
<213> ORGANISM: Artificial sequence
<220> FEATURE:
<223> OTHER INFORMATION: G-quadruplex-forming sequence

<400> SEQUENCE: 1
agggttaggg ttagggttag gg                                    22

<210> SEQ ID NO 2
<211> LENGTH: 12
<212> TYPE: DNA
<213> ORGANISM: Artificial sequence
<220> FEATURE:
<223> OTHER INFORMATION: G-quadruplex-forming sequence
<220> FEATURE:
<221> NAME/KEY: misc_feature
<222> LOCATION: (1)..(1)
<223> OTHER INFORMATION: n is t or 5-bromouracil
<220> FEATURE:
<221> NAME/KEY: misc_feature
<222> LOCATION: (6)..(6)
<223> OTHER INFORMATION: n is t or 5-bromouracil

<400> SEQUENCE: 2
nagggntagg gt                                               12

<210> SEQ ID NO 3
<211> LENGTH: 140
<212> TYPE: DNA
<213> ORGANISM: Artificial sequence
<220> FEATURE:
<223> OTHER INFORMATION: G-quadruplex-forming sequence
<220> FEATURE:
<221> NAME/KEY: misc_feature
<222> LOCATION: (1)..(10)
<223> OTHER INFORMATION: n is a base of any type
<220> FEATURE:
<221> NAME/KEY: misc_feature
<222> LOCATION: (1)..(10)
<223> OTHER INFORMATION: Any one or all nucleotides 1 - 10 may either be
    present or absent
<220> FEATURE:
<221> NAME/KEY: misc_feature
<222> LOCATION: (131)..(140)
<223> OTHER INFORMATION: n is a base of any type
<220> FEATURE:
<221> NAME/KEY: misc_feature
<222> LOCATION: (131)..(140)
<223> OTHER INFORMATION: Any one or all nucleotides 131 - 140 may either
    be present or absent
<220> FEATURE:
<221> NAME/KEY: misc_feature
<222> LOCATION: (11)..(130)
<223> OTHER INFORMATION: Any 17 repeats of sequence ttaggg may be
    absent; represents 3 - 20 repeats of the sequence ttaggg

<400> SEQUENCE: 3
nnnnnnnnnn ttagggttag ggttagggtt agggttaggg ttagggttag ggttagggtt    60
agggttaggg ttagggttag ggttagggtt agggttaggg ttagggttag ggttagggtt   120
agggttaggg nnnnnnnnnn                                              140

CRYSTAL STRUCTURE OF G-QUADRUPLEX CONTAINING A POTASSIUM ION

The present invention relates to a crystal structure of G-quadruplexes and its use.

Telomeric ends of chromosomes, comprising specialised non-coding guanine-rich DNA repeat sequences, play a fundamental role in protecting the cell from recombination and degradation[1]. The disruption of telomere maintenance leads to eventual cell death, which is beginning to be exploited for therapeutic intervention in cancer. It is well-established that telomeric DNA can fold into higher-order four-stranded (quadruplex) structures[2-4], and that their formation is one of several regulated states that protect telomere ends, thus ensuring effective maintenance[5].

Telomeric DNA of vertebrates consists of tandem repeats of the sequence d(TTAGGG). It plays a critical role in maintaining chromosome integrity, and destabilisation of telomere maintenance leads to cell crisis. In human somatic cells telomeric DNA is typically 5-8 kb in length, with a single-stranded 3'-overhang of 100-200 bases[7]. These G-rich single-stranded DNA sequences can fold up into four-stranded structures, termed G-quadruplexes[3,8]. Biophysical and structural methods have shown that the central units of G-quadruplexes are hydrogen-bonded arrays of guanine bases, G-quartets. Typically, several G-quartets are held together by $\pi$-$\pi$ stacking interactions. Intermolecular quadruplexes are formed by two or four separate strands associating together, as in the d(TGGGGT) quadruplex[9]. Intramolecular quadruplexes are formed by the folding of several consecutive repeats, such as the four repeats of human telomeric DNA in d[AGGG(TTAGGG)$_3$] (SEQ ID NO:1). The length of the single-stranded 3'-terminal telomeric overhang is maintained constant in human somatic cells, even though overall telomere length is shortened by 50-200 bases per round of replication. This single-stranded sequence, which can potentially fold into four to eight four-repeat quadruplexes, is far longer and more stable than in many vertebrates or other organisms. The role of quadruplexes in vivo has been highlighted with the recent development of therapeutic strategies designed to stabilise telomeric ends as G-quadruplex structures using specific small molecules, which can destabilise telomere maintenance in tumour cells[10-13]. The characterisation of a human nuclease with G-quadruplex specificity has provided support for the hypothesis that these structures may be involved as intermediates in recombination at G-rich sequences[14]. This is consistent with the finding that the same small-molecule ligands also inhibit the unwinding of G-quadruplexes by helicases that are involved in recombination[15].

DISCLOSURE OF THE INVENTION

We report here the first crystal structures of both intra- and intermolecular quadruplexes formed from 12-nucleotide and 22-nucleotide human telomere repeat sequences. These reveal a remarkable and completely unexpected folding topology and overall structural type. Both quadruplexes were expected to consist of four strands alternating between parallel and anti-parallel orientations, with the TTA loops connecting G-quartets taking the shortest paths between strands (FIG. 1c). Such arrangements were suggested from structural studies on quadruplexes[16] from *Oxytricha nova*, as well as by an NMR analysis of a sodium-containing human four-repeat sequence[6]. Instead we find that both the dimeric (12-mer) intermolecular and the 22-mer intramolecular quadruplex each have all four strands in a parallel arrangement. This strand arrangement results in a topology common to both structures in which the TTA loops are necessarily required to be extended out from the sides of the stacks of three consecutive G-quartets (FIG. 1a, b). So under the crystallizing conditions that are analogous to the ionic environment in a cell, human telomeres fold in a manner that is fundamentally distinct from those of lower organisms. Earlier CD studies on intramolecular human telomeric quadruplex sequences have suggested[17] that the antiparallel fold is solely a consequence of Na$^+$ ions, whereas the more strongly bound K$^+$ ions induce a transition to a parallel arrangement, although this was not defined in structural terms.

In general aspects, the present invention is concerned with the provision of a structure of a G-quadruplex and its use in modeling the interaction of molecular structures, e.g. potential pharmaceutical compounds, with this structure.

These and other aspects and embodiments of the present invention are discussed below.

The above aspects of the invention, both singly and in combination, all contribute to features of the invention which are advantageous.

BRIEF DESCRIPTION OF THE TABLES

Figure 1A:
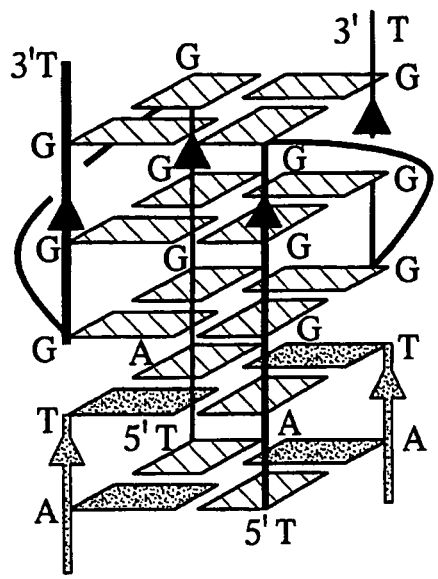
FIG. 1 Schematic showing human telomeric quadruplex folding topologies. a and b, Intramolecular and dimeric intermolecular G-quadruplexes, all with anti glycosidic torsion angles and extended external loops abutting the sides of the G-quadruplex crystallized with K$^+$. c, Fold from the NMR intramolecular G-quadruplex solution structure[6] in Na$^+$ only, with lateral and diagonal loops of sequence d(AG$_3$(T$_2$AG$_3$)$_3$) (SEQ ID NO:1). White boxes denote syn guanines.
Figure 1B:
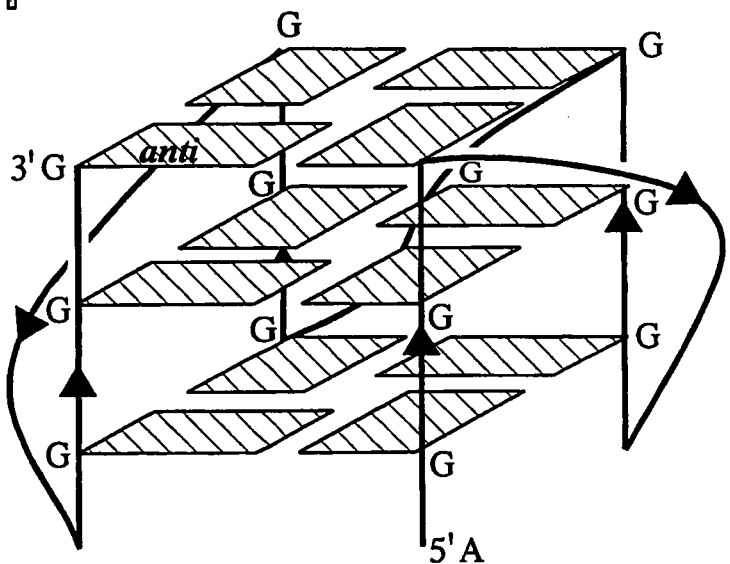
Figure 1C:
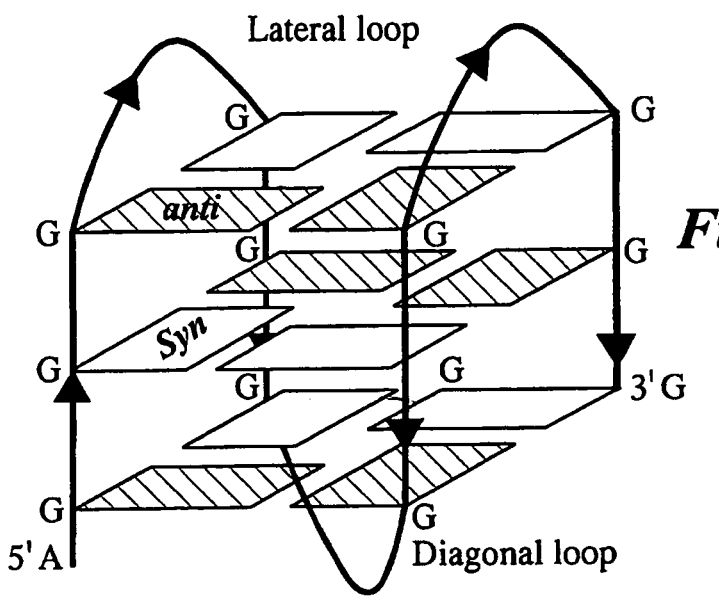

Table 1 sets out the coordinates of the intramolecular G-quadruplex.

Table 2 sets out the coordinates of the intermolecular G-quadruplex.

Table 3 provides a summary of the refinement statistics for the generation of Tables 1 and 2.

DETAILED DESCRIPTION OF THE INVENTION

A. Crystals.

In a first aspect, the invention provides a crystal of an intramolecular G-quadruplex structure having a hexagonal space group P6, and unit cell dimensions a=b=56.7 and c=42.1; $\alpha=\beta=90°$, $\gamma=120°$.

In a second aspect, the invention provides a crystal of an intermolecular G-quadruplex structure having a trigonal space group $P3_121$, and unit cell dimensions a=b=56.6 and c=40.5, $\alpha=\beta=90°$, $\gamma=120°$.

Unit cell variability of 5% may be observed in all dimensions.

Such a crystal may be obtained using the methods described in the accompanying examples.

The methodology used to provide a G-quadruplex crystal illustrated herein may be used generally to provide a G-quadruplex crystal resolvable at a resolution of at least (i.e. as good or better than) 2.5 Å, preferably at least 2.4 Å, and more preferably at least 2.1 Å.

The invention thus further provides a G-quadruplex crystal having a resolution of at least 2.5 Å, preferably at least 2.4 Å, and more preferably at least 2.1 Å.

In a further aspect, the invention provides a method for making a G-quadruplex crystal, which method comprises growing a crystal of a G-quadruplex-forming nucleic acid sequence including the nucleotide sequences of SEQ ID NO:1 or SEQ ID NO:2 by vapor diffusion using a reservoir buffer that contains a potassium salt. The growing of the crystal is by vapor diffusion and may be performed by placing an aliquot of a solution of the G-quadruplex-forming sequence on a cover slip as a hanging drop above a well containing the reservoir buffer. Preferably the buffer contains 5 to 100 mM, preferably about 50 mM potassium cacodylate, buffered at a pH range of from 6.0 to 7.0, preferably at about pH 6.5. The aliquot contains the nucleic acid solution and reservoir buffer, the buffer also preferably being 5 to 100 mM potassium cacodylate, preferably about 50 mM, buffered at a pH range of from 6.0 to 7.0, preferably at about pH 6.5.

The novel crystal structures determined here are of particular interest because they provide a detailed structure of the quartets of guanine bases which make up the G-quadruplex structures of the telomeres. Although we have obtained such quartets in the context of inter- and intra-molecular structures of the sequences of SEQ ID NO:1 and SEQ ID NO:2, it will be appreciated that our findings will enable those of skill in the art to produce similar crystals with G-quadruplex-forming sequences which differ in a non-critical manner from those of SEQ ID NO:1 and SEQ ID NO:2.

G-quadruplex-forming sequences include nucleic acid sequences comprising at least four sets of guanosine triplets linked by sequences of bases allowing the four sets of triplets to form a G-quadruplex structure. The nucleic acid sequences are preferably DNA sequences, optionally including one or more modified base (e.g. 5-bromo uracil). The nucleic acid sequences may range from 12 to 200 bases in length, preferably from 12 to 48 bases in length.

Preferred G-quadruplex-forming sequences include sequences comprising multimers of the sequence TTAGGG, e.g. a sequence of the formula X1-(TTAGGG)$_n$-X2, (SEQ ID NO:3) where n is an integer from 3 to 20, preferably from 3 to 12; X1 is a 5' terminus or a sequence of from 1 to 10 bases of any type; and X2 is a 3' terminus or a sequence of from 1 to 10 bases of any type. Preferably each of X1 and X2 are either a terminus of the nucleic acid sequence (i.e. do not represent any further bases) or are a partial repeat of the core sequence TTAGGG linked to maintain the base order in relation the core repeat (e.g. X1 is AGGG and X2 is TTA, and so forth).

Thus other crystals of the invention include crystals of a four stranded G-quadruplex structure, each strand being in a parallel conformation and each strand comprising three contiguous guanosine residues, in which an arrangement of at least one, preferably two and most preferably three G-quadruplex quartets of guanine bases associated with those selected coordinates are located in a nucleic acid framework which holds these bases in a relative spatial configuration corresponding to the spatial configuration of those bases in Table 1 or 2. By "corresponding to", it is meant within a r.m.s.d. of less than 2.0 Å, preferably less than 1.5 Å, more preferably less than 1.0 Å, and most preferably less than 0.5 Å.

B. Crystal Coordinates.

In a further aspect, the invention also provides a crystal of G-quadruplex having the three dimensional atomic coordinates of Table 1 or Table 2. An advantageous feature of the structure defined by the atomic coordinates is that it has a resolution of better than about 2.4 Å.

Another advantageous feature of the invention is that unlike previous crystal models, it is believed that the present crystal coordinates provide a much more accurate reflection of the native biological structure of the DNA in the human telomere.

Tables 1 and 2 give atomic coordinate data for G-quadruplex structures. In Tables 1 and 2 first column of the atomic coordinate data provides a unique ATOM identifier number (in the format ATOM (or HETATM) n), where n is from 1 to the end of the table) the second column denotes the element of the atom and (where applicable) its number in the nucleoside base, the third column denotes the nucleoside base (or other atom e.g. K or the O of water), the fourth nucleotide chain (chain A in the case of Table 1, chains A and B for the intermolecular structure of Table 2), the fifth the base number of the nucleic acids (metal ions are numbered sequentially, waters numbered from 1000 or 2000), the sixth, seventh and eighth columns are the X, Y, Z coordinates respectively of the atom in question, the ninth column the occupancy of the atom, the tenth the temperature factor of the atom, and last, twelfth column, the atom type again.

The coordinates of Tables 1 and 2 provide a measure of atomic location in Angstroms, to 3 decimal places. The coordinates are a relative set of positions that define a shape in three dimensions, but the skilled person would understand that an entirely different set of coordinates having a different origin and/or axes could define a similar or identical shape. Furthermore, the skilled person would understand that varying the relative atomic positions of the atoms of the structure so that the root mean square deviation of at least the guanine base atoms, preferably the entire guanosine nucleoside atoms, is less than 2.0 Å, preferably less than 1.5 Å, more preferably less than 1.0 Å, and most preferably less than 0.5 Å when superimposed on the coordinates provided in Tables 1 or 2 for the base or nucleoside atoms, will generally result in a structure which is substantially the same as the structure of Tables 1 and 2 in terms of both its structural characteristics and usefulness for structure-based analysis of G-quadruplex-interacting molecular structures.

Likewise the skilled person would understand that changing the number and/or positions of the water molecules of Table 1 or Table 2, or bromine atoms of Table 2, will not generally affect the usefulness of the structure for structure-based analysis of G-quadruplex-interacting structure. Thus for the purposes described herein as being aspects of the present invention, it is within the scope of the invention if: the Table 1 or 2 coordinates are transposed to a different origin and/or axes; the relative atomic positions of the atoms of the structure are varied so that the root mean square deviation of the guanine base, preferably the guanosine nucleosides, is less than 2.0 Å, preferably less than 1.5 Å, more preferably less than 1.0 Å, even more preferably less than 0.5 Å when superimposed on the coordinates provided in Table 1 or 2 for the residue backbone atoms; and/or the number and/or positions of water molecules and/or substrate molecules is varied (including varied to a value of 0).

Reference herein to the coordinate data of Table 1 or 2 and the like thus includes the coordinate data in which one or more individual values of the Tables are varied in this way. By "root mean square deviation" we mean the square root of the arithmetic mean of the squares of the deviations from the mean.

Thus, for example, varying the atomic positions of the atoms of the structure by up to about 0.5, preferably up to about 0.3 Å in any direction will result in a structure which is substantially the same as the structure of Tables 1 or 2 in terms of both its structural characteristics and utility e.g. for molecular structure-based analysis.

C. Structure Solution

The structure of the G-quadruplex can also be used to solve the crystal structure of other target G-quadruplexes including other crystal forms of G-quadruplex, mutants, co-complexes of G-quadruplex, where X-ray diffraction data of these target G-quadruplexes has been generated and requires interpretation in order to provide a structure.

In the case of other target G-quadruplex-forming sequences, particularly a human G-quadruplex structure of a different primary sequence, the present invention allows the structures of such targets to be obtained more readily where raw X-ray diffraction data is generated.

Thus, where X-ray crystallographic or NMR spectroscopic data is provided for a target G-quadruplex-forming sequence of unknown three-dimensional structure, the structure of G-quadruplex as defined by Tables 1 or 2 may be used to interpret that data to provide a likely structure for the other G-quadruplex by techniques which are well known in the art, e.g. phasing in the case of X-ray crystallography and assisting peak assignments in nmr spectra.

One method that may be employed for these purposes is molecular replacement. In this method, the unknown crystal structure, whether it is another crystal form of G-quadruplex a G-quadruplex mutant, or a G-quadruplex co-complex, or the crystal of a target G-quadruplex structure with nucleic acid sequence homology to any functional domain of G-quadruplex, may be determined using the G-quadruplex structure coordinates of this invention as provided herein. This method will provide an accurate structural form for the unknown crystal more quickly and efficiently than attempting to determine such information ab initio.

Examples of computer programs known in the art for performing molecular replacement are CNX (Brunger A. T.; Adams P. D.; Rice L. M., Current Opinion in Structural Biology, Volume 8, Issue 5, October 1998, Pages 606-611 (also commercially available from Accelerys San Diego, Calif.) or AMORE (Navaza, J. (1994). AMoRe: an automated package for molecular replacement. Acta Cryst. A50, 157-163).

D. Computer Systems.

In another aspect, the present invention provides systems, particularly a computer system, the systems containing any of (a) atomic coordinate data according to Tables 1 or 2, said data defining the three-dimensional structure of a G-quadruplex structure or at least selected coordinates thereof; (b) structure factor data (where a structure factor comprises the amplitude and phase of the diffracted wave) for the G-quadruplex, said structure factor data being derivable from the atomic coordinate data of Table 1 or Table 2; (c) atomic coordinate data of a target G-quadruplex structure generated by homology modeling of the target based on the data of Table 1 or Table 2; (d) atomic coordinate data of a target G-quadruplex structure generated by interpreting X-ray crystallographic data or nmr data by reference to the data of Table 1 or Table 2; or (e) structure factor data derivable from the atomic coordinate data of (c) or (d).

As used herein, "selected coordinates" of the G-quadruplex structures of Tables 1 and 2 refers to any combination of fewer than all of the coordinates set out in those Tables.

At a minimum, the selected coordinates comprise the coordinates of at least 5, preferably at least 10, more preferably at least 50 and even more preferably at least 100 selected atoms of the G-quadruplex structure.

Particularly preferred groups of selected coordinates include:
 the coordinates of the guanine bases of a single G-quartet;
 the coordinates of the guanine bases of two or three of such quartets;
 the coordinates of the guanonsine nucleosides of one, two or three G-quartets; and
 the coordinates of the nucleosides of an intramolecular G-guadruplex structure comprising the 12 guanonsine nucleosides and the three linking loops of nucleosides joining the four sets of guanosine triplets.

The above are only exemplary of selected coordinates and other groups of coordinates from the tables may be used, and other combinations of coordinates may be used, depending upon the requirements of those of skill in the art. For example, fewer than all of the coordinates of individual sugars or bases may be used where it is found or believed that the omission of some atoms has little or no effect on the particular use the selected coordinates are being put to.

The invention also provides such systems containing atomic coordinate data, or selected coordinates thereof, of target G-quadruplex structures wherein such data has been generated according to the methods of the invention described herein based on the starting data provided by Tables 1 or 2.

Such data is useful for a number of purposes, including the analysis or development of compounds which interact with G-quadruplexes, such as compounds which bind to such structures and inhibit the action of telomerase or other enzymes associated with maintaining or extending the DNA of telomeres.

In a further aspect, the present invention provides computer readable media with any of (a) atomic coordinate data according to Tables 1 or 2 recorded thereon, said data defining the three-dimensional structure of a G-quadruplex structure, or at least selected coordinates thereof; (b) structure factor data for a G-quadruplex structure recorded thereon, the structure factor data being derivable from the atomic coordinate data of Table 1 or Table 2; (c) atomic coordinate data of a target G-quadruplex structure generated by homology modeling of the target based on the data of Table 1 or Table 2; (d) atomic coordinate data of a target G-quadruplex structure generated by interpreting X-ray crystallographic data or nmr data by reference to the data of Table 1 or Table 2; or (e) structure factor data derivable from the atomic coordinate data of (c) or (d).

As used herein, "computer readable media" refers to any medium or media which can be read and accessed directly by a computer. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

By providing such computer readable media, the atomic coordinate data can be routinely accessed to model G-quadruplex or selected coordinates thereof. For example, RAS-MOL (Sayle et al., *TIBS*, Vol. 20, (1995), 374) is a publicly available computer software package which allows access and analysis of atomic coordinate data for structure determination and/or rational drug design.

On the other hand, structure factor data, which are derivable from atomic coordinate data (see e.g. Blundell et al., in *Protein Crystallography*, Academic Press, New York, London and San Francisco, (1976)), are particularly useful for calculating e.g. difference Fourier electron density maps.

As used herein, "a computer system" refers to the hardware means, software means and data storage means used to analyze the atomic coordinate data of the present invention. The minimum hardware means of the computer-based systems of the present invention comprises a central processing unit (CPU), input means, output means and data storage means. Desirably a monitor is provided to visualize structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

E. Uses of the Structures of the Invention.

The crystal structures obtained according to the present invention (including the structure of Table 1 or Table 2 as well the structures of target G-quadruplex structures obtained in accordance with the methods described herein) may be used in several ways for drug design. There are currently many approaches in the art for the design of telomerase inhibitor compounds, based on compounds which are believed to intercalate the G-quartet structure of the telomere. Such compounds include acridine-based compounds (see for example refs 12, 13 and 25), porphyrin-based compounds (see for example refs 10 and 11), and other structures (ref 11).

The G-quadruplex structures of the invention will allow a better understanding of how such compounds interact with telomeric DNA. The activity of these known compounds against telomerase can be compared in the light of their fit to the present structures of the invention, to allow an improved understanding of structure-activity relationships.

Further compounds, based upon the structures of known G-quadruplex-interacting compounds or from other classes of planar molecules can be modelled with the G-quadruplex structures of the invention, in order to facilitate rational drug design.

Thus, the determination of the three-dimensional structure of the G-quadruplex provides a basis for the design of new compounds which interact with a G-quadruplex in novel ways. For example, knowing the three-dimensional structure of the G-quadruplex, computer modeling programs may be used to design different molecules expected to interact the structure.

(i) Obtaining and Analyzing Crystal Complexes.

In one approach, the structure of a compound bound to a G-quadruplex may be determined by experiment. This will provide a starting point in the analysis of the compound bound to a G-quadruplex, thus providing those of skill in the art with a detailed insight as to how that particular compound interacts with the G-quadruplex and the mechanism by which it intercalates the DNA.

Many of the techniques and approaches to structure-based drug design described above rely at some stage on X-ray analysis to identify the binding position of a ligand in a ligand-target complex. A common way of doing this is to perform X-ray crystallography on the complex, produce a difference Fourier electron density map, and associate a particular pattern of electron density with the ligand. However, in order to produce the map (as explained e.g. by Blundell et al., mentioned above) it is necessary to know beforehand the 3D structure. Therefore, the correct determination of the G-quadruplex structure also allows difference Fourier electron density maps of G-quadruplex-compound complexes to be produced, which can greatly assist the process of rational drug design.

Accordingly, the invention provides a method for determining the structure of a compound bound to a G-quadruplex, said method comprising:

providing a crystal of G-quadruplex according to the invention;

soaking the crystal with said compounds; and determining the structure of said G-quadruplex-compound complex by employing the data of Table 1 or Table 2.

Alternatively, the G-quadruplex and compound may be co-crystallized. Thus the invention provides a method for determining the structure of a compound bound to G-quadruplex, said method comprising;

co-crystallising a G-quadruplex-forming nucleic acid sequence with a compound; and determining the structure of said G-quadruplex-compound complex by employing the data of Table 1 or Table 2.

The analysis of such structures may employ (i) X-ray crystallographic diffraction data from the complex and (ii) a three-dimensional structure of G-quadruplex, or at least selected coordinates thereof, to generate a difference Fourier electron density map of the complex, the three-dimensional structure being defined by atomic coordinate data according to Table 1 or Table 2. The difference Fourier electron density map may then be analyzed.

Therefore, such complexes can be crystallized and analyzed using X-ray diffraction methods, e.g. according to the approach described by Greer et al., *J. of Medicinal Chemistry*, Vol. 37, (1994), 1035-1054, and difference Fourier electron density maps can be calculated based on X-ray diffraction patterns of soaked or co-crystallized G-quadruplex and the solved structure of the uncomplexed G-quadruplex. These maps can then be analyzed e.g. to determine whether and where a particular compound binds to G-quadruplex and/or changes the conformation of G-quadruplex.

Electron density maps can be calculated using programs such as those from the CCP4 computing package (Collaborative Computational Project 4. The CCP4 Suite: Programs for Protein Crystallography, *Acta Crystallographica*, D50, (1994), 760-763.). For map visualization and model building programs such as "O" (Jones et al., *Acta Crystallography*, A47, (1991), 110-119) can be used.

All of the complexes referred to above may be studied using well-known X-ray diffraction techniques and may be refined against 1.5 to 3.5 Å resolution X-ray data to an R value of about 0.30 or less using computer software, such as CNX (mentioned above) X-PLOR (Yale University, ©1992, distributed by Accelerys—also see, e.g., Blundell et al; Methods in Enzymology, vol. 114 & 115, H. W. Wyckoff et al., eds., Academic Press (1985) (23)).

This information may thus be used to optimize known classes of G-quadruplex ligands, and more importantly, to design and synthesize novel classes of G-quadruplex ligands and to design drugs with ligand-binding activity to the G-quadruplex structure.

(ii) In Silico Analysis and Design

Although the invention will facilitate the determination of actual crystal structures comprising the G-quadruplex and a compound which interacts with the G-quadruplex structure, current computational techniques provide a powerful alternative to the need to generate such crystals and generate and analyze diffraction date. Accordingly, a particularly preferred aspect of the invention relates to in silico methods directed to the analysis and development of compounds which interact with G-quadruplex structures of the present invention.

Thus as a result of the determination of the G-quadruplex 3D structure, more purely computational techniques for rational drug design may also be used to design structures whose interaction with a G-quadruplex is better understood (for an overview of these techniques see e.g. Walters et al (*Drug Discovery Today*, Vol.3, No.4, (1998), 160-178). For example, automated ligand-receptor docking programs (discussed e.g. by Jones et al. in *Current Opinion in Biotechnology*, Vol.6, (1995), 652-656) which require accurate information on the atomic coordinates of target receptors may be used.

The aspects of the invention described herein which utilize the G-quadruplex structure in silico may be equally applied to both the G-quadruplex structure of Table 1 or Table 2 and the models of target G-quadruplex structures obtained by other aspects of the invention. Thus having determined a conformation of a G-quadruplex structure by the method described above, such a conformation may be used in a computer-based method of rational drug design as described herein. In addition the availability of the structure of the G-quadruplex will allow the generation of highly predictive pharmacophore models for virtual library screening or compound design.

Accordingly, the invention provides a computer-based method for the analysis of the interaction of a molecular structure with a G-quadruplex structure of the invention, which comprises:

providing the structure of a G-quadruplex of the invention;

providing a molecular structure to be fitted to said G-quadruplex structure; and fitting the molecular structure to the G-quadruplex structure.

In an alternative aspect, the method of the invention may utilize selected coordinates (as defined above) of atoms of interest of the G-quadruplex which are in the vicinity of a putative molecular structure binding region in order to model the pocket in which the structure binds. These selected coordinates may be used to define a space which is then analyzed "in silico". Thus the invention provides a computer-based method for the analysis of molecular structures which comprises:

providing selected coordinates of a G-quadruplex structure of the invention;

providing the structure of a molecular structure to be fitted to said coordinates; and fitting the structure to the selected coordinates of the G-quadruplex.

In practice, it will be desirable to model a sufficient number of atoms (i.e. selected coordinates) of the G-quadruplex as defined by the coordinates of Table 1 or Table 2 which represent a ligand-binding region.

In this aspect of the invention, the selected coordinates may comprise coordinates of some or all of these residues which form the binding pocket for the substrate for G-quadruplex.

In order to provide a 3-dimensional structure of compounds to be fitted to a G-quadruplex structure of the invention, the compound structure may be modeled in three dimensions using commercially available software for this purpose or, if its crystal structure is available, the coordinates of the structure may be used to provide a representation of the compound for fitting to a G-quadruplex structure of the invention.

By "fitting", it is meant determining by automatic, or semi-automatic means, interactions between at least one atom of a molecular structure and at least one atom of a G-quadruplex structure of the invention, and calculating the extent to which such an interaction is stable. Interactions include attraction and repulsion, brought about by charge, steric considerations and the like. Various computer-based methods for fitting are described further herein.

More specifically, the interaction of a compound with a G-quadruplex structure can be examined through the use of computer modeling using a docking program such as GRAM, DOCK, or AUTODOCK (see Walters et al., *Drug Discovery Today*, Vol.3, No.4, (1998), 160-178, and Dunbrack et al., *Folding and Design*, 2, (1997), 27-42). This procedure can include computer fitting of compounds to G-quadruplex to ascertain how well the shape and the chemical structure of the compound will bind to the G-quadruplex.

Also computer-assisted, manual examination of the active site structure of G-quadruplex may be performed. The use of programs such as GRID (Goodford, *J. Med. Chem.*, 28, (1985), 849-857)—a program that determines probable interaction sites between molecules with various functional groups and an enzyme surface—may also be used to analyze the active site to predict, for example, the types of modifications which will alter the binding affinity of a compound to a target.

Computer programs can be employed to estimate the attraction, repulsion, and steric hindrance of the two binding partners (i.e. the G-quadruplex and a compound).

If more than one G-quadruplex active site is characterized and a plurality of respective smaller compounds are designed or selected, a compound may be formed by linking the respective small compounds into a larger compound which maintains the relative positions and orientations of the respective compounds at the active sites. The larger compound may be formed as a real molecule or by computer modeling.

Detailed structural information can then be obtained about the binding of the compound to G-quadruplex, and in the light of this information adjustments can be made to the structure or functionality of the compound, e.g. to alter its interaction with G-quadruplex. The above steps may be repeated and re-repeated as necessary.

As indicated above, molecular structures which may be fitted to the G-quadruplex structure of the invention include compounds under development as potential pharmaceutical agents. The agents may be fitted in order to determine how they might alter or stabilize the structure of the G-quadruplex.

Molecular structures which may be used in the present invention will usually be compounds under development for pharmaceutical use. Generally such compounds will be organic molecules which are typically from about 100 to 2000, more preferably from about 100 to 1000 Da in molecular weight. Such compounds include peptides and derivatives thereof, and polycyclic planar compounds which charge-carrying side groups which intercalate with and hydrogen bond to the guanine quartets of the G-quadruplex structure.

(iii) Analysis and Modification of Compounds.

Where the a compound that interacts with the G-quadruplex structure is known, the invention provides a means to better determine which residues of the G-quadruplex interact with the compound, or to predict how modification of that compound may improve its activity. The invention thus provides a method which comprises:
fitting a starting compound to a G-quadruplex structure of the invention or selected coordinates thereof;
determining or predicting how said compound binds to said G-quadruplex structure; and
modifying the compound structure so as to alter the interaction between it and the G-quadruplex.

It would be understood by those of skill in the art that modification of the structure will usually occur in silicon allowing predictions to be made as to how the modified structure interacts with the G-quadruplex.

Modification will be those conventional in the art known to the skilled medicinal chemist, and will include, for example, substitutions or removal of groups containing residues which interact with the bases, sugars or phosphate groups of a G-quadruplex structure of the invention. For example, the replacements may include the addition or removal of groups in order to decrease or increase the charge of a group in a test compound, the replacement of a charge group with a group of the opposite charge, or the replacement of a hydrophobic group with a hydrophilic group or vice versa. It will be understood that these are only examples of the type of substitutions considered by medicinal chemists in the development of new pharmaceutical compounds and other modifications may be made, depending upon the nature of the starting compound and its activity.

Where a potential modified compound has been developed by fitting a starting compound to the G-quadruplex structure of the invention and predicting from this a modified compound with an altered activity, the invention further includes the step of synthesizing the modified compound and testing it in a in vivo or in vitro biological system in order to determine its activity.

The above-described processes of the invention may be iterated in that the modified compound may itself be the basis for further compound design.

(iv) Compounds of the Invention.

Where a potential modified compound has been developed by fitting a starting compound to the G-quadruplex structure of the invention and predicting from this a modified compound with an altered activity, the invention further includes the step of synthesizing the modified compound and testing it in a in vivo or in vitro biological system in order to determine its activity.

In another aspect, the invention includes a compound which is identified by the methods of the invention described above.

Following identification of such a compound, it may be manufactured and/or used in the preparation, i.e. manufacture or formulation, of a composition such as a medicament, pharmaceutical composition or drug. These may be administered to individuals.

Thus, the present invention extends in various aspects not only to a compound as provided by the invention, but also a pharmaceutical composition, medicament, drug or other composition comprising such a compound e.g. for treatment (which may include preventative treatment) of disease; a method comprising administration of such a composition to a patient, e.g. for treatment of disease; use of such an inhibitor in the manufacture of a composition for administration, e.g. for treatment of disease; and a method of making a pharmaceutical composition comprising admixing such an inhibitor with a pharmaceutically acceptable excipient, vehicle or carrier, and optionally other ingredients.

Diseases which may be treated include cancers in which uncontrolled cell growth is associated with the presence of telomerase activity or with other mechanisms of maintaining telomere length and integrity.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention.

The invention is illustrated by the following example:

EXAMPLES

Methods

Purification and Crystallization

DNA sequences d(T$^+$AGGGT$^+$TAGGGT; SEQ ID NO:2), where T$^+$ is 5-bromouracil, and d(AGGGTTAGGGT-TAGGGTTAGGG; SEQ ID NO:1), were purchased from the Oswel DNA Service (Southampton University). Before use the DNA was heated to 358 K for 5 minutes and annealed to room temperature overnight in 50 mM potassium cacodylate buffer at pH 6.5. High-resolution DNA crystals for the sequence d(T⁺AGGGT⁺TAGGGT) (SEQ ID NO:2) were grown by vapor diffusion from hanging drops at 285° K using a 50% ammonium sulphate gradient. The initial drop conditions were 500 mM $(NH_4)_2SO_4$, 50 mM NaCl, 50 mM KCl, 50 mM $Li_2SO_4$, 0.5 mM DNA and 50 mM potassium cacodylate buffered at pH 6.5. The crystals grew over several weeks as large hexagonal rods of dimensions 0.2×0.2×0.4 mm. The DNA sequence d(AGGGT-TAGGGTTAGGGTTAGGG) (SEQ ID NO:1), was purified by anion exchange chromatography (HQ/M) Poros and buffer exchanged into 50 mM potassium cacodylate at pH 6.5, 30 mM KCl. High-resolution DNA crystals of the 22 mer were grown by vapor diffusion from hanging drops at 285° K using a 75% gradient. The initial drop conditions were 300 mM KI, 15% v/v PEG 400, 1.7 mM DNA, 2 mM BRACO19 a trisubstituted acridone derivative, and 50 mM potassium cacodylate buffered at pH 6.5. The crystals grew over several weeks as large hexagonal rods of dimensions 0.1×0.1×0.4 mm.

Structure Determination and Refinement

Figure 2A:
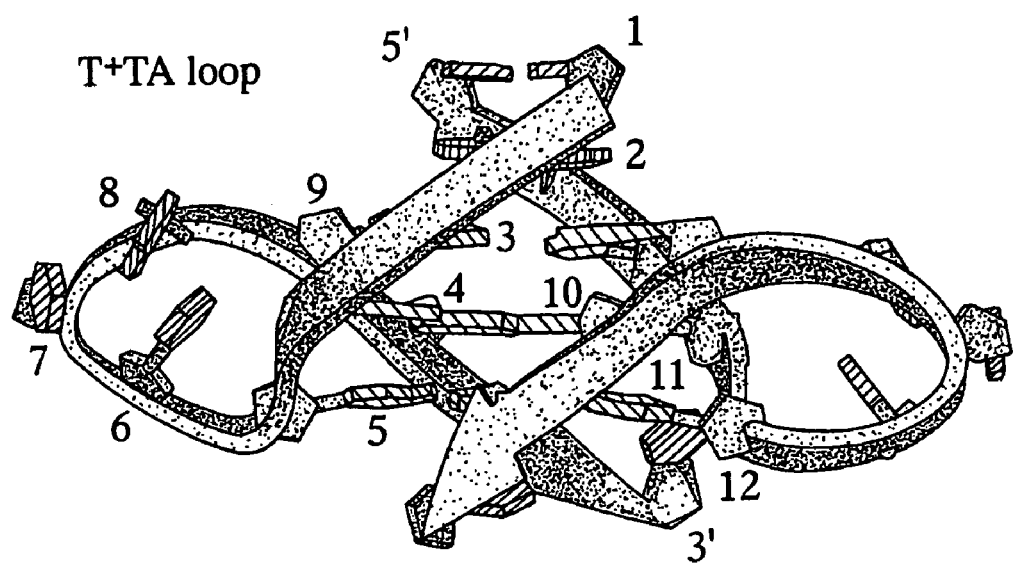
FIG. 2 The overall folding topology of the two 12-mers constituting the content of the asymmetric unit in the dimeric quadruplex. a, Side view of the quadruplex with the phosphate sugar backbone drawn as a white arrow showing 5'-3' directionality. The guanines are indicated as 3-5 and 9-11, thymines and modified uracils as 1, 6, 7, and 12, and adenines as 2 and 8. b, View from the 5' end of the quadruplex. Strands A and B are shaded light and dark respectively. c, The initial electron density map calculated with MAD solvent-flattened phases to 2.9 Å resolution, contoured at a 1.6 Å level and centered around the extended TTA loop region abutting the sides of the G-quadruplex. The final model is overlaid for clarity. d, The same region showing the final $\alpha_A$-weighted (2F$_o$-F$_c$) electron density map contoured at 1.4 $\sigma$ using 10-2.4 Å resolution data, drawn with the program TURBO[30].
Figure 2B:
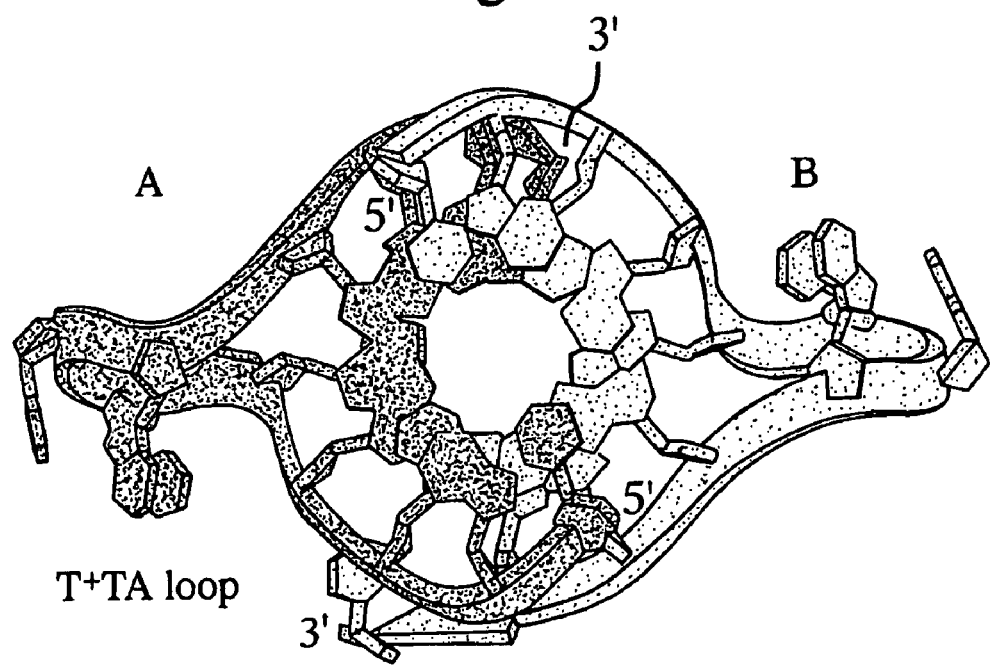
Figure 2C:
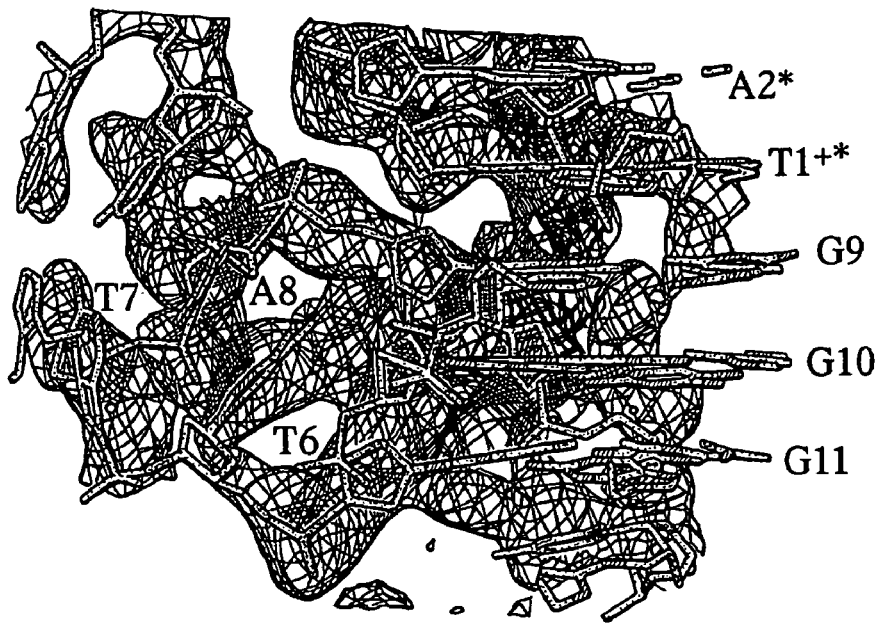
Figure 2D:
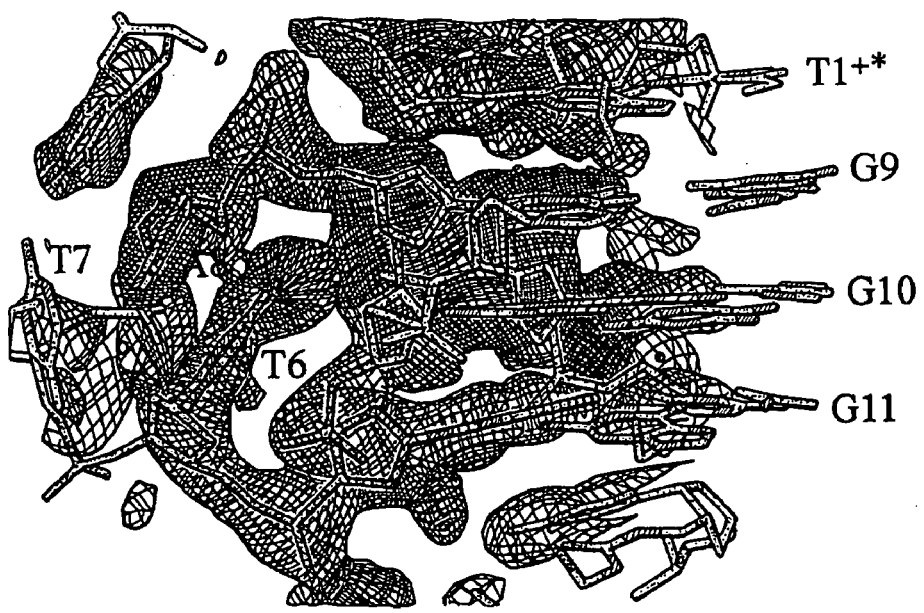

The structure of the human sequence d(T⁺AGGGT⁺TAGGGT) (SEQ ID NO:2) was determined using experimental phases obtained from a three-wavelength MAD experiment using the 5-bromo-uracil nucleotides as anomalous scatterers. Three datasets at 2.6-2.9 ∈ and at three different wavelengths, were collected using a single flash-frozen crystal at 100 K. MAD data were collected on the ESRF beamline ID14.4 at Grenoble, France. A 2.4 Å data set collected in-house was used for the high-resolution refinement. These data were collected using an RAXIS IV image plate detector, with a rotating copper anode and Osmic focusing mirrors. Data were processed and scaled with the DENZO and SCALEPACK programs programs[27]. Two of the four bromine atoms were identified from anomalous Patterson maps and used in the structure determination. Subsequent difference Fourier maps revealed one additional Br site. Positions and occupancies were refined with the CNS program[28] and the experimental phases were solvent-corrected and extended to 2.7 Å. A partial model was built into the experimental maps. Interpretable Fourier maps were obtained using 67% of the model, allowing the remaining residues in the asymmetric unit to be unambiguously located. Refinement was initially performed with CNS using standard protocols. The model was inspected manually with $α_A$-weighted $2F_o$-$F_c$ and $F_o$-$F_c$ maps, and progress in the model refinement was gauged by the decrease in the value of $R_{free}$. After further model building, refinement was then performed with the program Shelx-97[29], to 2.4 Å resolution. Only one of the two TTA loops was clearly visible in the initial solvent flattened maps or the $α_A$-weighted ($2F_o$-$F_c$) and ($F_o$-$F_c$) density maps (FIGS. 2c, d). The final nucleotides forming the second TTA loop were only included during the latter part of the refinement with 10% occupancy after the model was refined with all solvent molecules included, using data from 10-2.4 Å, to R and $R_{free}$ values of 18.5% and 26.5% respectively.

Figure 3A:
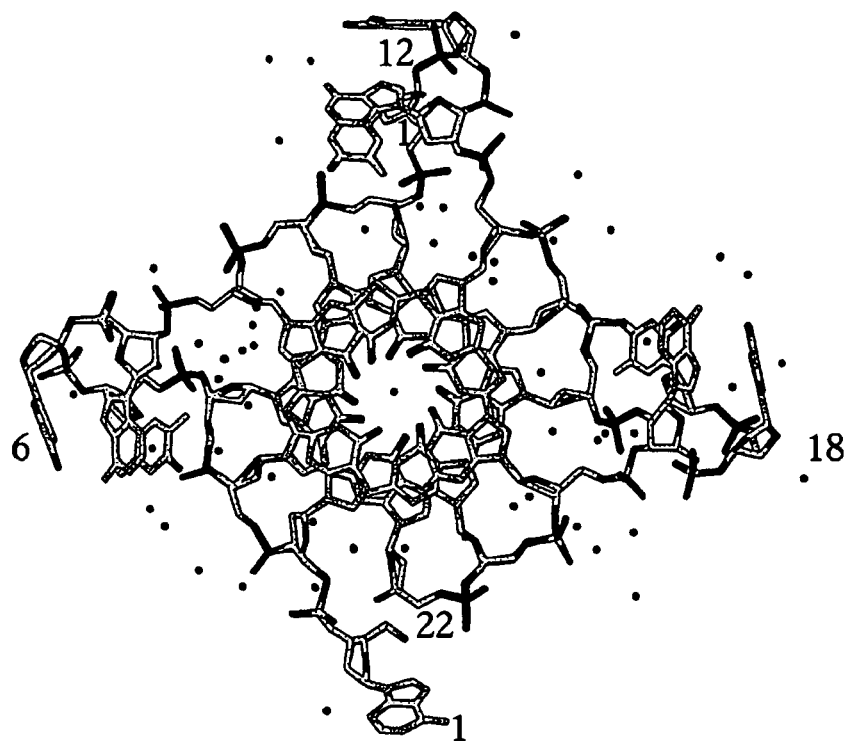
FIG. 3 Overall folding topology of the 22-mer intramolecular G-quadruplex. a, Stick representation coloured by atom type and viewed on the 3' face. The central potassium counter ion is coordinated in a bipyramidyl antiprismatic arrangement by the electronegative carbonyl groups of guanine O6. Drawn with the program TURBO[30]. b, View from the 5' end of the quadruplex looking down the helical axis with the phosphate sugar backbone drawn as an arrow showing 5' to 3' directionality, guanines arranged centrally, the thymines and adenines extending outwards. c A representative part of the structure around the extended TTA loop region abutting the sides of the G-quadruplex overlaid is a $\alpha_A$-weighted map using 10-2.1 Å data contoured at 1.8$\sigma$. d, Side view of the quadruplex highlighting its like disc shape and positioning of the 3' and 5' strand ends. e, Space filling van der Waals contoured representation, shaded by charge.
Figure 3B:
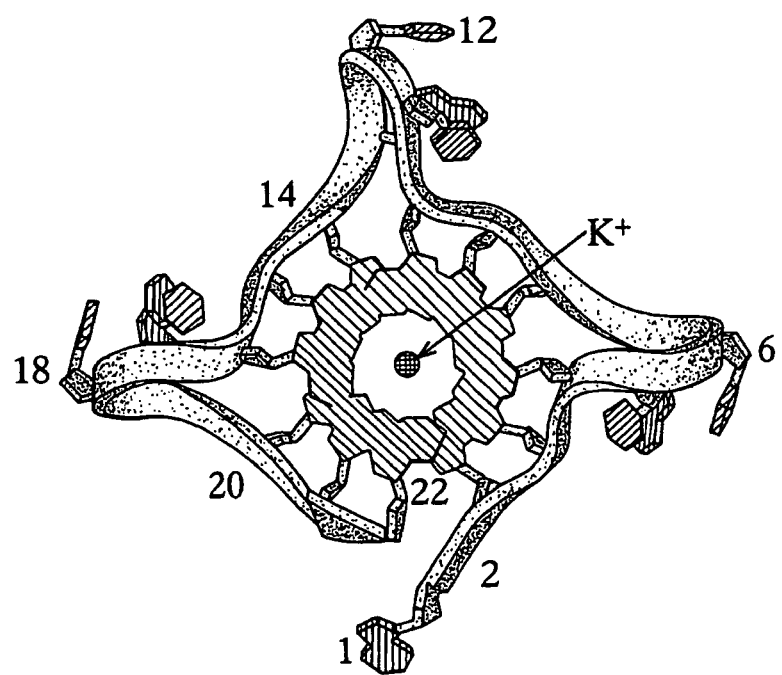
Figure 3C:
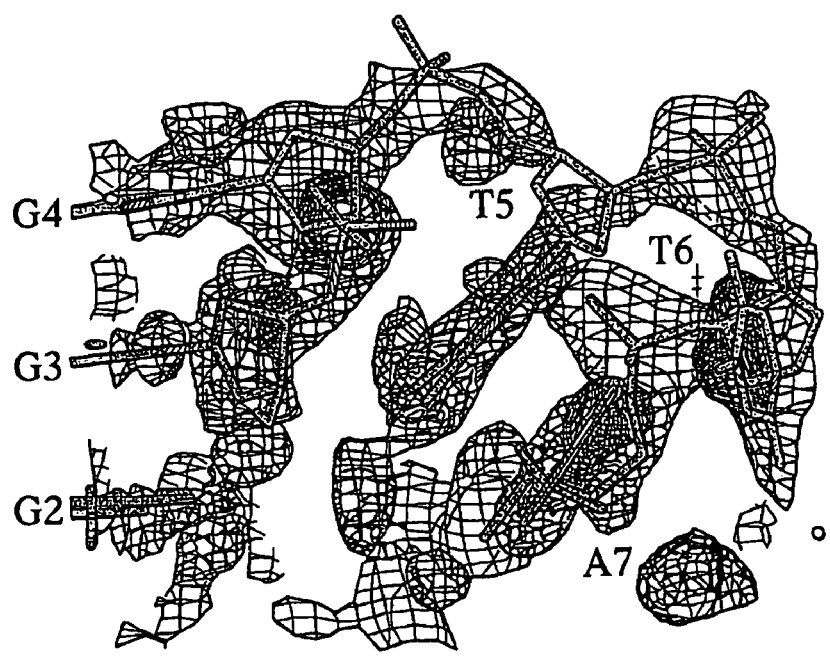
Figure 3D:
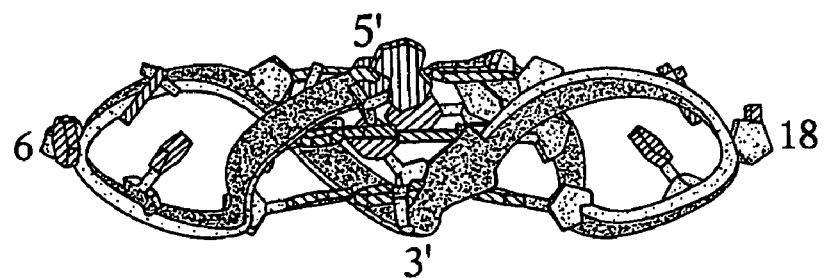
Figure 3E:
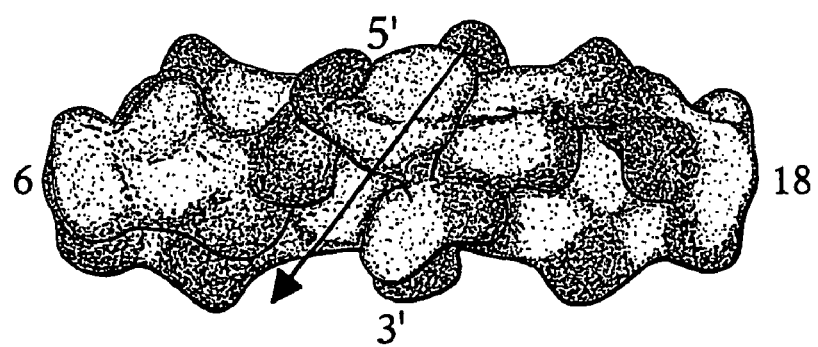
Figure 4A:
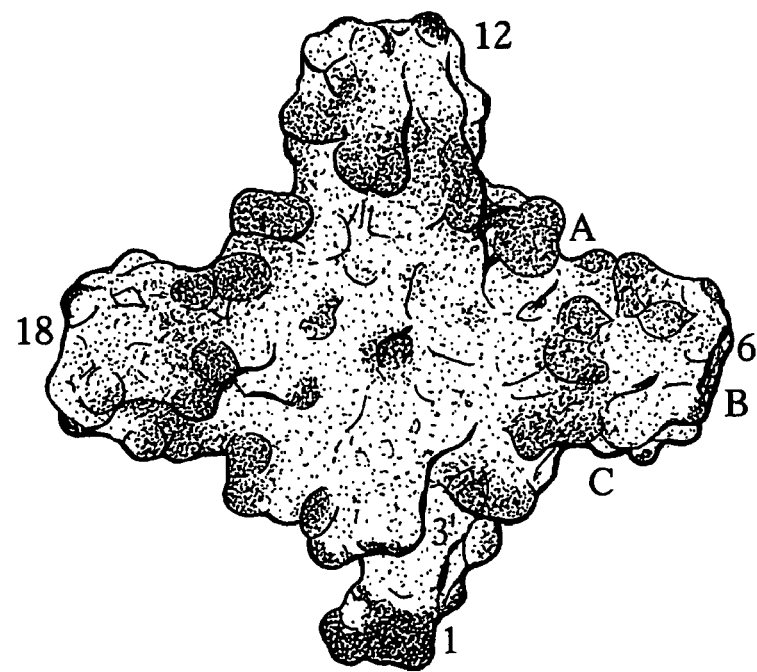
FIG. 4a, Space-filling van der Waals contoured visualisation, highlighting the channels between the TTA loops and the G tetrads, shaded by charge. Solvent atoms are removed, and view is onto the 3' G tetrad plane. b, View onto the 5' G-tetrad plane highlighting the differences between the 5' and 3' surfaces. c, Model showing two telomeric human G-quadruplex repeats stacked 3' to 5'. The upper stack has been rotated 33° relative to the lower quadruplex, with an unmodified TTA loop modeled between the two to link them. d, A model for higher order telomeric DNA structure at the end of a human chromosome. Four quadruplex repeats have been stacked using the same building method employed in FIG. 4c. A fifth quadruplex repeat is shown linked and folding onto the stack.
Figure 4B:
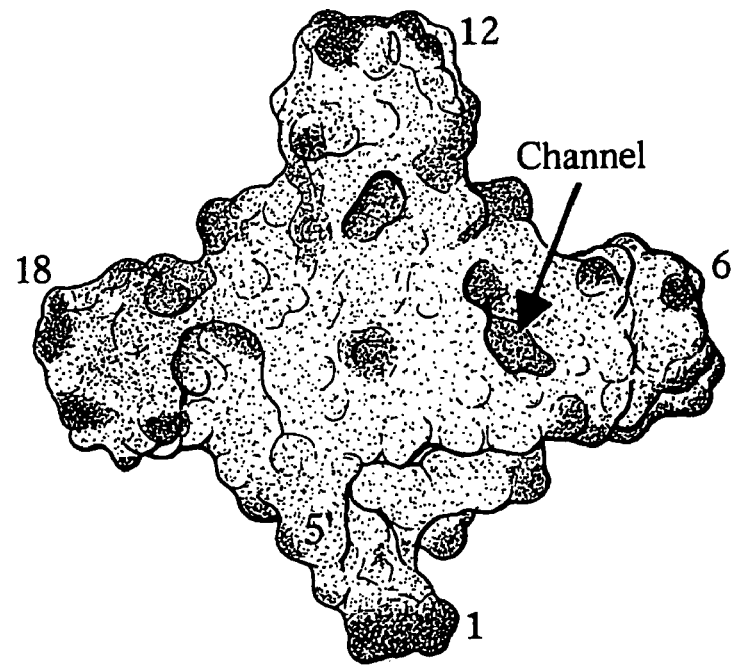
Figure 4C:
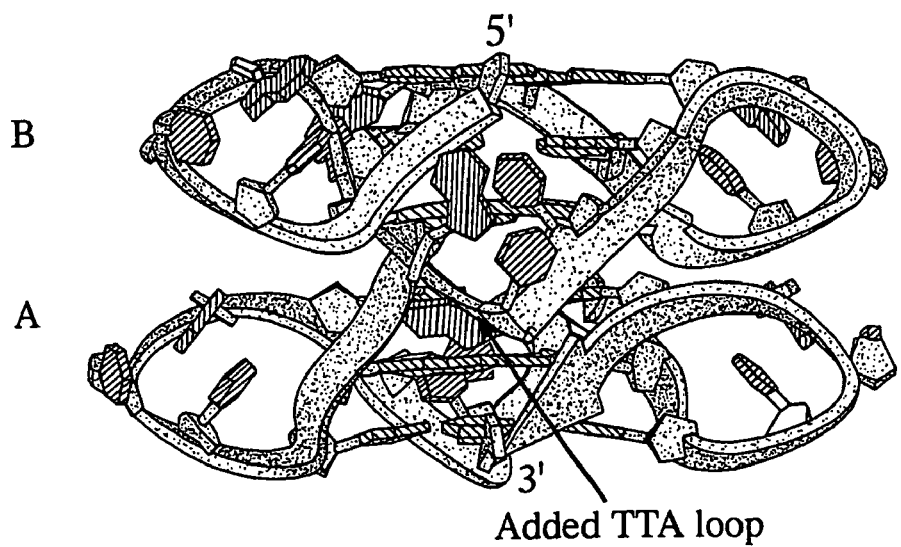
Figure 4D:
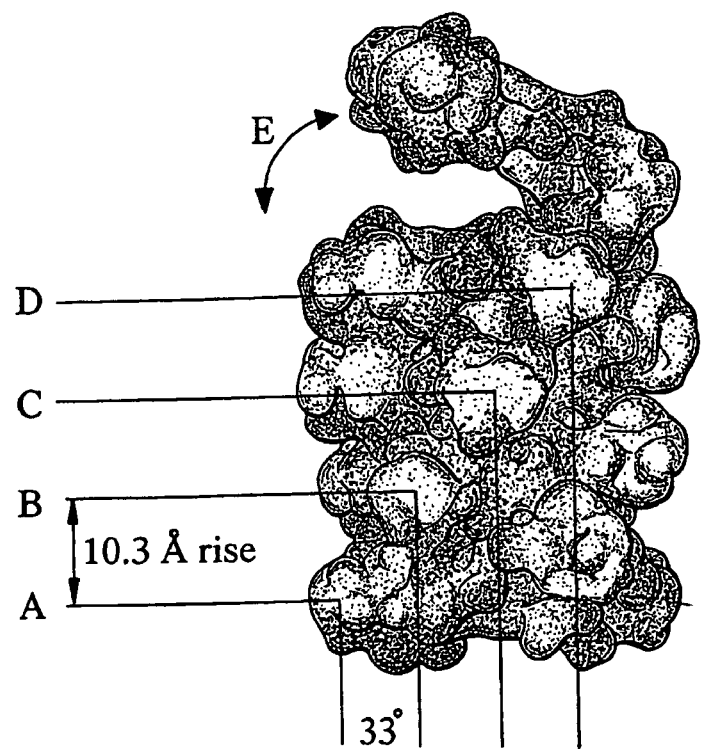

Data for the 22-mer human G-quadruplex were collected using a single flash-frozen crystal at 100° K on the ESRF beamline ID14.2 at Grenoble, France. The crystal was first cryoprotected in 500 mM KI, 15% PEG 400, 50 mM potassium cacodylate buffered at pH 6.5, and 17% glycerol. Data were processed and scaled as before. The structure was determined by molecular replacement using CNS the G-quartet core of the dimeric G-quadruplex structure as a starting-point. This model accounted for 73% of the scattering mass. Rigid body refinement was followed by minimization with CNS and iterative cycles of manual fitting. Subsequent difference Fourier maps revealed all three TTA loops not included in the initial model. Further model building and refinement was then performed with Shelx-97 to 2.1 Å resolution. All three of the TTA loops are clearly visible in the $α_A$-weighted ($2F_o$-$F_c$) density maps (FIG. 3c). The final nucleotide A1 hydrogen bonds to a symmetry-related TTA loop that was included during the latter part of the refinement. The model was further refined with solvent molecules included, using data from 10-2.1 Å, to R and $R_{free}$ values of 22.6% and 26.5% respectively. Refinement statistics are given in Table 3. Atomic coordinates of the crystal of SEQ ID NO:1 is shown as Table 1 below and the coordinates of the crystal of SEQ ID NO:2 as Table 2.

TABLE 3

X-Ray structure determination and refinement statistics

| Space Group Unit cell (Å) | $P3_1 21$ | | | | P6 |
|---|---|---|---|---|---|
| a = | 56.607 | | | | 56.682 |
| b = | 56.607 | | | | 56.682 |
| c = | 40.546 | | | | 42.106 |
| Data collection (Å) | Native | Peak | Inflection | Remote | Native |
| Wavelength (Å) | 1.542 | 0.9203 | 0.9204 | 0.9171 | 0.9202 |
| Resolution (Å) | 2.40 | 2.60 | 2.80 | 2.90 | 2.1 |
| Reflections Total | 64877 | 28965 | 23036 | 20349 | 50951 |
| Unique | 3130 | 2513 | 2017 | 1792 | 4595 |
| Average Redundancy | 10 | 8 | 6.5 | 6 | 12 |
| Completeness[a] (%) | 99.2 (99.7) | 99.8 (100) | 99.6 (100) | 99.9 (100) | 98.0 (97.8) |
| $R_{sym}$[b] (%) | 0.068 | 0.091 | 0.075 | 0.081 | 0.052 |
| I > 2 σ (I) last shell (%) | 82.4 | 83.3 | 55.1 | 50.0 | 88 |
| Average I/σ (I) | 15 | 14 | 12 | 10 | >20 |
| Phasing power[c] (acentric/centric) | | 0.952 (1.27) | | | |
| Mean figure of merit[a,c] | | (20-2.9) | 0.521 | | |
| DM mean figure of merit | | (20-2.7) | 0.888 | | |
| Refinement Resolution range (Å) | 10-2.4 | | | | 10-2.1 |
| Final R-factor/$R_{free}$[d] (%) | 18.6/26.1 | | | | 22.6/26.2 |
| Average B factor (Å²) | 37 | | | | 33 |
| Number of water molecules | 44 | | | | 68 |
| Number of Ions | 3.0 | | | | 2.5 |

[a]Highest resolution shell in parentheses.
[b]$R_{sym} = Σ_{hkl}|(Ihkl) - <I(hkl)>|/Σ I(hkl)$
[c]Taken from CNS.
[d]R-factor = $Σ_{hkl}|F_{obs}| - |F_{calc}|/Σ_{hkl}|F_{obs}|$. For $R_{free}$ calculation, 5% of the test set amplitudes were employed, that were not used in refinement.

Phasing power=<$F_H$/LOC>, where LOC is the lack of closure. $R_{cullis}$=| $|F_{PH}+_F_P|-F_H|/|F_{PH}-F_P|$ for centric reflections.

The sequences studied, d(TAGGGTTAGGGT) (SEQ ID NO:2) and d[AGGG(TTAGGG)₃] (SEQ ID NO:1), both form quadruplexes that have approximately four-fold non-crystallographic symmetry for the central core of three G-quartets. The backbone of each 12-mer has one TTA moiety, which forms a loop that projects outwards from the semi-circle of the backbone (FIGS. 2a, b). The loop connects the top of one strand with the bottom of the other, ensuring their parallelism and the integrity of the G-quartets. Thus the resulting quadruplex has two such loops, opposite to one another. All the guanine glycosidic angles are in the anti conformation, with C2'-endo sugar puckers. The twelve guanines from the two strands are arranged into three stacked G-quartets, that generate a structure (FIG. 2b) that resembles a flattened disc, 41 Å wide and 6.3 Å high. The two TTA loops, one from each strand, protrude outwards like the blades of a propeller. The G-tetrads in the 22-mer intramolecular quadruplex have an identical arrangement, and again the strand polarities are all parallel. There are three TTA groups in the sequence, and all three form these TTA loops. The morphology of this quadruplex is thus closely similar to that of the 12-mer dimer, except that there are now three protruding loops, enhancing the propeller-like appearance of the quadruplex (FIGS. 3b, d).

The G-tetrads in both quadruplexes all have the characteristic square planar arrangement found in simple quadruplexes, with base pairing through their Watson-Crick and Hoogsteen edges. The local G-tetrad rise is 3.13 Å, with an average 30° twist between successive ones. Monovalent $K^+$ ions are positioned between the stacked G-tetrads, 2.7 Å from each of the eight O6 carbonyl groups, in a bipyramidal antiprismatic arrangement (the same as observed by us in two crystal structures of an Oxytricha $K^+$ quadruplex) [Haider et al, to be published]. The backbone torsion angles in both human quadruplex structures are all with standard DNA values except for that for one bond at each stacked G/TTA loop interface. The loops are involved in a range of hydrogen bonding and stacking interactions with symmetry-related molecules in the crystal lattices. Remarkably, these have little effect on their conformations since all the loops in both structures are very similar, with the adenine in each TTA sequence swung back so that it intercalates between the two thymines. This results in the second thymine in each loop adopting a C3'-endo sugar pucker, whereas the other thymine and the adenine both adopt C2'-endo puckers. The second thymine of each loop is positioned at the tip of the loop, such that it can interact in a variety of ways with other molecules. Its interactions observed in the crystal lattice include stacking with a guanine and thymine . . . thymine O2 . . . N3 base pairing. These suggest that these loops are the means whereby quadruplexes can interact with other molecules, such as those involved in the telomere. The closest example to these loops linking parallel strands is observed in the solution structure[18] of the Tetrahymeha telomere repeat $d(T_2G_4)_4$, with two thymines linking the guanines across a three-guanine tetrad stack.

As a consequence of extending laterally up to 10 Å from the core G-quartets the TTA loops in both structures generate three very different categories of surface (FIG. 3a): a polarised surface, a hydrophobic aromatic planar surface and a TAT loop hydrogen-bonding interface, as described above. The 12-mer dimeric quadruplex has one planar surface involved with the stacking of a pair of adenines, and above them a pair of thymines from the 5' ends of each strand. These are related by a crystallographic two-fold axis, which results in them becoming two stacked (and symmetry equivalent) TATA quartets, with the adenines and thymines from a second, two-fold related G-quadruplex. The TATA quartet also has its bases hydrogen bonded through their Watson-Crick and Hoogsteen edges, with conventional AT Watson-Crick base pairing together with hydrogen bonds between N6 (adenine) and O4 (thymine). The counter-ion between the terminal G-tetrad and the TATA quartet of the dimeric intermolecular G-quadruplex was found to be a sodium ion and does not display the same coordination geometry as the potassium ions in these structures. End-to-end stacking through the planar TATA quartets results in a stacked 5' to 5' dimeric bimolecular quadruplex, with the TTA loops of the second symmetry-related G-quadruplex rotated by about 45° about the helical axis away from the TTA loops below. Packing of the 22-mer intramolecular quadruplex in the lattice also occurs via a 5' to 5' arrangement by directly involving the quadruplex G quartets; this hydrophobic 5' face is different from the more hydrophilic 3' face (FIGS. 3a, b).

All four grooves between the phosphate backbone contain a number of water molecules, in hydrogen-bonding proximity to sugar O3', and phosphate O1P atoms, as well as to guanine N2 atoms. Only slight variations in groove width are observed between the four, apparently dependent upon the presence or lack of a TTA linkage, with widths varying between 8.8 Å and 10.3 Å. The presence of the loops in the grooves gives them a distinct character. Rather than being continuous from one end of the G-quartet stack to the other, these grooves are finite, V-shaped and have walls that are not simply comprising phosphate-sugar backbones. Solvent molecules form clustered networks that reflect this increased groove complexity compared to the simpler spines of hydration observed in the Oxytricha quadruplex crystal structure. Many characteristics of G-quadruplex stabilizing ligands can now be rationalized in the light of this new structure for human quadruplexes. These ligands, typified by substituted acridines[13, 19, 20] tetra-N-pyridyl porphyrins[21] and ethidium derivatives[22, 23] share common features of large planar surface areas together with cationic side-chains. NMR chemical shift and molecular modeling studies have suggested that these ligands interact at the ends of the G-quartet stacks[24, 25]. It is apparent that this interaction can readily occur through $\pi$-stacking, unhindered by the need to change lateral and diagonal loop conformation in order to do so, which would be the case with anti-parallel quadruplexes. There are four equally spaced phosphate grooves for the binding of ligand substituents, together with the extra cavities adjacent to the loops. Preliminary modeling studies suggest that the potent trisubstituted ligand earlier designed and synthesised by us[13], is consistent with these features. At the same time, the complexity of the loop organization is suggesting new types of ligand, whose features are very different from existing ones, and thus may confer greater specificity. We also note that the rapid folding kinetics noted for the human two-repeat dimer when binding to a ligand[26], is readily accommodated by the present structure, as compared to an anti-parallel hairpin one.

The present parallel structures have a fold that is much simpler than those in existing antiparallel structural models, suggesting an obvious pathway for readily folding and unfolding G-quadruplex structures. The hypothesis that quadruplex types are structures are intermediates in recombination, would require such a facile folding/unfolding. Previously observed topologies, as seen in the Oxytricha and $Na^+$-containing four repeat human quadruplex, present a topological problem when attempting to model extended quadruplex telomeric sequences. Knots would quickly form when folding or unfolding these longer sequences. The present structures do not present any such topological difficulties when extended to longer telomeric sequences. Indeed the oligomerisation of individual quadruplexes can be simply performed by inserting an additional $4^{th}$ TTA loop to each 22-mer structure (FIG. 4 c, d). A 200 bp telomeric DNA sequence, if folded into a stack of quadruplexes, would form a ca 60 Å long cylindrical quasi-superhelix (compared to a 680 Å long B-DNA helix). The loops form a regular array on the exterior of the superhelix, suitable for interaction with telomeric proteins such as TRF1 or with the nuclear envelope, or for inhibiting telomerase extension, especially when stabilized by ligand binding.

REFERENCES

1. Hackett, J. A., Feldser, D. M. & Greider, C. W. Telomere dysfunction increases mutation rate and genomic instability. *Cell* 106, 275-286 (2001).
2. Smith, F. W. & Feigon, J. Quadruplex structure of Oxytricha telomeric DNA oligonucleotides. *Nature* 356, 164-168 (1992).
3. Wang, Y. & Patel, D. J. Guanine residues in d($T_2AG_3$) and d($T_2G_4$) form parallel-stranded potassium cation stabilized G-quadruplexes with anti glycosidic torsion angles in solution. *Biochemistry* 31, 8112-8119 (1992).
4. Horvath, M. P. & Schultz, S. C. DNA G-quartets in a 1.86 Å resolution structure of an Oxytricha nova telomeric protein-DNA complex. *J. Mol. Biol.* 310, 367-377 (2001).
5. Dubrana, K., Perrod, S. & Gasser, S. M. Turning telomeres off and on. *Curr. Opin. Cell Biol.* 13, 281-289 (2001).
6. Wang, Y. & Patel, D. J. Solution structure of the human telomeric repeat d[$AG_3(T_2AG_3)_3$] G-tetraplex. *Structure* 1, 263-282 (1993).
7. Cimino-Reale, G. et al. The length of telomeric G-rich strand 3'-overhang measured by oligonucleotide ligation assay. *Nucleic Acids Res.* 29, E35 (2001).
8. Simonsson, T. G-quadruplex DNA structures—variations on a theme. *Biol. Chem.* 382, 621-628 (2001).
9. Phillips, K., Dauter, Z., Murchie, A. I., Lilley, D. M. & Luisi, B. The crystal structure of a parallel-stranded guanine tetraplex at 0.95 Å resolution. *J. Mol. Biol.* 273, 171-82 (1997).
10. Mergny, J.-L. & Hélène, C. G-quadruplex DNA: a target for drug design. *Nature Genetics* 4, 1366-1367 (1998).
11. Bearss, D. J., Hurley, L. H. & Von Hoff, D. D. Telomere maintenance mechanisms as a target for drug development. *Oncogene* 19, 6632-6641 (2000).
12. Gowan, S. M., Heald, R., Stevens, M. F. & Kelland, L. R. Potent inhibition of telomerase by small-molecule pentacyclic acridines capable of interacting with G-quadruplexes. *Mol. Pharmacol.* 60, 981-988 (2001).
13. Read, M. A. et al. Structure-based design of selective and potent G quadruplex-mediated telomerase inhibitors. *Proc. Natl. Acad. Sci. USA* 98, 4844-4849 (2001).
14. Sun, H., Yabuki, A. & Maizels, N. A human nuclease specific for G4 DNA. *Proc. Natl. Acad. Sci. USA* 98, 12444-12449 (2001).
15. Li, J.-L. et al. Inhibition of the Bloom's and Werner's Syndrome Helicases by G-Quadruplex Interacting Ligands. *Biochemistry* 40, 15194-15202 (2001).
16. Smith, F. W., Schultze, P. & Feigon, J. Solution structures of unimolecular quadruplexes formed by oligonucleotides containing Oxytricha telomere repeats. *Structure* 3, 997-1008 (1995).
17. Balagurumoorthy, P. B. & Brahmachari, S. K. Structure and stability of human telomeric sequence. *J. Biol. Chem.* 269, 21858-21869 (1994).
18. Wang, Y. & Patel, D. J. Solution structure of the tetrahymena telomeric repeat d($T_2G_4$)$_4$. *Structure* 2, 1141-1156 (1994).
19. Read, M. A. et al. Molecular modeling studies on G-quadruplex complexes of telomerase inhibitors: Structure-activity relationships. *J. Med. Chem.* 42, 4538-4546 (1999).
20. Harrison, R. J., Gowan, S. M., Kelland, L. R. & Neidle, S. Human telomerase inhibition by substituted acridine derivatives. *Bioorg. Med. Chem. Lett.* 9, 2463-2468 (1999).
21. Han, H., Langley, D. R., Rangan, A. & Hurley, L. H. Selective interactions of cationic porphyrins with G-quadruplex structures. *J. Amer. Chem. Soc.* 123, 8902-8913 (2001).
22. Mergny, J. L. et al. Telomerase inhibitors based on quadruplex ligands selected by a fluorescence assay. *Proc. Natl. Acad. Sci. USA* 98, 3062-3067 (2001).
23. Koeppel, F. et al. Ethidium derivatives bind to G-quartets, inhibit telomerase and act as fluorescent probes for quadruplexes. *Nucleic Acids Res.* 29, 1087-1096 (2001).
24. Fedoroff, O. Y., et al., NMR-Based model of a telomerase-inhibiting compound bound to G-quadruplex DNA. *Biochemistry* 37, 12367-12374 (1998).
25. Read, M. A. & Neidle, S. Structural characterization of a guanine-quadruplex ligand complex. *Biochemistry* 39, 13422-13432 (2000).
26. Han, H., Cliff, C. L. & Hurley, L. H. Accelerated assembly of G-quadruplex structures by a small molecule. *Biochemistry* 38, 6981-6986 (1999).
27. Otwinowski, Z. M. & Manor, W. Processing of X-ray diffraction data collected in oscillation mode. *Methods Enzymol.* 276, 307-326 (1997).
28. Brünger, A. T. et al. Crystallography & NMR system: A new software suite for macromolecular structure determination. *Acta. Crystallogr. D* 54, 905-921 (1998).
29. Sheldrick, G. M. & Schneider, T. R. SHELX-97: high-resolution refinement. *Methods Enzymol.* 276, 319-343 (1997).
30. Cambilleau, C. & Horjales, E. *J. Mol. Graphics* 5, 175-177 (1987).

TABLE 1

| HEADER | | DEOXYRIBONUCLEIC ACID |
|---|---|---|
| TITLE | | STRUCTURE AND PACKING OF HUMAN TELOMERIC DNA |
| COMPND | | MOL_SEQ ID NO: 1; |
| COMPND | 2 | MOLECULE: 5'- |
| COMPND | 3 | D(*AP*GP*GP*GP*TP*TP*AP*GP*GP*GP*TP*TP*AP*GP*GP*GP*TP*TP*AP |
| COMPND | 4 | *GP*GP*G)-3; |
| COMPND | 5 | CHAIN: A; |
| COMPND | 6 | ENGINEERED: YES; |
| REMARK | 1 | |
| REMARK | 2 | |
| REMARK | 2 | RESOLUTION. 2.10 ANGSTROMS. |
| REMARK | 3 | |

TABLE 1-continued

| REMARK | 3 | REFINEMENT. | |
|---|---|---|---|
| REMARK | 3 | PROGRAM | SHELXL-97 |
| REMARK | 3 | AUTHORS | G. M. SHELDRICK |
| REMARK | 3 | | |
| REMARK | 3 | DATA USED IN REFINEMENT. | |
| REMARK | 3 | RESOLUTION RANGE HIGH (ANGSTROMS) | 2.10 |
| REMARK | 3 | RESOLUTION RANGE LOW (ANGSTROMS) | 10.00 |
| REMARK | 3 | DATA CUTOFF (SIGMA(F)) | 0.000 |
| REMARK | 3 | COMPLETENESS FOR RANGE (%) | NULL |
| REMARK | 3 | CROSS-VALIDATION METHOD | THROUGHOUT |
| REMARK | 3 | FREE R VALUE TEST SET SELECTION | RANDOM |
| REMARK | 3 | | |
| REMARK | 3 | FIT TO DATA USED IN REFINEMENT (NO CUTOFF). | |
| REMARK | 3 | R VALUE (WORKING + TEST SET, NO CUTOFF) | 0.235 |
| REMARK | 3 | R VALUE (WORKING SET, NO CUTOFF) | 0.231 |
| REMARK | 3 | FREE R VALUE (NO CUTOFF) | 11 0.263 |
| REMARK | 3 | FREE R VALUE TEST SET SIZE (%, NO CUTOFF) | NULL |
| REMARK | 3 | FREE R VALUE TEST SET COUNT (NO CUTOFF) | 441 |
| REMARK | 3 | TOTAL NUMBER OF REFLECTIONS (NO CUTOFF) | 4416 |
| REMARK | 3 | | |
| REMARK | 3 | FIT/AGREEMENT OF MODEL FOR DATA WITH F > 4SIG(F). | |
| REMARK | 3 | R VALUE (WORKING + TEST SET, F > 4SIG(F)) | NULL |
| REMARK | 3 | R VALUE (WORKING SET, F > 4SIG(F)) | NULL |
| REMARK | 3 | FREE R VALUE (F > 4SIG(F)) | NULL |
| REMARK | 3 | FREE R VALUE TEST SET SIZE (%, F > 4SIG(F)) | NULL |
| REMARK | 3 | FREE R VALUE TEST SET COUNT (F > 4SIG(F)) | NULL |
| REMARK | 3 | TOTAL NUMBER OF REFLECTIONS (F > 4SIG(F)) | NULL |
| REMARK | 3 | | |
| REMARK | 3 | NUMBER OF NON-HYDROGEN ATOMS USED IN REFINEMENT. | |
| REMARK | 3 | PROTEIN ATOMS | 0 |
| REMARK | 3 | NUCLEIC ACID ATOMS | 465 |
| REMARK | 3 | HETEROGEN ATOMS | 3 |
| REMARK | 3 | SOLVENT ATOMS | 68 |
| REMARK | 3 | | |
| REMARK | 3 | MODEL REFINEMENT. | |
| REMARK | 3 | OCCUPANCY SUM OF NON-HYDROGEN ATOMS | NULL |
| REMARK | 3 | OCCUPANCY SUM OF HYDROGEN ATOMS | NULL |
| REMARK | 3 | NUMBER OF DISCRETELY DISORDERED RESIDUES | NULL |
| REMARK | 3 | NUMBER OF LEAST-SQUARES PARAMETERS | NULL |
| REMARK | 3 | NUMBER OF RESTRAINTS | NULL |
| REMARK | 3 | | |
| REMARK | 3 | RMS DEVIATIONS FROM RESTRAINT TARGET VALUES. | |
| REMARK | 3 | BOND LENGTHS (A) | 0.005 |
| REMARK | 3 | ANGLE DISTANCES (A) | 0.015 |
| REMARK | 3 | SIMILAR DISTANCES (NO TARGET VALUES) (A) | NULL |
| REMARK | 3 | DISTANCES FROM RESTRAINT PLANES (A) | 0.007 |
| REMARK | 3 | ZERO CHIRAL VOLUMES (A**3) | NULL |
| REMARK | 3 | NON-ZERO CHIRAL VOLUMES (A**3) | NULL |
| REMARK | 3 | ANTI-BUMPING DISTANCE RESTRAINTS (A) | 0.003 |
| REMARK | 3 | RIGID-BOND ADP COMPONENTS (A**2) | NULL |
| REMARK | 3 | SIMILAR ADP COMPONENTS (A**2) | NULL |
| REMARK | 3 | APPROXIMATELY ISOTROPIC ADPS (A**2) | NULL |
| REMARK | 3 | | |
| REMARK | 3 | BULK SOLVENT MODELING. | |
| REMARK | 3 | METHOD USED | NULL |
| REMARK | 3 | | |
| REMARK | 3 | STEREOCHEMISTRY TARGET VALUES | PARKINSON ET AL. |
| REMARK | 3 | SPECIAL CASE | NULL |
| REMARK | 3 | | |
| REMARK | 3 | OTHER REFINEMENT REMARKS | NULL |
| REMARK | 4 | | |
| REMARK | 4 | COMPLIES WITH FORMAT V. 2.3, 09-JULY-1998 | |
| REMARK | 102 | | |
| REMARK | 102 | BASES G A 20 AND G A 14 ARE MISPAIRED. | |
| REMARK | 105 | | |
| REMARK | 105 | THE PROTEIN DATA BANK HAS ADOPTED THE SACCHARIDE CHEMISTS | |
| REMARK | 105 | NOMENCLATURE FOR ATOMS OF THE DEOXYRIBOSE/RIBOSE MOIETY | |
| REMARK | 105 | RATHER THAN THAT OF THE NUCLEOSIDE CHEMISTS. THE RING | |
| REMARK | 105 | OXYGEN ATOM IS LABELLED O4* INSTEAD OF O1*. | |
| REMARK | 200 | | |
| REMARK | 200 | EXPERIMENTAL DETAILS | |
| REMARK | 200 | EXPERIMENT TYPE | X-RAY DIFFRACTION |
| REMARK | 200 | TEMPERATURE (KELVIN) | 103.0 |
| REMARK | 200 | PH | 6.50 |
| REMARK | 200 | NUMBER OF CRYSTALS USED | 1 |
| REMARK | 200 | | |
| REMARK | 200 | SYNCHROTRON (Y/N) | Y |
| REMARK | 200 | RADIATION SOURCE | EMBL BM14.2 GRENOBLE |
| REMARK | 200 | BEAMLINE | NULL |

TABLE 1-continued

| REMARK | 200 | X-RAY GENERATOR MODEL | NULL |
|---|---|---|---|
| REMARK | 200 | MONOCHROMATIC OR LAUE (M/L) | M |
| REMARK | 200 | WAVELENGTH OR RANGE (A) | 0.901 |
| REMARK | 200 | MONOCHROMATOR | SI 111 |
| REMARK | 200 | OPTICS | NULL |
| REMARK | 200 | | |
| REMARK | 200 | DETECTOR TYPE | CCD |
| REMARK | 200 | DETECTOR MANUFACTURER | ADSC QUANTUM 4 |
| REMARK | 200 | INTENSITY-INTEGRATION SOFTWARE | DENZO |
| REMARK | 200 | DATA SCALING SOFTWARE | SCALEPACK |
| REMARK | 200 | | |
| REMARK | 200 | NUMBER OF UNIQUE REFLECTIONS | 4304 |
| REMARK | 200 | RESOLUTION RANGE HIGH (A) | 2.100 |
| REMARK | 200 | RESOLUTION RANGE LOW (A) | 20.000 |
| REMARK | 200 | REJECTION CRITERIA (SIGMA(I)) | 2.000 |
| REMARK | 200 | | |
| REMARK | 200 | OVERALL. | |
| REMARK | 200 | COMPLETENESS FOR RANGE (%) | 93.8 |
| REMARK | 200 | DATA REDUNDANCY | 4.000 |
| REMARK | 200 | R MERGE (I) | 0.05200 |
| REMARK | 200 | R SYM (I) | NULL |
| REMARK | 200 | <I/SIGMA(I)> FOR THE DATA SET | 50.0000 |
| REMARK | 200 | | |
| REMARK | 200 | IN THE HIGHEST RESOLUTION SHELL. | |
| REMARK | 200 | HIGHEST RESOLUTION SHELL, RANGE HIGH (A) | 2.10 |
| REMARK | 200 | HIGHEST RESOLUTION SHELL, RANGE LOW (A) | 2.17 |
| REMARK | 200 | COMPLETENESS FOR SHELL (%) | 97.8 |
| REMARK | 200 | DATA REDUNDANCY IN SHELL | 4.00 |
| REMARK | 200 | R MERGE FOR SHELL (I) | 0.11700 |
| REMARK | 200 | R SYM FOR SHELL (I) | NULL |
| REMARK | 200 | <I/SIGMA(I)> FOR SHELL | 15.000 |
| REMARK | 200 | | |
| REMARK | 200 | DIFFRACTION PROTOCOL | SINGLE WAVELENGTH |
| REMARK | 200 | METHOD USED TO DETERMINE THE STRUCTURE | MOLECULAR REPLACEMENT |
| REMARK | 200 | SOFTWARE USED | CNS |
| REMARK | 200 | STARTING MODEL | PDB ENTRY 1K8P |
| REMARK | 200 | | |
| REMARK | 200 | REMARK | NULL |
| REMARK | 280 | | |
| REMARK | 280 | CRYSTAL | |
| REMARK | 280 | SOLVENT CONTENT, VS (%) | NULL |
| REMARK | 280 | MATTHEWS COEFFICIENT, VM (ANGSTROMS**3/DA) | NULL |
| REMARK | 280 | | |
| REMARK | 280 | CRYSTALLIZATION CONDITIONS | PEG 400, POTASSIUM IODIDE, |
| REMARK | 280 | POTASSIUM CHLORIDE | |
| REMARK | 290 | | |
| REMARK | 290 | CRYSTALLOGRAPHIC SYMMETRY | |
| REMARK | 290 | SYMMETRY OPERATORS FOR SPACE GROUP | P 6 |
| REMARK | 290 | | |
| REMARK | 290 | SYMOP   SYMMETRY | |
| REMARK | 290 | NNNMMM  OPERATOR | |
| REMARK | 290 | 1555    X, Y, Z | |
| REMARK | 290 | 2555    −Y, X − Y, Z | |
| REMARK | 290 | 3555    −X + Y, −X, Z | |
| REMARK | 290 | 4555    −X, −Y, Z | |
| REMARK | 290 | 5555    Y, − X + Y, Z | |
| REMARK | 290 | 6555    X − Y, X, Z | |
| REMARK | 290 | | |
| REMARK | 290 | WHERE NNN -> OPERATOR NUMBER | |
| REMARK | 290 | MMM -> TRANSLATION VECTOR | |
| REMARK | 290 | | |
| REMARK | 290 | CRYSTALLOGRAPHIC SYMMETRY TRANSFORMATIONS | |
| REMARK | 290 | THE FOLLOWING TRANSFORMATIONS OPERATE ON THE ATOM/HETATM | |
| REMARK | 290 | RECORDS IN THIS ENTRY TO PRODUCE CRYSTALLOGRAPHICALLY | |
| REMARK | 290 | RELATED MOLECULES. | |
| REMARK | 290 | SMTRY1  1   1.000000   0.000000   0.000000  0.00000 | |
| REMARK | 290 | SMTRY2  1   0.000000   1.000000   0.000000  0.00000 | |
| REMARK | 290 | SMTRY3  1   0.000000   0.000000   1.000000  0.00000 | |
| REMARK | 290 | SMTRY1  2  −0.500000  −0.866025   0.000000  0.00000 | |
| REMARK | 290 | SMTRY2  2   0.866025  −0.500000   0.000000  0.00000 | |
| REMARK | 290 | SMTRY3  2   0.000000   0.000000   1.000000  0.00000 | |
| REMARK | 290 | SMTRY1  3  −0.500000   0.866025   0.000000  0.00000 | |
| REMARK | 290 | SMTRY2  3  −0.866025  −0.500000   0.000000  0.00000 | |
| REMARK | 290 | SMTRY3  3   0.000000   0.000000   1.000000  0.00000 | |
| REMARK | 290 | SMTRY1  4  −1.000000   0.000000   0.000000  0.00000 | |
| REMARK | 290 | SMTRY2  4   0.000000  −1.000000   0.000000  0.00000 | |
| REMARK | 290 | SMTRY3  4   0.000000   0.000000   1.000000  0.00000 | |
| REMARK | 290 | SMTRY1  5   0.500000   0.866025   0.000000  0.00000 | |
| REMARK | 290 | SMTRY2  5  −0.866025   0.500000   0.000000  0.00000 | |

TABLE 1-continued

| | | | | | | | | |
|---|---|---|---|---|---|---|---|---|
| REMARK | 290 | SMTRY3 | 5 | 0.000000 | 0.000000 | 1.000000 | 0.00000 | |
| REMARK | 290 | SMTRY1 | 6 | 0.500000 | −0.866025 | 0.000000 | 0.00000 | |
| REMARK | 290 | SMTRY2 | 6 | 0.866025 | 0.500000 | 0.000000 | 0.00000 | |
| REMARK | 290 | SMTRY3 | 6 | 0.000000 | 0.000000 | 1.000000 | 0.00000 | |
| REMARK | 290 | | | | | | | |
| REMARK | 290 | REMARK: NULL | | | | | | |
| REMARK | 300 | | | | | | | |
| REMARK | 300 | BIOMOLECULE: 1 | | | | | | |
| REMARK | 300 | THIS ENTRY CONTAINS THE CRYSTALLOGRAPHIC ASYMMETRIC UNIT | | | | | | |
| REMARK | 300 | WHICH CONSISTS OF 1 CHAIN(S). SEE REMARK 350 FOR | | | | | | |
| REMARK | 300 | INFORMATION ON GENERATING THE BIOLOGICAL MOLECULE(S). | | | | | | |
| REMARK | 350 | | | | | | | |
| REMARK | 350 | GENERATING THE BIOMOLECULE | | | | | | |
| REMARK | 350 | COORDINATES FOR A COMPLETE MULTIMER REPRESENTING THE KNOWN | | | | | | |
| REMARK | 350 | BIOLOGICALLY SIGNIFICANT OLIGOMERIZATION STATE OF THE | | | | | | |
| REMARK | 350 | MOLECULE CAN BE GENERATED BY APPLYING BIOMT TRANSFORMATIONS | | | | | | |
| REMARK | 350 | GIVEN BELOW. BOTH NON-CRYSTALLOGRAPHIC AND | | | | | | |
| REMARK | 350 | CRYSTALLOGRAPHIC OPERATIONS ARE GIVEN. | | | | | | |
| REMARK | 350 | | | | | | | |
| REMARK | 350 | BIOMOLECULE: 1 | | | | | | |
| REMARK | 350 | APPLY THE FOLLOWING TO CHAINS: A | | | | | | |
| REMARK | 350 | BIOMT1 | 1 | 1.000000 | 0.000000 | 0.000000 | 0.00000 | |
| REMARK | 350 | BIOMT2 | 1 | 0.000000 | 1.000000 | 0.000000 | 0.00000 | |
| REMARK | 350 | BIOMT3 | 1 | 0.000000 | 0.000000 | 1.000000 | 0.00000 | |
| REMARK | 375 | | | | | | | |
| REMARK | 375 | SPECIAL POSITION | | | | | | |
| REMARK | 375 | THE FOLLOWING ATOMS ARE FOUND TO BE WITHIN 0.15 ANGSTROMS | | | | | | |
| REMARK | 375 | OF A SYMMETRY RELATED ATOM AND ARE ASSUMED TO BE ON SPECIAL | | | | | | |
| REMARK | 375 | POSITIONS. | | | | | | |
| REMARK | 375 | | | | | | | |
| REMARK | 375 | ATOM RES CSSEQI | | | | | | |
| REMARK | 375 | K    K    26    LIES ON A SPECIAL POSITION. | | | | | | |
| REMARK | 525 | | | | | | | |
| REMARK | 525 | SOLVENT | | | | | | |
| REMARK | 525 | THE FOLLOWING SOLVENT MOLECULES LIE FARTHER THAN EXPECTED | | | | | | |
| REMARK | 525 | FROM THE PROTEIN OR NUCLEIC ACID MOLECULE AND MAY BE | | | | | | |
| REMARK | 525 | ASSOCIATED WITH A SYMMETRY RELATED MOLECULE (M = MODEL | | | | | | |
| REMARK | 525 | NUMBER; RES = RESIDUE NAME; C = CHAIN IDENTIFIER; SSEQ = SEQUENCE | | | | | | |
| REMARK | 525 | NUMBER; I = INSERTION CODE): | | | | | | |
| REMARK | 525 | | | | | | | |
| REMARK | 525 | M RES CSSEQI | | | | | | |
| REMARK | 525 | 0 HOH 1065        DISTANCE = 5.57 ANGSTROMS | | | | | | |
| SEQRES | 1 A | 22 | A  G  G  G  T  T  A  G  G  G  T  T  A | | | | | |
| SEQRES | 2 A | 22 | G  G  G  T  T  A  G  G  G | | | | | |
| HET | K | 24 | 1 | | | | | |
| HET | K | 25 | 1 | | | | | |
| HET | K | 26 | 1 | | | | | |
| HETNAM | | K POTASSIUM ION | | | | | | |
| FORMUL | 2 | K    3(K1 1+) | | | | | | |
| FORMUL | 5 | HOH   *68(H2 O1) | | | | | | |
| CRYST1 | 56.682 56.682 42.106 90.00 90.00 120.00 P 6        6 | | | | | | | |
| ORIGX1 | 1.000000 | 0.000000 | 0.000000 | 0.00000 | | | | |
| ORIGX2 | 0.000000 | 1.000000 | 0.000000 | 0.00000 | | | | |
| ORIGX3 | 0.000000 | 0.000000 | 1.000000 | 0.00000 | | | | |
| SCALE1 | 0.017642 | 0.010186 | 0.000000 | 0.00000 | | | | |
| SCALE2 | 0.000000 | 0.020372 | 0.000000 | 0.00000 | | | | |
| SCALE3 | 0.000000 | 0.000000 | 0.023750 | 0.00000 | | | | |
| ATOM | 1 | O5* | A | A | 1 | 33.082 | −12.759 | −8.380 | 1.00 | 69.59 | O |
| ATOM | 2 | C5* | A | A | 1 | 33.202 | −11.645 | −7.490 | 1.00 | 72.84 | C |
| ATOM | 3 | C4* | A | A | 1 | 33.653 | −12.132 | −6.133 | 1.00 | 78.89 | C |
| ATOM | 4 | O4* | A | A | 1 | 34.074 | −13.512 | −6.233 | 1.00 | 79.10 | O |
| ATOM | 5 | C3* | A | A | 1 | 34.826 | −11.368 | −5.520 | 1.00 | 77.29 | C |
| ATOM | 6 | O3* | A | A | 1 | 34.368 | −10.743 | −4.310 | 1.00 | 77.36 | O |
| ATOM | 7 | C2* | A | A | 1 | 35.861 | −12.419 | −5.175 | 1.00 | 74.44 | C |
| ATOM | 8 | C1* | A | A | 1 | 35.479 | −13.593 | −6.047 | 1.00 | 68.28 | C |
| ATOM | 9 | N9 | A | A | 1 | 36.226 | −13.572 | −7.318 | 1.00 | 50.04 | N |
| ATOM | 10 | C8 | A | A | 1 | 35.782 | −13.526 | −8.613 | 1.00 | 46.90 | C |
| ATOM | 11 | N7 | A | A | 1 | 36.759 | −13.520 | −9.493 | 1.00 | 53.72 | N |
| ATOM | 12 | C5 | A | A | 1 | 37.918 | −13.565 | −8.726 | 1.00 | 45.83 | C |
| ATOM | 13 | C6 | A | A | 1 | 39.285 | −13.583 | −9.049 | 1.00 | 44.15 | C |
| ATOM | 14 | N6 | A | A | 1 | 39.753 | −13.556 | −10.298 | 1.00 | 46.33 | N |
| ATOM | 15 | N1 | A | A | 1 | 40.180 | −13.628 | −8.035 | 1.00 | 41.67 | N |
| ATOM | 16 | C2 | A | A | 1 | 39.712 | −13.654 | −6.783 | 1.00 | 43.13 | C |
| ATOM | 17 | N3 | A | A | 1 | 38.453 | −13.641 | −6.348 | 1.00 | 40.56 | N |
| ATOM | 18 | C4 | A | A | 1 | 37.600 | −13.596 | −7.382 | 1.00 | 44.25 | C |
| ATOM | 19 | P | G | A | 2 | 34.961 | −9.307 | −3.886 | 1.00 | 71.63 | P |
| ATOM | 20 | O1P | G | A | 2 | 36.223 | −9.007 | −4.609 | 1.00 | 41.70 | O |
| ATOM | 21 | O2P | G | A | 2 | 34.946 | −9.203 | −2.398 | 1.00 | 86.92 | O |
| ATOM | 22 | O5* | G | A | 2 | 33.826 | −8.331 | −4.457 | 1.00 | 60.81 | O |

TABLE 1-continued

| ATOM | 23 | C5* | G | A | 2 | 32.460 | −8.687 | −4.207 | 1.00 | 49.52 | C |
|---|---|---|---|---|---|---|---|---|---|---|---|
| ATOM | 24 | C4* | G | A | 2 | 31.937 | −7.766 | −3.123 | 1.00 | 42.72 | C |
| ATOM | 25 | O4* | G | A | 2 | 32.145 | −6.402 | −3.550 | 1.00 | 38.10 | O |
| ATOM | 26 | C3* | G | A | 2 | 30.451 | −7.914 | −2.836 | 1.00 | 45.92 | C |
| ATOM | 27 | O3* | G | A | 2 | 30.276 | −8.538 | −1.552 | 1.00 | 51.43 | O |
| ATOM | 28 | C2* | G | A | 2 | 29.894 | −6.514 | −2.836 | 1.00 | 39.04 | C |
| ATOM | 29 | C1* | G | A | 20 | 30.946 | −5.667 | −3.508 | 1.00 | 35.04 | C |
| ATOM | 30 | N9 | G | A | 2 | 30.492 | −5.193 | −4.828 | 1.00 | 32.98 | N |
| ATOM | 31 | C8 | G | A | 2 | 30.806 | −5.618 | −6.093 | 1.00 | 31.50 | C |
| ATOM | 32 | N7 | G | A | 2 | 30.186 | −4.933 | −7.024 | 1.00 | 34.35 | N |
| ATOM | 33 | C5 | G | A | 2 | 29.414 | −4.000 | −6.344 | 1.00 | 29.21 | C |
| ATOM | 34 | C6 | G | A | 2 | 28.529 | −2.983 | −6.778 | 1.00 | 31.03 | C |
| ATOM | 35 | O6 | G | A | 2 | 28.184 | −2.630 | −7.921 | 1.00 | 24.28 | O |
| ATOM | 36 | N1 | G | A | 2 | 27.973 | −2.285 | −5.701 | 1.00 | 32.92 | N |
| ATOM | 37 | C2 | G | A | 2 | 28.241 | −2.540 | −4.377 | 1.00 | 37.59 | C |
| ATOM | 38 | N2 | G | A | 2 | 27.626 | −1.779 | −3.460 | 1.00 | 19.50 | N |
| ATOM | 39 | N3 | G | A | 2 | 29.063 | −3.483 | −3.954 | 1.00 | 30.30 | N |
| ATOM | 40 | C4 | G | A | 2 | 29.601 | −4.158 | −4.982 | 1.00 | 24.72 | C |
| ATOM | 41 | P | G | A | 3 | 28.943 | −9.432 | −1.369 | 1.00 | 52.34 | P |
| ATOM | 42 | O1P | G | A | 3 | 29.204 | −10.534 | −0.406 | 1.00 | 79.94 | O |
| ATOM | 43 | O2P | G | A | 3 | 28.398 | −9.770 | −2.716 | 1.00 | 44.17 | O |
| ATOM | 44 | O5* | G | A | 3 | 27.906 | −8.427 | −0.689 | 1.00 | 55.52 | O |
| ATOM | 45 | C5* | G | A | 3 | 28.300 | −7.339 | 0.147 | 1.00 | 47.68 | C |
| ATOM | 46 | C4* | G | A | 3 | 27.058 | −6.520 | 0.458 | 1.00 | 41.91 | C |
| ATOM | 47 | O4* | G | A | 3 | 26.911 | −5.503 | −0.569 | 1.00 | 37.70 | O |
| ATOM | 48 | C3* | G | A | 3 | 25.771 | −7.342 | 0.418 | 1.00 | 42.03 | C |
| ATOM | 49 | O3* | G | A | 3 | 24.816 | −6.830 | 1.355 | 1.00 | 45.60 | O |
| ATOM | 50 | C2* | G | A | 3 | 25.286 | −7.132 | −1.002 | 1.00 | 37.71 | C |
| ATOM | 51 | C1* | G | A | 3 | 25.699 | −5.683 | −1.270 | 1.00 | 38.28 | C |
| ATOM | 52 | N9 | G | A | 3 | 25.818 | −5.486 | −2.731 | 1.00 | 31.21 | N |
| ATOM | 53 | C8 | G | A | 3 | 26.533 | −6.231 | −3.644 | 1.00 | 33.41 | C |
| ATOM | 54 | N7 | G | A | 3 | 26.428 | −5.791 | −4.868 | 1.00 | 29.91 | N |
| ATOM | 55 | C5 | G | A | 3 | 25.593 | −4.690 | −4.752 | 1.00 | 22.72 | C |
| ATOM | 56 | C6 | G | A | 3 | 25.131 | −3.818 | −5.773 | 1.00 | 26.25 | C |
| ATOM | 57 | O6 | G | A | 3 | 25.388 | −3.868 | −6.991 | 1.00 | 22.88 | O |
| ATOM | 58 | N1 | G | A | 3 | 24.309 | −2.833 | −5.256 | 1.00 | 21.26 | N |
| ATOM | 59 | C2 | G | A | 3 | 23.973 | −2.704 | −3.921 | 1.00 | 32.60 | C |
| ATOM | 60 | N2 | G | A | 3 | 23.158 | −1.669 | −3.647 | 1.00 | 16.05 | N |
| ATOM | 61 | N3 | G | A | 3 | 24.399 | −3.514 | −2.959 | 1.00 | 28.84 | N |
| ATOM | 62 | C4 | G | A | 3 | 25.206 | −4.489 | −3.434 | 1.00 | 31.45 | C |
| ATOM | 63 | P | G | A | 4 | 23.507 | −7.714 | 1.671 | 1.00 | 48.07 | P |
| ATOM | 64 | O1P | G | A | 4 | 23.497 | −8.071 | 3.118 | 1.00 | 84.40 | O |
| ATOM | 65 | O2P | G | A | 4 | 23.375 | −8.814 | 0.671 | 1.00 | 49.51 | O |
| ATOM | 66 | O5* | G | A | 4 | 22.266 | −6.744 | 1.411 | 1.00 | 44.95 | O |
| ATOM | 67 | C5* | G | A | 4 | 22.430 | −5.331 | 1.458 | 1.00 | 44.47 | C |
| ATOM | 68 | C4* | G | A | 4 | 21.093 | −4.675 | 1.211 | 1.00 | 47.48 | C |
| ATOM | 69 | O4* | G | A | 4 | 21.095 | −4.070 | −0.102 | 1.00 | 45.79 | O |
| ATOM | 70 | C3* | G | A | 4 | 19.898 | −5.635 | 1.214 | 1.00 | 45.87 | C |
| ATOM | 71 | O3* | G | A | 4 | 18.738 | −4.907 | 1.634 | 1.00 | 48.91 | O |
| ATOM | 72 | C2* | G | A | 4 | 19.785 | −6.029 | −0.248 | 1.00 | 44.60 | C |
| ATOM | 73 | C1* | G | A | 4 | 20.230 | −4.780 | −0.979 | 1.00 | 40.76 | C |
| ATOM | 74 | N9 | G | A | 4 | 20.905 | −5.122 | −2.251 | 1.00 | 31.38 | N |
| ATOM | 75 | C8 | G | A | 4 | 21.870 | −6.046 | −2.524 | 1.00 | 37.49 | C |
| ATOM | 76 | N7 | G | A | 4 | 22.232 | −6.067 | −3.781 | 1.00 | 31.83 | N |
| ATOM | 77 | C5 | G | A | 4 | 21.445 | −5.086 | −4.368 | 1.00 | 27.90 | C |
| ATOM | 78 | C6 | G | A | 4 | 21.389 | −4.647 | −5.720 | 1.00 | 25.65 | C |
| ATOM | 79 | O6 | G | A | 4 | 22.062 | −5.078 | −6.667 | 1.00 | 30.92 | O |
| ATOM | 80 | N1 | G | A | 4 | 20.457 | −3.633 | −5.890 | 1.00 | 27.62 | N |
| ATOM | 81 | C2 | G | A | 4 | 19.676 | −3.105 | −4.890 | 1.00 | 31.61 | C |
| ATOM | 82 | N2 | G | A | 4 | 18.834 | −2.129 | −5.256 | 1.00 | 41.74 | N |
| ATOM | 83 | N3 | G | A | 4 | 19.717 | −3.503 | −3.627 | 1.00 | 27.15 | N |
| ATOM | 84 | C4 | G | A | 4 | 20.621 | −4.492 | −3.442 | 1.00 | 29.75 | C |
| ATOM | 85 | P | T | A | 5 | 17.685 | −5.521 | 2.684 | 1.00 | 50.33 | P |
| ATOM | 86 | O1P | T | A | 5 | 17.240 | −6.864 | 2.218 | 1.00 | 59.78 | O |
| ATOM | 87 | O2P | T | A | 5 | 16.671 | −4.487 | 3.015 | 1.00 | 49.31 | O |
| ATOM | 88 | O5* | T | A | 5 | 18.557 | −5.769 | 4.002 | 1.00 | 54.58 | O |
| ATOM | 89 | C5* | T | A | 5 | 18.881 | −4.680 | 4.865 | 1.00 | 53.03 | C |
| ATOM | 90 | C4* | T | A | 5 | 19.905 | −5.123 | 5.880 | 1.00 | 51.80 | C |
| ATOM | 91 | O4* | T | A | 5 | 21.130 | −5.527 | 5.222 | 1.00 | 43.52 | O |
| ATOM | 92 | C3* | T | A | 5 | 20.298 | −4.067 | 6.908 | 1.00 | 53.68 | C |
| ATOM | 93 | O3* | T | A | 5 | 19.928 | −4.490 | 8.224 | 1.00 | 51.35 | O |
| ATOM | 94 | C2* | T | A | 5 | 21.794 | −3.909 | 6.772 | 1.00 | 50.65 | C |
| ATOM | 95 | C1* | T | A | 5 | 22.223 | −5.176 | 6.060 | 1.00 | 49.79 | C |
| ATOM | 96 | N1 | T | A | 5 | 23.470 | −5.083 | 5.270 | 1.00 | 49.61 | N |
| ATOM | 97 | C2 | T | A | 5 | 24.460 | −5.989 | 5.567 | 1.00 | 53.54 | C |
| ATOM | 98 | O2 | T | A | 5 | 24.323 | −6.831 | 6.437 | 1.00 | 62.28 | O |
| ATOM | 99 | N3 | T | A | 5 | 25.602 | −5.872 | 4.812 | 1.00 | 58.05 | N |
| ATOM | 100 | C4 | T | A | 5 | 25.834 | −4.947 | 3.808 | 1.00 | 57.61 | C |
| ATOM | 101 | O4 | T | A | 5 | 26.908 | −4.958 | 3.213 | 1.00 | 54.13 | O |

TABLE 1-continued

| | | | | | | | | | | | |
|---|---|---|---|---|---|---|---|---|---|---|---|
| ATOM | 102 | C5 | T | A | 5 | 24.748 | −4.029 | 3.554 | 1.00 | 48.45 | C |
| ATOM | 103 | C5M | T | A | 5 | 24.907 | −2.993 | 2.488 | 1.00 | 57.75 | C |
| ATOM | 104 | C6 | T | A | 5 | 23.631 | −4.139 | 4.290 | 1.00 | 48.52 | C |
| ATOM | 105 | P | T | A | 6 | 18.854 | −3.614 | 9.055 | 1.00 | 59.58 | P |
| ATOM | 106 | O1P | T | A | 6 | 18.800 | −4.104 | 10.460 | 1.00 | 68.85 | O |
| ATOM | 107 | O2P | T | A | 6 | 17.575 | −3.543 | 8.299 | 1.00 | 73.87 | O |
| ATOM | 108 | O5* | T | A | 6 | 19.505 | −2.160 | 9.059 | 1.00 | 57.45 | O |
| ATOM | 109 | C5* | T | A | 6 | 19.235 | −1.204 | 10.078 | 1.00 | 54.41 | C |
| ATOM | 110 | C4* | T | A | 6 | 20.472 | −0.396 | 10.369 | 1.00 | 52.42 | C |
| ATOM | 111 | O4* | T | A | 6 | 21.319 | −1.113 | 11.308 | 1.00 | 47.60 | O |
| ATOM | 112 | C3* | T | A | 6 | 21.397 | −0.155 | 9.170 | 1.00 | 51.80 | C |
| ATOM | 113 | O3* | T | A | 6 | 20.956 | 0.970 | 8.405 | 1.00 | 58.34 | O |
| ATOM | 114 | C2* | T | A | 6 | 22.711 | 0.158 | 9.872 | 1.00 | 47.63 | C |
| ATOM | 115 | C1* | T | A | 6 | 22.685 | −0.867 | 11.000 | 1.00 | 47.94 | C |
| ATOM | 116 | N1 | T | A | 6 | 23.366 | −2.146 | 10.671 | 1.00 | 43.12 | N |
| ATOM | 117 | C2 | T | A | 6 | 24.730 | −2.104 | 10.575 | 1.00 | 47.69 | C |
| ATOM | 118 | O2 | T | A | 6 | 25.384 | −1.087 | 10.748 | 1.00 | 56.99 | O |
| ATOM | 119 | N3 | T | A | 6 | 25.303 | −3.310 | 10.270 | 1.00 | 52.12 | N |
| ATOM | 120 | C4 | T | A | 6 | 24.663 | −4.510 | 10.056 | 1.00 | 56.07 | C |
| ATOM | 121 | O4 | T | A | 6 | 25.318 | −5.516 | 9.788 | 1.00 | 83.09 | O |
| ATOM | 122 | C5 | T | A | 6 | 23.224 | −4.471 | 10.174 | 1.00 | 51.70 | C |
| ATOM | 123 | C5M | T | A | 6 | 22.465 | −5.740 | 9.954 | 1.00 | 41.70 | C |
| ATOM | 124 | C6 | T | A | 6 | 22.649 | −3.298 | 10.473 | 1.00 | 51.19 | C |
| ATOM | 125 | P | A | A | 7 | 21.047 | 0.821 | 6.796 | 1.00 | 53.63 | P |
| ATOM | 126 | O1P | A | A | 7 | 20.266 | 1.902 | 6.149 | 1.00 | 58.67 | O |
| ATOM | 127 | O2P | A | A | 7 | 20.738 | −0.601 | 6.446 | 1.00 | 43.11 | O |
| ATOM | 128 | O5* | A | A | 7 | 22.595 | 1.050 | 6.511 | 1.00 | 49.72 | O |
| ATOM | 129 | C5* | A | A | 7 | 23.148 | 2.353 | 6.333 | 1.00 | 50.48 | C |
| ATOM | 130 | C4* | A | A | 7 | 24.365 | 2.282 | 5.448 | 1.00 | 42.81 | C |
| ATOM | 131 | O4* | A | A | 7 | 25.350 | 1.378 | 5.991 | 1.00 | 42.26 | O |
| ATOM | 132 | C3* | A | A | 7 | 24.111 | 1.789 | 4.017 | 1.00 | 37.16 | C |
| ATOM | 133 | O3* | A | A | 7 | 25.005 | 2.529 | 3.165 | 1.00 | 40.32 | O |
| ATOM | 134 | C2* | A | A | 7 | 24.498 | 0.326 | 4.067 | 1.00 | 33.68 | C |
| ATOM | 135 | C1* | A | A | 7 | 25.601 | 0.299 | 5.100 | 1.00 | 37.44 | C |
| ATOM | 136 | N9 | A | A | 7 | 25.663 | −0.995 | 5.805 | 1.00 | 34.90 | N |
| ATOM | 137 | C8 | A | A | 7 | 24.765 | −1.589 | 6.654 | 1.00 | 30.92 | C |
| ATOM | 138 | N7 | A | A | 7 | 25.157 | −2.761 | 7.105 | 1.00 | 34.81 | N |
| ATOM | 139 | C5 | A | A | 7 | 26.400 | −2.946 | 6.512 | 1.00 | 37.70 | C |
| ATOM | 140 | C6 | A | A | 7 | 27.338 | −3.991 | 6.582 | 1.00 | 38.20 | C |
| ATOM | 141 | N6 | A | A | 7 | 27.169 | −5.095 | 7.309 | 1.00 | 48.22 | N |
| ATOM | 142 | N1 | A | A | 7 | 28.474 | −3.862 | 5.867 | 1.00 | 39.34 | N |
| ATOM | 143 | C2 | A | A | 7 | 28.650 | −2.758 | 5.135 | 1.00 | 40.14 | C |
| ATOM | 144 | N3 | A | A | 7 | 27.844 | −1.709 | 4.986 | 1.00 | 42.65 | N |
| ATOM | 145 | C4 | A | A | 7 | 26.723 | −1.866 | 5.710 | 1.00 | 36.25 | C |
| ATOM | 146 | P | G | A | 8 | 24.666 | 4.111 | 3.012 | 1.00 | 48.55 | P |
| ATOM | 147 | O1P | G | A | 8 | 25.848 | 4.938 | 3.355 | 1.00 | 65.47 | O |
| ATOM | 148 | O2P | G | A | 8 | 23.347 | 4.388 | 3.636 | 1.00 | 44.00 | O |
| ATOM | 149 | O5* | G | A | 8 | 24.465 | 4.233 | 1.428 | 1.00 | 50.49 | O |
| ATOM | 150 | C5* | G | A | 8 | 23.925 | 3.104 | 0.737 | 1.00 | 41.02 | C |
| ATOM | 151 | C4* | G | A | 8 | 23.223 | 3.627 | −0.493 | 1.00 | 42.14 | C |
| ATOM | 152 | O4* | G | A | 8 | 24.102 | 3.539 | −1.629 | 1.00 | 36.17 | O |
| ATOM | 153 | C3* | G | A | 8 | 21.934 | 2.903 | −0.861 | 1.00 | 40.01 | C |
| ATOM | 154 | O3* | G | A | 8 | 20.913 | 3.886 | −1.056 | 1.00 | 41.46 | O |
| ATOM | 155 | C2* | G | A | 8 | 22.252 | 2.181 | −2.151 | 1.00 | 32.67 | C |
| ATOM | 156 | C1* | G | A | 8 | 23.429 | 2.944 | −2.729 | 1.00 | 37.41 | C |
| ATOM | 157 | N9 | G | A | 8 | 24.319 | 2.019 | −3.471 | 1.00 | 36.75 | N |
| ATOM | 158 | C8 | G | A | 8 | 25.185 | 1.073 | −2.976 | 1.00 | 33.56 | C |
| ATOM | 159 | N7 | G | A | 8 | 25.814 | 0.435 | −3.923 | 1.00 | 30.86 | N |
| ATOM | 160 | C5 | G | A | 8 | 25.334 | 0.994 | −5.098 | 1.00 | 27.85 | C |
| ATOM | 161 | C6 | G | A | 8 | 25.650 | 0.707 | −6.452 | 1.00 | 24.50 | C |
| ATOM | 162 | O6 | G | A | 8 | 26.452 | −0.136 | −6.869 | 1.00 | 26.69 | O |
| ATOM | 163 | N1 | G | A | 8 | 24.934 | 1.506 | −7.335 | 1.00 | 26.59 | N |
| ATOM | 164 | C2 | G | A | 8 | 24.023 | 2.468 | −6.970 | 1.00 | 35.09 | C |
| ATOM | 165 | N2 | G | A | 8 | 23.431 | 3.141 | −7.973 | 1.00 | 24.01 | N |
| ATOM | 166 | N3 | G | A | 8 | 23.722 | 2.743 | −5.710 | 1.00 | 33.73 | N |
| ATOM | 167 | C4 | G | A | 8 | 24.404 | 1.980 | −4.834 | 1.00 | 31.59 | C |
| ATOM | 168 | P | G | A | 9 | 19.377 | 3.501 | −0.825 | 1.00 | 48.50 | P |
| ATOM | 169 | O1P | G | A | 9 | 18.672 | 4.669 | −0.225 | 1.00 | 53.53 | O |
| ATOM | 170 | O2P | G | A | 9 | 19.245 | 2.168 | −0.188 | 1.00 | 54.48 | O |
| ATOM | 171 | O5* | G | A | 9 | 18.839 | 3.362 | −2.337 | 1.00 | 43.91 | O |
| ATOM | 172 | C5* | G | A | 9 | 18.822 | 4.563 | −3.115 | 1.00 | 47.62 | C |
| ATOM | 173 | C4* | G | A | 9 | 18.410 | 4.210 | −4.527 | 1.00 | 47.23 | C |
| ATOM | 174 | O4* | G | A | 9 | 19.548 | 3.632 | −5.211 | 1.00 | 45.95 | O |
| ATOM | 175 | C3* | G | A | 9 | 17.283 | 3.178 | −4.602 | 1.00 | 44.88 | C |
| ATOM | 176 | O3* | G | A | 9 | 16.267 | 3.655 | −5.481 | 1.00 | 40.26 | O |
| ATOM | 177 | C2* | G | A | 9 | 17.941 | 1.929 | −5.140 | 1.00 | 34.65 | C |
| ATOM | 178 | C1* | G | A | 9 | 19.139 | 2.467 | −5.907 | 1.00 | 30.64 | C |
| ATOM | 179 | N9 | G | A | 9 | 20.201 | 1.441 | −5.971 | 1.00 | 31.33 | N |
| ATOM | 180 | C8 | G | A | 9 | 20.821 | 0.754 | −4.961 | 1.00 | 28.87 | C |

TABLE 1-continued

| ATOM | 181 | N7 | G | A | 9 | 21.722 | -0.088 | -5.394 | 1.00 | 33.07 | N |
| --- | --- | --- | --- | --- | --- | --- | --- | --- | --- | --- | --- |
| ATOM | 182 | C5 | G | A | 9 | 21.689 | 0.058 | -6.777 | 1.00 | 36.74 | C |
| ATOM | 183 | C6 | G | A | 9 | 22.435 | -0.586 | -7.795 | 1.00 | 33.02 | C |
| ATOM | 184 | O6 | G | A | 9 | 23.317 | -1.454 | -7.669 | 1.00 | 32.22 | O |
| ATOM | 185 | N1 | G | A | 9 | 22.077 | -0.133 | -9.066 | 1.00 | 27.89 | N |
| ATOM | 186 | C2 | G | A | 9 | 21.124 | 0.816 | -9.336 | 1.00 | 27.77 | C |
| ATOM | 187 | N2 | G | A | 9 | 20.927 | 1.114 | -10.632 | 1.00 | 34.25 | N |
| ATOM | 188 | N3 | G | A | 9 | 20.424 | 1.420 | -8.397 | 1.00 | 28.22 | N |
| ATOM | 189 | C4 | G | A | 9 | 20.752 | 1.001 | -7.153 | 1.00 | 37.67 | C |
| ATOM | 190 | P | G | A | 10 | 14.865 | 2.902 | -5.673 | 1.00 | 40.79 | P |
| ATOM | 191 | O1P | G | A | 10 | 13.798 | 3.952 | -5.668 | 1.00 | 53.35 | O |
| ATOM | 192 | O2P | G | A | 10 | 14.747 | 1.711 | -4.803 | 1.00 | 33.42 | O |
| ATOM | 193 | O5* | G | A | 10 | 14.958 | 2.364 | -7.180 | 1.00 | 41.05 | O |
| ATOM | 194 | C5* | G | A | 10 | 15.368 | 3.316 | -8.173 | 1.00 | 33.17 | C |
| ATOM | 195 | C4* | G | A | 10 | 15.181 | 2.681 | -9.532 | 1.00 | 39.57 | C |
| ATOM | 196 | O4* | G | A | 10 | 16.371 | 1.938 | -9.876 | 1.00 | 42.79 | O |
| ATOM | 197 | C3* | G | A | 10 | 14.025 | 1.686 | -9.620 | 1.00 | 43.29 | C |
| ATOM | 198 | O3* | G | A | 10 | 13.401 | 1.810 | -10.903 | 1.00 | 59.92 | O |
| ATOM | 199 | C2* | G | A | 10 | 14.698 | 0.340 | -9.448 | 1.00 | 32.10 | C |
| ATOM | 200 | C1* | G | A | 10 | 16.076 | 0.553 | -10.014 | 1.00 | 35.74 | C |
| ATOM | 201 | N9 | G | A | 10 | 17.094 | -0.279 | -9.340 | 1.00 | 27.80 | N |
| ATOM | 202 | C8 | G | A | 10 | 17.343 | -0.451 | -7.996 | 1.00 | 28.93 | C |
| ATOM | 203 | N7 | G | A | 10 | 18.327 | -1.266 | -7.762 | 1.00 | 31.90 | N |
| ATOM | 204 | C5 | G | A | 10 | 18.762 | -1.660 | -9.029 | 1.00 | 33.95 | C |
| ATOM | 205 | C6 | G | A | 10 | 19.799 | -2.534 | -9.435 | 1.00 | 32.82 | C |
| ATOM | 206 | O6 | G | A | 10 | 20.590 | -3.176 | -8.726 | 1.00 | 34.20 | O |
| ATOM | 207 | N1 | G | A | 10 | 19.889 | -2.645 | -10.826 | 1.00 | 33.11 | N |
| ATOM | 208 | C2 | G | A | 10 | 19.070 | -1.985 | -11.713 | 1.00 | 34.25 | C |
| ATOM | 209 | N2 | G | A | 10 | 19.270 | -2.186 | -13.024 | 1.00 | 30.42 | N |
| ATOM | 210 | N3 | G | A | 10 | 18.101 | -1.168 | -11.345 | 1.00 | 30.00 | N |
| ATOM | 211 | C4 | G | A | 10 | 18.004 | -1.053 | -10.008 | 1.00 | 26.02 | C |
| ATOM | 212 | P | T | A | 11 | 11.800 | 1.963 | -11.025 | 1.00 | 64.48 | P |
| ATOM | 213 | O1P | T | A | 11 | 11.149 | 1.059 | -10.025 | 1.00 | 59.02 | O |
| ATOM | 214 | O2P | T | A | 11 | 11.409 | 1.848 | -12.455 | 1.00 | 46.81 | O |
| ATOM | 215 | O5* | T | A | 11 | 11.475 | 3.446 | -10.542 | 1.00 | 49.63 | O |
| ATOM | 216 | C5* | T | A | 11 | 11.693 | 4.597 | -11.345 | 1.00 | 49.13 | C |
| ATOM | 217 | C4* | T | A | 11 | 11.494 | 5.848 | -10.524 | 1.00 | 53.87 | C |
| ATOM | 218 | O4* | T | A | 11 | 12.355 | 5.829 | -9.363 | 1.00 | 55.43 | O |
| ATOM | 219 | C3* | T | A | 11 | 11.785 | 7.158 | -11.248 | 1.00 | 50.42 | C |
| ATOM | 220 | O3* | T | A | 11 | 10.628 | 8.004 | -11.205 | 1.00 | 53.81 | O |
| ATOM | 221 | C2* | T | A | 11 | 12.937 | 7.787 | -10.500 | 1.00 | 44.81 | C |
| ATOM | 222 | C1* | T | A | 11 | 12.836 | 7.151 | -9.125 | 1.00 | 47.63 | C |
| ATOM | 223 | N1 | T | A | 11 | 14.113 | 7.085 | -8.373 | 1.00 | 53.03 | N |
| ATOM | 224 | C2 | T | A | 11 | 14.039 | 7.292 | -7.017 | 1.00 | 51.29 | C |
| ATOM | 225 | O2 | T | A | 11 | 12.988 | 7.521 | -6.448 | 1.00 | 54.27 | O |
| ATOM | 226 | N3 | T | A | 11 | 15.247 | 7.220 | -6.366 | 1.00 | 48.05 | N |
| ATOM | 227 | C4 | T | A | 11 | 16.476 | 6.966 | -6.942 | 1.00 | 51.62 | C |
| ATOM | 228 | O4 | T | A | 11 | 17.485 | 6.929 | -6.240 | 1.00 | 68.78 | O |
| ATOM | 229 | C5 | T | A | 11 | 16.472 | 6.758 | -8.372 | 1.00 | 55.76 | C |
| ATOM | 230 | C5M | T | A | 11 | 17.774 | 6.477 | -9.061 | 1.00 | 48.93 | C |
| ATOM | 231 | C6 | T | A | 11 | 15.298 | 6.826 | -9.019 | 1.00 | 51.26 | C |
| ATOM | 232 | P | T | A | 12 | 9.858 | 8.254 | -12.602 | 1.00 | 59.11 | P |
| ATOM | 233 | O1P | T | A | 12 | 8.736 | 9.208 | -12.400 | 1.00 | 77.27 | O |
| ATOM | 234 | O2P | T | A | 12 | 9.572 | 6.941 | -13.244 | 1.00 | 63.56 | O |
| ATOM | 235 | O5* | T | A | 12 | 10.972 | 8.985 | -13.478 | 1.00 | 51.87 | O |
| ATOM | 236 | C5* | T | A | 12 | 10.613 | 10.039 | -14.373 | 1.00 | 45.06 | C |
| ATOM | 237 | C4* | T | A | 12 | 11.804 | 10.967 | -14.504 | 1.00 | 48.60 | C |
| ATOM | 238 | O4* | T | A | 12 | 11.621 | 12.089 | -13.607 | 1.00 | 47.77 | O |
| ATOM | 239 | C3* | T | A | 12 | 13.122 | 10.325 | -14.052 | 1.00 | 51.66 | C |
| ATOM | 240 | O3* | T | A | 12 | 13.772 | 9.700 | -15.165 | 1.00 | 54.40 | O |
| ATOM | 241 | C2* | T | A | 12 | 13.916 | 11.505 | -13.536 | 1.00 | 43.93 | C |
| ATOM | 242 | C1* | T | A | 12 | 12.852 | 12.434 | -12.992 | 1.00 | 43.83 | C |
| ATOM | 243 | N1 | T | A | 12 | 12.704 | 12.437 | -11.517 | 1.00 | 38.64 | N |
| ATOM | 244 | C2 | T | A | 12 | 13.696 | 13.054 | -10.797 | 1.00 | 38.42 | C |
| ATOM | 245 | O2 | T | A | 12 | 14.657 | 13.578 | -11.339 | 1.00 | 43.58 | O |
| ATOM | 246 | N3 | T | A | 12 | 13.514 | 13.029 | -9.433 | 1.00 | 31.38 | N |
| ATOM | 247 | C4 | T | A | 12 | 12.452 | 12.454 | -8.760 | 1.00 | 40.08 | C |
| ATOM | 248 | O4 | T | A | 12 | 12.391 | 12.493 | -7.530 | 1.00 | 51.38 | O |
| ATOM | 249 | C5 | T | A | 12 | 11.449 | 11.824 | -9.589 | 1.00 | 39.98 | C |
| ATOM | 250 | C5M | T | A | 12 | 10.271 | 11.183 | -8.921 | 1.00 | 41.25 | C |
| ATOM | 251 | C6 | T | A | 12 | 11.619 | 11.843 | -10.917 | 1.00 | 38.35 | C |
| ATOM | 252 | P | A | A | 13 | 14.709 | 8.420 | -14.874 | 1.00 | 56.40 | P |
| ATOM | 253 | O1P | A | A | 13 | 15.245 | 7.891 | -16.158 | 1.00 | 83.43 | O |
| ATOM | 254 | O2P | A | A | 13 | 14.010 | 7.477 | -13.952 | 1.00 | 47.62 | O |
| ATOM | 255 | O5* | A | A | 13 | 15.933 | 9.019 | -14.044 | 1.00 | 49.69 | O |
| ATOM | 256 | C5* | A | A | 13 | 16.952 | 9.780 | -14.693 | 1.00 | 48.60 | C |
| ATOM | 257 | C4* | A | A | 13 | 18.015 | 10.148 | -13.686 | 1.00 | 46.75 | C |
| ATOM | 258 | O4* | A | A | 13 | 17.412 | 10.788 | -12.544 | 1.00 | 43.17 | O |
| ATOM | 259 | C3* | A | A | 13 | 18.841 | 8.988 | -13.132 | 1.00 | 48.58 | C |

TABLE 1-continued

| | | | | | | | | | | | |
|---|---|---|---|---|---|---|---|---|---|---|---|
| ATOM | 260 | O3* | A | A | 13 | 20.223 | 9.383 | −13.205 | 1.00 | 56.09 | O |
| ATOM | 261 | C2* | A | A | 13 | 18.390 | 8.842 | −11.692 | 1.00 | 42.88 | C |
| ATOM | 262 | C1* | A | A | 13 | 17.918 | 10.228 | −11.329 | 1.00 | 37.14 | C |
| ATOM | 263 | N9 | A | A | 13 | 16.876 | 10.213 | −10.284 | 1.00 | 31.45 | N |
| ATOM | 264 | C8 | A | A | 13 | 15.506 | 10.203 | −10.443 | 1.00 | 36.72 | C |
| ATOM | 265 | N7 | A | A | 13 | 14.835 | 10.194 | −9.322 | 1.00 | 41.36 | N |
| ATOM | 266 | C5 | A | A | 13 | 15.837 | 10.202 | −8.358 | 1.00 | 43.72 | C |
| ATOM | 267 | C6 | A | A | 13 | 15.742 | 10.199 | −6.955 | 1.00 | 47.43 | C |
| ATOM | 268 | N6 | A | A | 13 | 14.571 | 10.186 | −6.313 | 1.00 | 47.62 | N |
| ATOM | 269 | N1 | A | A | 13 | 16.894 | 10.209 | −6.255 | 1.00 | 45.39 | N |
| ATOM | 270 | C2 | A | A | 13 | 18.044 | 10.220 | −6.944 | 1.00 | 45.97 | C |
| ATOM | 271 | N3 | A | A | 13 | 18.256 | 10.225 | −8.257 | 1.00 | 52.64 | N |
| ATOM | 272 | C4 | A | A | 13 | 17.095 | 10.215 | −8.940 | 1.00 | 40.69 | C |
| ATOM | 273 | P | G | A | 14 | 20.936 | 9.348 | −14.655 | 1.00 | 61.41 | P |
| ATOM | 274 | O1P | G | A | 14 | 22.349 | 9.797 | −14.548 | 1.00 | 64.12 | O |
| ATOM | 275 | O2P | G | A | 14 | 20.065 | 9.963 | −15.691 | 1.00 | 79.01 | O |
| ATOM | 276 | O5* | G | A | 14 | 20.949 | 7.773 | −14.945 | 1.00 | 61.34 | O |
| ATOM | 277 | C5* | G | A | 14 | 21.778 | 6.942 | −14.124 | 1.00 | 53.68 | C |
| ATOM | 278 | C4* | G | A | 14 | 22.257 | 5.804 | −14.997 | 1.00 | 49.91 | C |
| ATOM | 279 | O4* | G | A | 14 | 23.343 | 5.109 | −14.358 | 1.00 | 35.96 | O |
| ATOM | 280 | C3* | G | A | 14 | 21.177 | 4.758 | −15.280 | 1.00 | 43.38 | C |
| ATOM | 281 | O3* | G | A | 14 | 21.299 | 4.353 | −16.650 | 1.00 | 37.90 | O |
| ATOM | 282 | C2* | G | A | 14 | 21.521 | 3.626 | −14.329 | 1.00 | 32.91 | C |
| ATOM | 283 | C1* | G | A | 14 | 23.022 | 3.732 | −14.202 | 1.00 | 32.67 | C |
| ATOM | 284 | N9 | G | A | 14 | 23.493 | 3.194 | −12.909 | 1.00 | 32.48 | N |
| ATOM | 285 | C8 | G | A | 14 | 23.180 | 3.552 | −11.626 | 1.00 | 33.97 | C |
| ATOM | 286 | N7 | G | A | 14 | 23.808 | 2.835 | −10.725 | 1.00 | 25.96 | N |
| ATOM | 287 | C5 | G | A | 14 | 24.578 | 1.955 | −11.461 | 1.00 | 21.06 | C |
| ATOM | 288 | C6 | G | A | 14 | 25.466 | 0.942 | −11.034 | 1.00 | 34.00 | C |
| ATOM | 289 | O6 | G | A | 14 | 25.764 | 0.603 | −9.873 | 1.00 | 37.53 | O |
| ATOM | 290 | N1 | G | A | 14 | 26.034 | 0.295 | −12.125 | 1.00 | 29.46 | N |
| ATOM | 291 | C2 | G | A | 14 | 25.784 | 0.580 | −13.446 | 1.00 | 36.08 | C |
| ATOM | 292 | N2 | G | A | 14 | 26.449 | −0.179 | −14.326 | 1.00 | 23.11 | N |
| ATOM | 293 | N3 | G | A | 14 | 24.955 | 1.525 | −13.871 | 1.00 | 28.67 | N |
| ATOM | 294 | C4 | G | A | 14 | 24.397 | 2.162 | −12.812 | 1.00 | 33.22 | C |
| ATOM | 295 | P | G | A | 15 | 20.037 | 3.621 | −17.320 | 1.00 | 47.53 | P |
| ATOM | 296 | O1P | G | A | 15 | 19.756 | 4.234 | −18.649 | 1.00 | 58.24 | O |
| ATOM | 297 | O2P | G | A | 15 | 18.938 | 3.474 | −16.333 | 1.00 | 42.35 | O |
| ATOM | 298 | O5* | G | A | 15 | 20.571 | 2.141 | −17.587 | 1.00 | 54.49 | O |
| ATOM | 299 | C5* | G | A | 15 | 21.823 | 1.895 | −18.226 | 1.00 | 49.24 | C |
| ATOM | 300 | C4* | G | A | 15 | 22.021 | 0.392 | −18.263 | 1.00 | 43.24 | C |
| ATOM | 301 | O4* | G | A | 15 | 22.797 | −0.010 | −17.116 | 1.00 | 39.75 | O |
| ATOM | 302 | C3* | G | A | 15 | 20.717 | −0.410 | −18.215 | 1.00 | 39.17 | C |
| ATOM | 303 | O3* | G | A | 15 | 20.851 | −1.382 | −19.285 | 1.00 | 35.38 | O |
| ATOM | 304 | C2* | G | A | 15 | 20.697 | −1.012 | −16.829 | 1.00 | 40.76 | C |
| ATOM | 305 | C1* | G | A | 15 | 22.161 | −1.084 | −16.436 | 1.00 | 37.50 | C |
| ATOM | 306 | N9 | G | A | 15 | 22.309 | −0.974 | −14.968 | 1.00 | 34.05 | N |
| ATOM | 307 | C8 | G | A | 15 | 21.710 | −0.104 | −14.091 | 1.00 | 27.76 | C |
| ATOM | 308 | N7 | G | A | 15 | 22.075 | −0.290 | −12.851 | 1.00 | 31.42 | N |
| ATOM | 309 | C5 | G | A | 15 | 22.972 | −1.350 | −12.917 | 1.00 | 22.80 | C |
| ATOM | 310 | C6 | G | A | 15 | 23.692 | −1.990 | −11.878 | 1.00 | 26.23 | C |
| ATOM | 311 | O6 | G | A | 15 | 23.675 | −1.735 | −10.663 | 1.00 | 26.66 | O |
| ATOM | 312 | N1 | G | A | 15 | 24.490 | −3.016 | −12.362 | 1.00 | 23.65 | N |
| ATOM | 313 | C2 | G | A | 15 | 24.579 | −3.376 | −13.690 | 1.00 | 25.58 | C |
| ATOM | 314 | N2 | G | A | 15 | 25.410 | −4.398 | −13.953 | 1.00 | 24.66 | N |
| ATOM | 315 | N3 | G | A | 15 | 23.911 | −2.785 | −14.664 | 1.00 | 25.84 | N |
| ATOM | 316 | C4 | G | A | 15 | 23.126 | −1.782 | −14.218 | 1.00 | 30.68 | C |
| ATOM | 317 | P | G | A | 16 | 19.796 | −2.590 | −19.621 | 1.00 | 39.43 | P |
| ATOM | 318 | O1P | G | A | 16 | 19.833 | −2.799 | −21.111 | 1.00 | 56.58 | O |
| ATOM | 319 | O2P | G | A | 16 | 18.460 | −2.489 | −18.997 | 1.00 | 47.75 | O |
| ATOM | 320 | O5* | G | A | 16 | 20.546 | −3.876 | −19.022 | 1.00 | 40.31 | O |
| ATOM | 321 | C5* | G | A | 16 | 21.810 | −4.254 | −19.569 | 1.00 | 39.13 | C |
| ATOM | 322 | C4* | G | A | 16 | 22.125 | −5.664 | −19.131 | 1.00 | 37.82 | C |
| ATOM | 323 | O4* | G | A | 16 | 22.616 | −5.664 | −17.773 | 1.00 | 32.40 | O |
| ATOM | 324 | C3* | G | A | 16 | 20.909 | −6.601 | −19.131 | 1.00 | 34.29 | C |
| ATOM | 325 | O3* | G | A | 16 | 21.378 | −7.909 | −19.462 | 1.00 | 40.26 | O |
| ATOM | 326 | C2* | G | A | 16 | 20.447 | −6.551 | −17.684 | 1.00 | 32.52 | C |
| ATOM | 327 | C1* | G | A | 16 | 21.761 | −6.437 | −16.930 | 1.00 | 30.85 | C |
| ATOM | 328 | N9 | G | A | 16 | 21.553 | −5.765 | −15.628 | 1.00 | 34.38 | N |
| ATOM | 329 | C8 | G | A | 16 | 20.796 | −4.659 | −15.332 | 1.00 | 32.09 | C |
| ATOM | 330 | N7 | G | A | 16 | 20.845 | −4.342 | −14.069 | 1.00 | 31.68 | N |
| ATOM | 331 | C5 | G | A | 16 | 21.683 | −5.290 | −13.498 | 1.00 | 29.79 | C |
| ATOM | 332 | C6 | G | A | 16 | 22.102 | −5.442 | −12.148 | 1.00 | 34.25 | C |
| ATOM | 333 | O6 | G | A | 16 | 21.785 | −4.725 | −11.188 | 1.00 | 32.33 | O |
| ATOM | 334 | N1 | G | A | 16 | 22.951 | −6.527 | −11.981 | 1.00 | 31.40 | N |
| ATOM | 335 | C2 | G | A | 16 | 23.342 | −7.363 | −13.008 | 1.00 | 37.34 | C |
| ATOM | 336 | N2 | G | A | 16 | 24.169 | −8.370 | −12.677 | 1.00 | 25.98 | N |
| ATOM | 337 | N3 | G | A | 16 | 22.957 | −7.229 | −14.266 | 1.00 | 26.35 | N |
| ATOM | 338 | C4 | G | A | 16 | 22.131 | −6.181 | −14.453 | 1.00 | 28.66 | C |

TABLE 1-continued

| | | | | | | | | | | | |
|---|---|---|---|---|---|---|---|---|---|---|---|
| ATOM | 339 | P | T | A | 17 | 20.537 | −8.872 | −20.441 | 1.00 | 45.61 | P |
| ATOM | 340 | O1P | T | A | 17 | 19.135 | −8.928 | −19.953 | 1.00 | 46.60 | O |
| ATOM | 341 | O2P | T | A | 17 | 21.331 | −10.120 | −20.630 | 1.00 | 38.82 | O |
| ATOM | 342 | O5* | T | A | 17 | 20.533 | −8.107 | −21.842 | 1.00 | 53.16 | O |
| ATOM | 343 | C5* | T | A | 17 | 21.751 | −7.861 | −22.548 | 1.00 | 57.18 | C |
| ATOM | 344 | C4* | T | A | 17 | 21.474 | −7.047 | −23.785 | 1.00 | 59.32 | C |
| ATOM | 345 | O4* | T | A | 17 | 21.187 | −5.674 | −23.443 | 1.00 | 63.21 | O |
| ATOM | 346 | C3* | T | A | 17 | 22.600 | −7.004 | −24.817 | 1.00 | 52.76 | C |
| ATOM | 347 | O3* | T | A | 17 | 22.039 | −7.118 | −26.131 | 1.00 | 63.57 | O |
| ATOM | 348 | C2* | T | A | 17 | 23.212 | −5.630 | −24.626 | 1.00 | 54.87 | C |
| ATOM | 349 | C1* | T | A | 17 | 22.010 | −4.802 | −24.208 | 1.00 | 55.12 | C |
| ATOM | 350 | N1 | T | A | 17 | 22.330 | −3.589 | −23.415 | 1.00 | 47.62 | N |
| ATOM | 351 | C2 | T | A | 17 | 21.598 | −2.463 | −23.681 | 1.00 | 44.20 | C |
| ATOM | 352 | O2 | T | A | 17 | 20.713 | −2.396 | −24.518 | 1.00 | 52.81 | O |
| ATOM | 353 | N3 | T | A | 17 | 21.940 | −1.375 | −22.916 | 1.00 | 49.25 | N |
| ATOM | 354 | C4 | T | A | 17 | 22.917 | −1.323 | −21.941 | 1.00 | 44.58 | C |
| ATOM | 355 | O4 | T | A | 17 | 23.095 | −0.266 | −21.347 | 1.00 | 50.74 | O |
| ATOM | 356 | C5 | T | A | 17 | 23.644 | −2.548 | −21.718 | 1.00 | 41.54 | C |
| ATOM | 357 | C5M | T | A | 17 | 24.719 | −2.576 | −20.679 | 1.00 | 34.22 | C |
| ATOM | 358 | C6 | T | A | 17 | 23.321 | −3.618 | −22.460 | 1.00 | 45.24 | C |
| ATOM | 359 | P | T | A | 18 | 22.545 | −8.284 | −27.119 | 1.00 | 64.00 | P |
| ATOM | 360 | O1P | T | A | 18 | 21.556 | −8.463 | −28.219 | 1.00 | 93.83 | O |
| ATOM | 361 | O2P | T | A | 18 | 22.988 | −9.475 | −26.349 | 1.00 | 61.72 | O |
| ATOM | 362 | O5* | T | A | 18 | 23.850 | −7.623 | −27.765 | 1.00 | 56.97 | O |
| ATOM | 363 | C5* | T | A | 18 | 24.946 | −8.458 | −28.140 | 1.00 | 50.92 | C |
| ATOM | 364 | C4* | T | A | 18 | 26.186 | −7.602 | −28.255 | 1.00 | 48.31 | C |
| ATOM | 365 | O4* | T | A | 18 | 25.960 | −6.554 | −29.231 | 1.00 | 46.73 | O |
| ATOM | 366 | C3* | T | A | 18 | 26.539 | −6.833 | −26.968 | 1.00 | 45.99 | C |
| ATOM | 367 | O3* | T | A | 18 | 27.315 | −7.676 | −26.117 | 1.00 | 56.64 | O |
| ATOM | 368 | C2* | T | A | 18 | 27.362 | −5.691 | −27.535 | 1.00 | 42.77 | C |
| ATOM | 369 | C1* | T | A | 18 | 26.592 | −5.352 | −28.802 | 1.00 | 41.34 | C |
| ATOM | 370 | N1 | T | A | 18 | 25.563 | −4.293 | −28.630 | 1.00 | 32.25 | N |
| ATOM | 371 | C2 | T | A | 18 | 26.001 | −3.000 | −28.628 | 1.00 | 38.00 | C |
| ATOM | 372 | O2 | T | A | 18 | 27.170 | −2.682 | −28.758 | 1.00 | 39.94 | O |
| ATOM | 373 | N3 | T | A | 18 | 24.999 | −2.074 | −28.469 | 1.00 | 37.83 | N |
| ATOM | 374 | C4 | T | A | 18 | 23.653 | −2.329 | −28.315 | 1.00 | 35.30 | C |
| ATOM | 375 | O4 | T | A | 18 | 22.858 | −1.399 | −28.179 | 1.00 | 38.51 | O |
| ATOM | 376 | C5 | T | A | 18 | 23.273 | −3.720 | −28.329 | 1.00 | 37.80 | C |
| ATOM | 377 | C5M | T | A | 18 | 21.827 | −4.062 | −28.167 | 1.00 | 48.66 | C |
| ATOM | 378 | C6 | T | A | 18 | 24.238 | −4.632 | −28.486 | 1.00 | 38.17 | C |
| ATOM | 379 | P | A | A | 19 | 27.624 | −7.305 | −24.584 | 1.00 | 60.36 | P |
| ATOM | 380 | O1P | A | A | 19 | 28.906 | −7.957 | −24.178 | 1.00 | 66.82 | O |
| ATOM | 381 | O2P | A | A | 19 | 26.442 | −7.524 | −23.718 | 1.00 | 38.56 | O |
| ATOM | 382 | O5* | A | A | 19 | 27.910 | −5.735 | −24.679 | 1.00 | 53.15 | O |
| ATOM | 383 | C5* | A | A | 19 | 29.268 | −5.318 | −24.871 | 1.00 | 53.63 | C |
| ATOM | 384 | C4* | A | A | 19 | 29.566 | −4.194 | −23.905 | 1.00 | 54.43 | C |
| ATOM | 385 | O4* | A | A | 19 | 28.876 | −3.002 | −24.345 | 1.00 | 50.35 | O |
| ATOM | 386 | C3* | A | A | 19 | 29.075 | −4.446 | −22.474 | 1.00 | 54.73 | C |
| ATOM | 387 | O3* | A | A | 19 | 29.991 | −3.802 | −21.576 | 1.00 | 57.17 | O |
| ATOM | 388 | C2* | A | A | 19 | 27.719 | −3.773 | −22.434 | 1.00 | 44.24 | C |
| ATOM | 389 | C1* | A | A | 19 | 27.873 | −2.627 | −23.411 | 1.00 | 45.19 | C |
| ATOM | 390 | N9 | A | A | 19 | 26.591 | −2.318 | −24.075 | 1.00 | 43.52 | N |
| ATOM | 391 | C8 | A | A | 19 | 25.768 | −3.128 | −24.816 | 1.00 | 44.82 | C |
| ATOM | 392 | N7 | A | A | 19 | 24.698 | −2.513 | −25.261 | 1.00 | 47.52 | N |
| ATOM | 393 | C5 | A | A | 19 | 24.833 | −1.218 | −24.779 | 1.00 | 43.52 | C |
| ATOM | 394 | C6 | A | A | 19 | 24.025 | −0.077 | −24.905 | 1.00 | 40.95 | C |
| ATOM | 395 | N6 | A | A | 19 | 22.877 | −0.077 | −25.586 | 1.00 | 58.41 | N |
| ATOM | 396 | N1 | A | A | 19 | 24.440 | 1.061 | −24.306 | 1.00 | 37.32 | N |
| ATOM | 397 | C2 | A | A | 19 | 25.594 | 1.048 | −23.625 | 1.00 | 40.59 | C |
| ATOM | 398 | N3 | A | A | 19 | 26.440 | 0.036 | −23.436 | 1.00 | 44.61 | N |
| ATOM | 399 | C4 | A | A | 19 | 25.998 | −1.080 | −24.045 | 1.00 | 43.65 | C |
| ATOM | 400 | P | G | A | 20 | 31.242 | −4.650 | −21.011 | 1.00 | 51.34 | P |
| ATOM | 401 | O1P | G | A | 20 | 32.362 | −3.722 | −20.703 | 1.00 | 55.00 | O |
| ATOM | 402 | O2P | G | A | 20 | 31.518 | −5.835 | −21.865 | 1.00 | 47.58 | O |
| ATOM | 403 | O5* | G | A | 20 | 30.636 | −5.207 | −19.638 | 1.00 | 48.69 | O |
| ATOM | 404 | C5* | G | A | 20 | 30.626 | −4.403 | −18.456 | 1.00 | 41.81 | C |
| ATOM | 405 | C4* | G | A | 20 | 30.983 | −5.293 | −17.288 | 1.00 | 42.46 | C |
| ATOM | 406 | O4* | G | A | 20 | 31.025 | −4.529 | −16.070 | 1.00 | 37.30 | O |
| ATOM | 407 | C3* | G | A | 20 | 30.014 | −6.450 | −17.049 | 1.00 | 43.59 | C |
| ATOM | 408 | O3* | G | A | 20 | 30.771 | −7.646 | −16.839 | 1.00 | 45.80 | O |
| ATOM | 409 | C2* | G | A | 20 | 29.255 | −6.052 | −15.804 | 1.00 | 36.16 | C |
| ATOM | 410 | C1* | G | A | 20 | 30.213 | −5.130 | −15.073 | 1.00 | 31.39 | C |
| ATOM | 411 | N9 | G | A | 20 | 29.462 | −4.118 | −14.294 | 1.00 | 26.89 | N |
| ATOM | 412 | C8 | G | A | 20 | 28.676 | −3.085 | −14.738 | 1.00 | 31.65 | C |
| ATOM | 413 | N7 | G | A | 20 | 28.164 | −2.384 | −13.762 | 1.00 | 32.84 | N |
| ATOM | 414 | C5 | G | A | 20 | 28.646 | −2.998 | −12.610 | 1.00 | 28.59 | C |
| ATOM | 415 | C6 | G | A | 20 | 28.421 | −2.671 | −11.246 | 1.00 | 21.15 | C |
| ATOM | 416 | O6 | G | A | 20 | 27.728 | −1.741 | −10.809 | 1.00 | 20.28 | O |
| ATOM | 417 | N1 | G | A | 20 | 29.083 | −3.529 | −10.381 | 1.00 | 19.71 | N |

TABLE 1-continued

| | | | | | | | | | | | |
|---|---|---|---|---|---|---|---|---|---|---|---|
| ATOM | 418 | C2 | G | A | 20 | 29.866 | −4.578 | −10.806 | 1.00 | 30.15 | C |
| ATOM | 419 | N2 | G | A | 20 | 30.425 | −5.298 | −9.827 | 1.00 | 16.07 | N |
| ATOM | 420 | N3 | G | A | 20 | 30.087 | −4.899 | −12.076 | 1.00 | 28.31 | N |
| ATOM | 421 | C4 | G | A | 20 | 29.448 | −4.070 | −12.925 | 1.00 | 24.94 | C |
| ATOM | 422 | P | G | A | 21 | 30.059 | −9.091 | −16.845 | 1.00 | 47.68 | P |
| ATOM | 423 | O1P | G | A | 21 | 31.018 | −10.046 | −17.455 | 1.00 | 45.77 | O |
| ATOM | 424 | O2P | G | A | 21 | 28.671 | −8.984 | −17.360 | 1.00 | 42.58 | O |
| ATOM | 425 | O5* | G | A | 21 | 29.931 | −9.438 | −15.286 | 1.00 | 44.78 | O |
| ATOM | 426 | C5* | G | A | 21 | 31.110 | −9.549 | −14.487 | 1.00 | 42.98 | C |
| ATOM | 427 | C4* | G | A | 21 | 30.723 | −9.877 | −13.064 | 1.00 | 46.31 | C |
| ATOM | 428 | O4* | G | A | 21 | 30.215 | −8.681 | −12.421 | 1.00 | 39.27 | O |
| ATOM | 429 | C3* | G | A | 21 | 29.629 | −10.935 | −12.916 | 1.00 | 41.26 | C |
| ATOM | 430 | O3* | G | A | 21 | 29.952 | −11.795 | −11.813 | 1.00 | 46.53 | O |
| ATOM | 431 | C2* | G | A | 21 | 28.386 | −10.117 | −12.594 | 1.00 | 31.18 | C |
| ATOM | 432 | C1* | G | A | 21 | 28.974 | −8.976 | −11.789 | 1.00 | 30.21 | C |
| ATOM | 433 | N9 | G | A | 21 | 28.071 | −7.812 | −11.759 | 1.00 | 34.10 | N |
| ATOM | 434 | C8 | G | A | 21 | 27.497 | −7.101 | −12.773 | 1.00 | 28.90 | C |
| ATOM | 435 | N7 | G | A | 21 | 26.745 | −6.120 | −12.362 | 1.00 | 31.24 | N |
| ATOM | 436 | C5 | G | A | 21 | 26.829 | −6.187 | −10.978 | 1.00 | 26.59 | C |
| ATOM | 437 | C6 | G | A | 21 | 26.233 | −5.387 | −9.978 | 1.00 | 23.05 | C |
| ATOM | 438 | O6 | G | A | 21 | 25.478 | −4.418 | −10.133 | 1.00 | 27.44 | O |
| ATOM | 439 | N1 | G | A | 21 | 26.587 | −5.803 | −8.695 | 1.00 | 24.72 | N |
| ATOM | 440 | C2 | G | A | 21 | 27.410 | −6.856 | −8.404 | 1.00 | 29.87 | C |
| ATOM | 441 | N2 | G | A | 21 | 27.628 | −7.097 | −7.097 | 1.00 | 21.68 | N |
| ATOM | 442 | N3 | G | A | 21 | 27.969 | −7.606 | −9.341 | 1.00 | 28.66 | N |
| ATOM | 443 | C4 | G | A | 21 | 27.643 | −7.224 | −10.587 | 1.00 | 30.31 | C |
| ATOM | 444 | P | G | A | 22 | 29.307 | −13.279 | −11.782 | 1.00 | 54.30 | P |
| ATOM | 445 | O1P | G | A | 22 | 30.405 | −14.278 | −11.674 | 1.00 | 73.64 | O |
| ATOM | 446 | O2P | G | A | 22 | 28.304 | −13.404 | −12.875 | 1.00 | 55.67 | O |
| ATOM | 447 | O5* | G | A | 22 | 28.480 | −13.313 | −10.422 | 1.00 | 59.70 | O |
| ATOM | 448 | C5* | G | A | 22 | 29.149 | −13.358 | −9.160 | 1.00 | 55.20 | C |
| ATOM | 449 | C4* | G | A | 22 | 28.111 | −13.170 | −8.076 | 1.00 | 48.48 | C |
| ATOM | 450 | O4* | G | A | 22 | 27.673 | −11.794 | −8.072 | 1.00 | 44.28 | O |
| ATOM | 451 | C3* | G | A | 22 | 26.855 | −14.024 | −8.236 | 1.00 | 43.52 | C |
| ATOM | 452 | O3* | G | A | 22 | 26.606 | −14.722 | −7.007 | 1.00 | 47.83 | O |
| ATOM | 453 | C2* | G | A | 22 | 25.748 | −13.027 | −8.510 | 1.00 | 41.33 | C |
| ATOM | 454 | C1 | G | A | 22 | 26.261 | −11.747 | −7.871 | 1.00 | 37.12 | C |
| ATOM | 455 | N9 | G | A | 22 | 25.662 | −10.568 | −8.543 | 1.00 | 32.27 | N |
| ATOM | 456 | C8 | G | A | 22 | 25.601 | −10.270 | −9.881 | 1.00 | 25.16 | C |
| ATOM | 457 | N7 | G | A | 22 | 24.993 | −9.137 | −10.109 | 1.00 | 33.62 | N |
| ATOM | 458 | C5 | G | A | 22 | 24.636 | −8.665 | −8.849 | 1.00 | 32.46 | C |
| ATOM | 459 | C6 | G | A | 22 | 23.956 | −7.486 | −8.459 | 1.00 | 29.48 | C |
| ATOM | 460 | O6 | G | A | 22 | 23.508 | −6.574 | −9.172 | 1.00 | 29.24 | O |
| ATOM | 461 | N1 | G | A | 22 | 23.800 | −7.397 | −7.075 | 1.00 | 29.87 | N |
| ATOM | 462 | C2 | G | A | 22 | 24.254 | −8.343 | −6.184 | 1.00 | 33.46 | C |
| ATOM | 463 | N2 | G | A | 22 | 24.026 | −8.112 | −4.884 | 1.00 | 37.57 | N |
| ATOM | 464 | N3 | G | A | 22 | 24.888 | −9.445 | −6.535 | 1.00 | 35.80 | N |
| ATOM | 465 | C4 | G | A | 22 | 25.047 | −9.546 | −7.874 | 1.00 | 35.11 | C |
| TER | 466 | | | A | 22 | | | | | | |
| HETATM | 467 | K | K | | 24 | 22.858 | −4.040 | −8.907 | 1.00 | 28.57 | K |
| HETATM | 468 | K | K | | 25 | 25.685 | −1.967 | −8.823 | 1.00 | 27.19 | K |
| HETATM | 469 | K | K | | 26 | 28.341 | 0.000 | −8.950 | 0.50 | 25.07 | K |
| HETATM | 470 | O | HOH | | 1001 | 24.915 | −6.433 | −21.591 | 1.00 | 57.65 | O |
| HETATM | 471 | O | HOH | | 1002 | 28.988 | −9.721 | −6.086 | 1.00 | 27.28 | O |
| HETATM | 472 | O | HOH | | 1003 | 31.572 | −8.163 | −21.148 | 1.00 | 53.66 | O |
| HETATM | 473 | O | HOH | | 1004 | 17.206 | −1.012 | −2.984 | 1.00 | 34.52 | O |
| HETATM | 474 | O | HOH | | 1005 | 18.640 | −4.918 | −22.492 | 1.00 | 48.37 | O |
| HETATM | 475 | O | HOH | | 1006 | 25.622 | −1.464 | −16.663 | 1.00 | 56.36 | O |
| HETATM | 476 | O | HOH | | 1007 | 32.565 | −8.342 | −18.939 | 1.00 | 65.78 | O |
| HETATM | 477 | O | HOH | | 1008 | 27.285 | 2.995 | −1.516 | 1.00 | 39.76 | O |
| HETATM | 478 | O | HOH | | 1009 | 31.844 | −1.377 | −19.951 | 1.00 | 40.05 | O |
| HETATM | 479 | O | HOH | | 1010 | 18.742 | 0.933 | −14.670 | 1.00 | 52.52 | O |
| HETATM | 480 | O | HOH | | 1011 | 26.578 | −5.577 | −19.493 | 1.00 | 47.02 | O |
| HETATM | 481 | O | HOH | | 1012 | 21.148 | −7.767 | 4.699 | 1.00 | 58.10 | O |
| HETATM | 482 | O | HOH | | 1013 | 20.546 | 6.231 | −11.011 | 1.00 | 38.96 | O |
| HETATM | 483 | O | HOH | | 1014 | 25.196 | 1.171 | −16.783 | 1.00 | 29.16 | O |
| HETATM | 484 | O | HOH | | 1015 | 17.583 | −1.093 | −14.507 | 1.00 | 48.21 | O |
| HETATM | 485 | O | HOH | | 1016 | 28.878 | −1.016 | 8.530 | 1.00 | 53.00 | O |
| HETATM | 486 | O | HOH | | 1017 | 34.853 | −7.292 | 0.121 | 1.00 | 47.46 | O |
| HETATM | 487 | O | HOH | | 1018 | 21.574 | −1.411 | −0.761 | 1.00 | 39.47 | O |
| HETATM | 488 | O | HOH | | 1019 | 22.956 | −8.949 | −1.661 | 1.00 | 50.80 | O |
| HETATM | 489 | O | HOH | | 1020 | 25.127 | −5.723 | −17.038 | 1.00 | 48.32 | O |
| HETATM | 490 | O | HOH | | 1021 | 19.668 | −0.091 | −1.781 | 1.00 | 43.05 | O |
| HETATM | 491 | O | HOH | | 1022 | 38.666 | −13.037 | −3.936 | 0.50 | 38.67 | O |
| HETATM | 492 | O | HOH | | 1023 | 11.101 | 11.924 | −5.526 | 1.00 | 51.89 | O |
| HETATM | 493 | O | HOH | | 1024 | 27.041 | −8.489 | −15.567 | 1.00 | 55.02 | O |
| HETATM | 494 | O | HOH | | 1025 | 21.384 | −2.230 | 3.928 | 0.50 | 41.39 | O |
| HETATM | 495 | O | HOH | | 1026 | 15.427 | 6.579 | −12.379 | 1.00 | 56.24 | O |
| HETATM | 496 | O | HOH | | 1027 | 21.536 | 2.389 | −27.093 | 1.00 | 50.94 | O |

TABLE 1-continued

| | | | | | | | | | | |
|---|---|---|---|---|---|---|---|---|---|---|
| HETATM | 497 | O | HOH | 1028 | 10.380 | 8.874 | −5.616 | 1.00 | 43.77 | O |
| HETATM | 498 | O | HOH | 1029 | 17.633 | −3.522 | −16.926 | 1.00 | 46.34 | O |
| HETATM | 499 | O | HOH | 1030 | 28.054 | −3.282 | 0.911 | 1.00 | 38.52 | O |
| HETATM | 500 | O | HOH | 1031 | 27.188 | −13.223 | −3.709 | 1.00 | 61.04 | O |
| HETATM | 501 | O | HOH | 1032 | 21.553 | 5.704 | −7.953 | 1.00 | 43.79 | O |
| HETATM | 502 | O | HOH | 1033 | 41.764 | −12.459 | −3.333 | 1.00 | 55.79 | O |
| HETATM | 503 | O | HOH | 1034 | 25.501 | −2.192 | −0.734 | 1.00 | 34.74 | O |
| HETATM | 504 | O | HOH | 1035 | 20.186 | 6.480 | −6.275 | 1.00 | 46.16 | O |
| HETATM | 505 | O | HOH | 1036 | 27.719 | −8.096 | 4.186 | 1.00 | 60.80 | O |
| HETATM | 506 | O | HOH | 1037 | 24.342 | −9.372 | 4.923 | 1.00 | 58.79 | O |
| HETATM | 507 | O | HOH | 1038 | 8.243 | 4.570 | −11.416 | 1.00 | 54.58 | O |
| HETATM | 508 | O | HOH | 1039 | 26.722 | −10.987 | −17.991 | 1.00 | 50.74 | O |
| HETATM | 509 | O | HOH | 1040 | 29.196 | −0.768 | −27.178 | 1.00 | 47.26 | O |
| HETATM | 510 | O | HOH | 1041 | 27.585 | 1.116 | 0.551 | 1.00 | 53.73 | O |
| HETATM | 511 | O | HOH | 1042 | 18.996 | 2.637 | −11.515 | 1.00 | 38.86 | O |
| HETATM | 512 | O | HOH | 1043 | 12.694 | 5.446 | −3.572 | 1.00 | 45.19 | O |
| HETATM | 513 | O | HOH | 1044 | 24.942 | −10.539 | −14.731 | 0.50 | 42.17 | O |
| HETATM | 514 | O | HOH | 1045 | 30.673 | −8.664 | −8.765 | 1.00 | 43.52 | O |
| HETATM | 515 | O | HOH | 1046 | 14.775 | −0.423 | −5.652 | 1.00 | 61.39 | O |
| HETATM | 516 | O | HOH | 1047 | 22.268 | −0.333 | 1.577 | 1.00 | 40.11 | O |
| HETATM | 517 | O | HOH | 1048 | 27.429 | −0.696 | −29.888 | 1.00 | 53.72 | O |
| HETATM | 518 | O | HOH | 1049 | 11.531 | 6.707 | −14.980 | 0.50 | 49.83 | O |
| HETATM | 519 | O | HOH | 1050 | 21.804 | 5.092 | −5.399 | 1.00 | 39.64 | O |
| HETATM | 520 | O | HOH | 1051 | 15.506 | −0.875 | −13.547 | 1.00 | 50.32 | O |
| HETATM | 521 | O | HOH | 1052 | 18.852 | 4.834 | −12.176 | 1.00 | 57.34 | O |
| HETATM | 522 | O | HOH | 1053 | 18.514 | 2.397 | −21.099 | 0.50 | 35.84 | O |
| HETATM | 523 | O | HOH | 1054 | 23.736 | 12.928 | −14.636 | 1.00 | 57.62 | O |
| HETATM | 524 | O | HOH | 1055 | 29.594 | −6.796 | −30.656 | 1.00 | 52.39 | O |
| HETATM | 525 | O | HOH | 1056 | 7.477 | 7.447 | −16.600 | 0.50 | 46.83 | O |
| HETATM | 526 | O | HOH | 1057 | 15.084 | 3.510 | −19.361 | 1.00 | 59.75 | O |
| HETATM | 527 | O | HOH | 1058 | 20.839 | 3.806 | 3.688 | 1.00 | 65.25 | O |
| HETATM | 528 | O | HOH | 1059 | 16.443 | 0.483 | −17.727 | 0.50 | 35.41 | O |
| HETATM | 529 | O | HOH | 1060 | 25.167 | −10.436 | −3.711 | 1.00 | 39.92 | O |
| HETATM | 530 | O | HOH | 1061 | 24.567 | 0.251 | 0.184 | 0.50 | 44.72 | O |
| HETATM | 531 | O | HOH | 1062 | 34.315 | −10.251 | −20.936 | 0.50 | 41.72 | O |
| HETATM | 532 | O | HOH | 1063 | 17.140 | −3.021 | −1.375 | 0.50 | 49.40 | O |
| HETATM | 533 | O | HOH | 1064 | 35.360 | −5.681 | 2.448 | 0.50 | 47.27 | O |
| HETATM | 534 | O | HOH | 1065 | 38.634 | −8.642 | 1.739 | 0.50 | 35.84 | O |
| HETATM | 535 | O | HOH | 1066 | 19.429 | −0.607 | −28.344 | 0.50 | 33.82 | O |
| HETATM | 536 | O | HOH | 1067 | 27.219 | 0.387 | −18.364 | 0.50 | 59.35 | O |
| HETATM | 537 | O | HOH | 1068 | 32.331 | −7.041 | −12.055 | 1.00 | 53.26 | O |
| MASTER | 208 | 0 | 3 | 0 | 0 | 0 | 0 | 6 | 536 | 1 | 0 | 2 |
| END | | | | | | | | | | |

TABLE 2

| | | | |
|---|---|---|---|
| HEADER | | DEOXYRIBONUCLEIC ACID | |
| TITLE | | STRUCTURE OF THE HUMAN G-QUADRUPLEX REVEALS A NOVEL TOPOLOGY | |
| COMPND | | MOL_SEQ ID NO: 2 | |
| COMPND | 2 | MOLECULE: 5'-D(*(BRO)UP*AP*GP*GP*GP*(BRO) | |
| COMPND | 3 | UP*TP*AP*GP*GP*GP*T)-3'; | |
| COMPND | 4 | CHAIN | A, B; |
| COMPND | 5 | ENGINEERED | YES |
| SOURCE | | MOL_ID | 1; |
| REMARK | 2 | RESOLUTION. 2.40 ANGSTROMS. | |
| REMARK | 3 | | |
| REMARK | 3 | REFINEMENT. | |
| REMARK | 3 | PROGRAM | SHELXL-97 |
| REMARK | 3 | AUTHORS | G. M. SHELDRICK |
| REMARK | 3 | | |
| REMARK | 3 | DATA USED IN REFINEMENT. | |
| REMARK | 3 | RESOLUTION RANGE HIGH (ANGSTROMS) | 2.40 |
| REMARK | 3 | RESOLUTION RANGE LOW (ANGSTROMS) | 10.00 |
| REMARK | 3 | DATA CUTOFF (SIGMA(F)) | 0.000 |
| REMARK | 3 | COMPLETENESS FOR RANGE (%) | NULL |
| REMARK | 3 | CROSS-VALIDATION METHOD | NULL |
| REMARK | 3 | FREE R VALUE TEST SET SELECTION | RANDOM |
| REMARK | 3 | | |
| REMARK | 3 | FIT TO DATA USED IN REFINEMENT (NO CUTOFF). | |
| REMARK | 3 | R VALUE (WORKING + TEST SET, NO CUTOFF) | 0.197 |
| REMARK | 3 | R VALUE (WORKING SET, NO CUTOFF) | 0.193 |
| REMARK | 3 | FREE R VALUE (NO CUTOFF) | 0.280 |
| REMARK | 3 | FREE R VALUE TEST SET SIZE (%, NO CUTOFF) | NULL |
| REMARK | 3 | FREE R VALUE TEST SET COUNT (NO CUTOFF) | 286 |
| REMARK | 3 | TOTAL NUMBER OF REFLECTIONS (NO CUTOFF) | 3029 |
| REMARK | 3 | | |

TABLE 2-continued

| | | | |
|---|---|---|---|
| REMARK | 3 | FIT/AGREEMENT OF MODEL FOR DATA WITH F > 4SIG(F). | |
| REMARK | 3 | R VALUE (WORKING +TEST SET, F > 4SIG(F)) | NULL |
| REMARK | 3 | R VALUE (WORKING SET, F > 4SIG(F)) | NULL |
| REMARK | 3 | FREE R VALUE (F > 4SIG(F)) | NULL |
| REMARK | 3 | FREE R VALUE TEST SET SIZE (%, F > 4SIG(F)) | NULL |
| REMARK | 3 | FREE R VALUE TEST SET COUNT (F > 4SIG(F)) | NULL |
| REMARK | 3 | TOTAL NUMBER OF REFLECTIONS (F > 4SIG(F)) | NULL |
| REMARK | 3 | | |
| REMARK | 3 | NUMBER OF NON-HYDROGEN ATOMS USED IN REFINEMENT. | |
| REMARK | 3 | PROTEIN ATOMS | 0 |
| REMARK | 3 | NUCLEIC ACID ATOMS | 498 |
| REMARK | 3 | HETEROGEN ATOMS | 7 |
| REMARK | 3 | SOLVENT ATOMS | 50 |
| REMARK | 3 | | |
| REMARK | 3 | MODEL REFINEMENT. | |
| REMARK | 3 | OCCUPANCY SUM OF NON-HYDROGEN ATOMS | NULL |
| REMARK | 3 | OCCUPANCY SUM OF HYDROGEN ATOMS | NULL |
| REMARK | 3 | NUMBER OF DISCRETELY DISORDERED RESIDUES | NULL |
| REMARK | 3 | NUMBER OF LEAST-SQUARES PARAMETERS | NULL |
| REMARK | 3 | NUMBER OF RESTRAINTS | NULL |
| REMARK | 3 | | |
| REMARK | 3 | RMS DEVIATIONS FROM RESTRAINT TARGET VALUES. | |
| REMARK | 3 | BOND LENGTHS (A) | 0.007 |
| REMARK | 3 | ANGLE DISTANCES (A) | 0.016 |
| REMARK | 3 | SIMILAR DISTANCES (NO TARGET VALUES) (A) | NULL |
| REMARK | 3 | DISTANCES FROM RESTRAINT PLANES (A) | 0.012 |
| REMARK | 3 | ZERO CHIRAL VOLUMES (A**3) | NULL |
| REMARK | 3 | NON-ZERO CHIRAL VOLUMES (A**3) | NULL |
| REMARK | 3 | ANTI-BUMPING DISTANCE RESTRAINTS (A) | 0.004 |
| REMARK | 3 | RIGID-BOND ADP COMPONENTS (A**2) | NULL |
| REMARK | 3 | SIMILAR ADP COMPONENTS (A**2) | NULL |
| REMARK | 3 | APPROXIMATELY ISOTROPIC ADPS (A**2) | NULL |
| REMARK | 3 | | |
| REMARK | 3 | BULK SOLVENT MODELING. | |
| REMARK | 3 | METHOD USED | NULL |
| REMARK | 3 | | |
| REMARK | 3 | STEREOCHEMISTRY TARGET VALUES | PARKINSON ET AL. |
| REMARK | 3 | SPECIAL CASE | NULL |
| REMARK | 3 | | |
| REMARK | 3 | OTHER REFINEMENT REMARKS | NULL |
| REMARK | 4 | | |
| REMARK | 4 | COMPLIES WITH FORMAT V. 2.3, 09-JULY-1998 | |
| REMARK | 101 | | |
| REMARK | 101 | RESIDUE +U A 1 HAS BRO BONDED TO C5. | |
| REMARK | 101 | RESIDUE +U A 6 HAS BRO BONDED TO C5. | |
| REMARK | 101 | RESIDUE +U B 13 HAS BRO BONDED TO C5. | |
| REMARK | 101 | RESIDUE +U B 18 HAS BRO BONDED TO C5. | |
| REMARK | 103 | | |
| REMARK | 103 | THERE ARE NON-WATSON-CRICK HYDROGEN BONDS BETWEEN THE | |
| REMARK | 103 | FOLLOWING ATOMS: | |
| REMARK | 103 | N1 G A 3 AND O6 G A 9 | |
| REMARK | 103 | N2 G A 3 AND N7 G A 9 | |
| REMARK | 103 | N7 G A 3 AND N2 G B 21 | |
| REMARK | 103 | O6 G A 3 AND N1 G B 21 | |
| REMARK | 103 | N1 G A 4 AND O6 G A 10 | |
| REMARK | 103 | N2 G A 4 AND N7 G A 10 | |
| REMARK | 103 | N7 G A 4 AND N2 G B 22 | |
| REMARK | 103 | O6 G A 4 AND N1 G B 22 | |
| REMARK | 103 | N1 G A 5 AND O6 G A 11 | |
| REMARK | 103 | N2 G A 5 AND N7 G A 11 | |
| REMARK | 103 | N7 G A 5 AND N2 G B 23 | |
| REMARK | 103 | O6 G A 5 AND N1 G B 23 | |
| REMARK | 103 | N1 G A 9 AND O6 G B 15 | |
| REMARK | 103 | N2 G A 9 AND N7 G B 15 | |
| REMARK | 103 | N1 G A 10 AND O6 G B 16 | |
| REMARK | 103 | N2 G A 10 AND N7 G B 16 | |
| REMARK | 103 | N2 G A 11 AND O4 T A 12 | |
| REMARK | 103 | N1 G A 11 AND O6 G B 17 | |
| REMARK | 103 | N2 G A 11 AND N7 G B 17 | |
| REMARK | 103 | N1 G B 15 AND O6 G B 21 | |
| REMARK | 103 | N2 G B 15 AND N7 G B 21 | |
| REMARK | 103 | N1 G B 16 AND O6 G B 22 | |
| REMARK | 103 | N2 G B 16 AND N7 G B 22 | |
| REMARK | 103 | N1 G B 17 AND O6 G B 23 | |
| REMARK | 103 | N2 G B 17 AND N7 G B 23 | |
| REMARK | 105 | | |
| REMARK | 105 | THE PROTEIN DATA BANK HAS ADOPTED THE SACCHARIDE CHEMISTS | |
| REMARK | 105 | NOMENCLATURE FOR ATOMS OF THE DEOXYRIBOSE/RIBOSE MOIETY | |
| REMARK | 105 | RATHER THAN THAT OF THE NUCLEOSIDE CHEMISTS. THE RING | |

TABLE 2-continued

```
REMARK  105  OXYGEN ATOM IS LABELLED O4* INSTEAD OF O1*.
REMARK  200
REMARK  200  EXPERIMENTAL DETAILS
REMARK  200  EXPERIMENT TYPE                                X-RAY DIFFRACTION
REMARK  200  TEMPERATURE (KELVIN)                           103.0
REMARK  200  PH                                             7.00
REMARK  200  NUMBER OF CRYSTALS USED                        1
REMARK  200
REMARK  200  SYNCHROTRON (Y/N)                              N
REMARK  200  RADIATION SOURCE                               ROTATING ANODE
REMARK  200  BEAMLINE                                       NULL
REMARK  200  X-RAY GENERATOR MODEL                          RIGAKU RU200
REMARK  200  MONOCHROMATIC OR LAUE (M/L)                    M
REMARK  200  WAVELENGTH OR RANGE (A)                        1.5418
REMARK  200  MONOCHROMATOR                                  NULL
REMARK  200  OPTICS                                         OSMIC MIRROR
REMARK  200
REMARK  200  DETECTOR TYPE                                  AREA DETECTOR
REMARK  200  DETECTOR MANUFACTURER                          RIGAKU RAXIS IV
REMARK  200  INTENSITY-INTEGRATION SOFTWARE                 R-AXIS
REMARK  200  DATA SCALING SOFTWARE                          SCALEPACK
REMARK  200
REMARK  200  NUMBER OF UNIQUE REFLECTIONS                   2870
REMARK  200  RESOLUTION RANGE HIGH (A)                      2.400
REMARK  200  RESOLUTION RANGE LOW (A)                       26.000
REMARK  200  REJECTION CRITERIA (SIGMA(I))                  2.000
REMARK  200
REMARK  200  OVERALL.
REMARK  200  COMPLETENESS FOR RANGE (%)                     90.9
REMARK  200  DATA REDUNDANCY                                10.000
REMARK  200  R MERGE (I)                                    0.06800
REMARK  200  R SYM (I)                                      NULL
REMARK  200  <I/SIGMA(I)> FOR THE DATA SET                  15.0000
REMARK  200
REMARK  200  IN THE HIGHEST RESOLUTION SHELL.
REMARK  200  HIGHEST RESOLUTION SHELL, RANGE HIGH (A)       2.40
REMARK  200  HIGHEST RESOLUTION SHELL, RANGE LOW (A)        2.49
REMARK  200  COMPLETENESS FOR SHELL (%)                     99.7
REMARK  200  DATA REDUNDANCY IN SHELL                       10.00
REMARK  200  R MERGE FOR SHELL (I)                          0.28000
REMARK  200  R SYM FOR SHELL (I)                            NULL
REMARK  200  <I/SIGMA(I)> FOR SHELL                         9.600
REMARK  200
REMARK  200  DIFFRACTION PROTOCOL                           SINGLE WAVELENGTH
REMARK  200  METHOD USED TO DETERMINE THE STRUCTURE         MAD
REMARK  200  SOFTWARE USED                                  CNS
REMARK  200  STARTING MODEL                                 NULL
REMARK  200
REMARK  200  REMARK                                         NULL
REMARK  280
REMARK  280  CRYSTAL
REMARK  280  SOLVENT CONTENT, VS (%)                        NULL
REMARK  280  MATTHEWS COEFFICIENT, VM (ANGSTROMS**3/DA)     NULL
REMARK  280
REMARK  280  CRYSTALLIZATION CONDITIONS                     MPD, KCL, LICL, MGCL2
REMARK  290
REMARK  290  CRYSTALLOGRAPHIC SYMMETRY
REMARK  290  SYMMETRY OPERATORS FOR SPACE GROUP             P 31 2 1
REMARK  290
REMARK  290     SYMOP   SYMMETRY
REMARK  290     NNNMMM  OPERATOR
REMARK  290      1555    X, Y, Z
REMARK  290      2555    -Y, X - Y, 1/3+ Z
REMARK  290      3555    -X + Y, -X, 2/3 + Z
REMARK  290      4555    Y, X, -Z
REMARK  290      5555    X - Y, -Y, 2/3 - Z
REMARK  290      6555    -X, -X + Y, 1/3 - Z
REMARK  290
REMARK  290  WHERE NNN->OPERATOR NUMBER
REMARK  290     MMM->TRANSLATION VECTOR
REMARK  290
REMARK  290  CRYSTALLOGRAPHIC SYMMETRY TRANSFORMATIONS
REMARK  290  THE FOLLOWING TRANSFORMATIONS OPERATE ON THE ATOM/HETATM
REMARK  290  RECORDS IN THIS ENTRY TO PRODUCE CRYSTALLOGRAPHICALLY
REMARK  290  RELATED MOLECULES.
REMARK  290  SMTRY1   1   1.000000   0.000000   0.000000   0.00000
REMARK  290  SMTRY2   1   0.000000   1.000000   0.000000   0.00000
REMARK  290  SMTRY3   1   0.000000   0.000000   1.000000   0.00000
REMARK  290  SMTRY1   2  -0.500000  -0.866025   0.000000   0.00000
```

TABLE 2-continued

| REMARK | 290 | SMTRY2 | 2 | 0.866025 | −0.500000 | 0.000000 | 0.00000 | | | |
|---|---|---|---|---|---|---|---|---|---|---|
| REMARK | 290 | SMTRY3 | 2 | 0.000000 | 0.000000 | 1.000000 | 13.51533 | | | |
| REMARK | 290 | SMTRY1 | 3 | −0.500000 | 0.866025 | 0.000000 | 0.00000 | | | |
| REMARK | 290 | SMTRY2 | 3 | −0.866025 | −0.500000 | 0.000000 | 0.00000 | | | |
| REMARK | 290 | SMTRY3 | 3 | 0.000000 | 0.000000 | 1.000000 | 27.03067 | | | |
| REMARK | 290 | SMTRY1 | 4 | −0.500000 | 0.866025 | 0.000000 | 0.00000 | | | |
| REMARK | 290 | SMTRY2 | 4 | 0.866025 | 0.500000 | 0.000000 | 0.00000 | | | |
| REMARK | 290 | SMTRY3 | 4 | 0.000000 | 0.000000 | −1.000000 | 0.00000 | | | |
| REMARK | 290 | SMTRY1 | 5 | 1.000000 | 0.000000 | 0.000000 | 0.00000 | | | |
| REMARK | 290 | SMTRY2 | 5 | 0.000000 | −1.000000 | 0.000000 | 0.00000 | | | |
| REMARK | 290 | SMTRY3 | 5 | 0.000000 | 0.000000 | −1.000000 | 27.03067 | | | |
| REMARK | 290 | SMTRY1 | 6 | −0.500000 | −0.866025 | 0.000000 | 0.00000 | | | |
| REMARK | 290 | SMTRY2 | 6 | −0.866025 | 0.500000 | 0.000000 | 0.00000 | | | |
| REMARK | 290 | SMTRY3 | 6 | 0.000000 | 0.000000 | −1.000000 | 13.51533 | | | |
| REMARK | 290 | | | | | | | | | |
| REMARK | 290 | REMARK | | | | | NULL | | | |
| REMARK | 300 | | | | | | | | | |
| REMARK | 300 | BIOMOLECULE | | | | | 1 | | | |
| REMARK | 300 | THIS ENTRY CONTAINS THE CRYSTALLOGRAPHIC ASYMMETRIC UNIT | | | | | | | | |
| REMARK | 300 | WHICH CONSISTS OF 2 CHAIN(S). SEE REMARK 350 FOR | | | | | | | | |
| REMARK | 300 | INFORMATION ON GENERATING THE BIOLOGICAL MOLECULE(S). | | | | | | | | |
| REMARK | 350 | | | | | | | | | |
| REMARK | 350 | GENERATING THE BIOMOLECULE | | | | | | | | |
| REMARK | 350 | COORDINATES FOR A COMPLETE MULTIMER REPRESENTING THE KNOWN | | | | | | | | |
| REMARK | 350 | BIOLOGICALLY SIGNIFICANT OLIGOMERIZATION STATE OF THE | | | | | | | | |
| REMARK | 350 | MOLECULE CAN BE GENERATED BY APPLYING BIOMT TRANSFORMATIONS | | | | | | | | |
| REMARK | 350 | GIVEN BELOW. BOTH NON-CRYSTALLOGRAPHIC AND | | | | | | | | |
| REMARK | 350 | CRYSTALLOGRAPHIC OPERATIONS ARE GIVEN. | | | | | | | | |
| REMARK | 350 | | | | | | | | | |
| REMARK | 350 | BIOMOLECULE: 1 | | | | | | | | |
| REMARK | 350 | APPLY THE FOLLOWING TO CHAINS: A, B | | | | | | | | |
| REMARK | 350 | BIOMT1 | 1 | 1.000000 | 0.000000 | 0.000000 | 0.00000 | | | |
| REMARK | 350 | BIOMT2 | 1 | 0.000000 | 1.000000 | 0.000000 | 0.00000 | | | |
| REMARK | 350 | BIOMT3 | 1 | 0.000000 | 0.000000 | 1.000000 | 0.00000 | | | |
| SEQRES | 1 | A | 12 | +U A | G G | G +U T | A G | G T | | |
| SEQRES | 1 | B | 12 | +U A | G G | G +U T | A G | G T | | |
| HET | BRO | A | 1 | 1 | | | | | | |
| HET | BRO | A | 6 | 1 | | | | | | |
| HET | BRO | B | 13 | 1 | | | | | | |
| HET | BRO | B | 18 | 1 | | | | | | |
| HET | K | | 25 | 1 | | | | | | |
| HET | K | | 26 | 1 | | | | | | |
| HET | NA | | 27 | 1 | | | | | | |
| HETNAM | | BRO BROMO GROUP | | | | | | | | |
| HETNAM | | K POTASSIUM ION | | | | | | | | |
| HETNAN | | NA SODIUM ION | | | | | | | | |
| FORMUL | 3 | BRO | 4(BR1) | | | | | | | |
| FORMUL | 7 | K | 2(K1 1+) | | | | | | | |
| FORMUL | 9 | NA | NA1 1+ | | | | | | | |
| FORMUL | 10 | HOH | *50(H2 O1) | | | | | | | |
| LINK | C5 | +U A | 1 BR BRO A | | 1 | | | | | |
| LINK | C5 | +U A | 6 BR BRO A | | 6 | | | | | |
| LINK | C5 | +U B | 13 BR BRO B | | 13 | | | | | |
| LINK | C5 | +U B | 18 BR BRO B | | 18 | | | | | |
| CRYST1 | 56.607 56.607 40.546 90.00 90.00 120.00 P 31 2 1 | | | | | 12 | | | | |
| ORIGX1 | 1.000000 | 0.000000 | 0.000000 | 0.00000 | | | | | | |
| ORIGX2 | 0.000000 | 1.000000 | 0.000000 | 0.00000 | | | | | | |
| ORIGX3 | 0.000000 | 0.000000 | 1.000000 | 0.00000 | | | | | | |
| SCALE1 | 0.017666 | 0.010199 | 0.000000 | 0.00000 | | | | | | |
| SCALE2 | 0.000000 | 0.020399 | 0.000000 | 0.00000 | | | | | | |
| SCALE3 | 0.000000 | 0.000000 | 0.024663 | 0.00000 | | | | | | |
| ATOM | 1 | O5* | +U | A | 1 | 6.415 | 10.060 | 42.876 | 1.00 91.93 | O |
| ATOM | 2 | C5* | +U | A | 1 | 4.991 | 10.156 | 42.987 | 1.00 75.23 | C |
| ATOM | 3 | C4* | +U | A | 1 | 4.660 | 11.066 | 44.147 | 1.00 72.07 | C |
| ATOM | 4 | O4* | +U | A | 1 | 5.874 | 11.643 | 44.660 | 1.00 71.68 | O |
| ATOM | 5 | C3* | +U | A | 1 | 3.718 | 12.214 | 43.828 | 1.00 72.68 | C |
| ATOM | 6 | O3* | +U | A | 1 | 2.437 | 12.001 | 44.435 | 1.00 76.46 | O |
| ATOM | 7 | C2* | +U | A | 1 | 4.349 | 13.451 | 44.406 | 1.00 73.19 | C |
| ATOM | 8 | C1* | +U | A | 1 | 5.748 | 13.041 | 44.767 | 1.00 70.99 | C |
| ATOM | 9 | N1 | +U | A | 1 | 6.841 | 13.739 | 44.059 | 1.00 64.25 | N |
| ATOM | 10 | C2 | +U | A | 1 | 7.050 | 15.056 | 44.394 | 1.00 53.85 | C |
| ATOM | 11 | O2 | +U | A | 1 | 6.386 | 15.646 | 45.228 | 1.00 61.93 | O |
| ATOM | 12 | N3 | +U | A | 1 | 8.075 | 15.665 | 43.713 | 1.00 51.30 | N |
| ATOM | 13 | C4 | +U | A | 1 | 8.883 | 15.088 | 42.754 | 1.00 48.32 | C |
| ATOM | 14 | O4 | +U | A | 1 | 9.774 | 15.732 | 42.206 | 1.00 50.51 | O |
| ATOM | 15 | C5 | +U | A | 1 | 8.599 | 13.700 | 42.459 | 1.00 46.13 | C |
| ATOM | 16 | C6 | +U | A | 1 | 7.604 | 13.092 | 43.113 | 1.00 59.37 | C |
| ATOM | 17 | P | A | A | 2 | 1.176 | 12.874 | 43.941 | 1.00 77.36 | P |
| ATOM | 18 | O1P | A | A | 2 | −0.046 | 12.422 | 44.663 | 1.00 90.01 | O |

TABLE 2-continued

| | | | | | | | | | | | |
|---|---|---|---|---|---|---|---|---|---|---|---|
| ATOM | 19 | O2P | A | A | 2 | 1.163 | 12.899 | 42.449 | 1.00 | 74.32 | O |
| ATOM | 20 | O5* | A | A | 2 | 1.513 | 14.350 | 44.444 | 1.00 | 69.57 | O |
| ATOM | 21 | C5* | A | A | 2 | 1.475 | 14.682 | 45.830 | 1.00 | 60.26 | C |
| ATOM | 22 | C4* | A | A | 2 | 1.452 | 16.181 | 46.000 | 1.00 | 61.86 | C |
| ATOM | 23 | O4* | A | A | 2 | 2.735 | 16.739 | 45.650 | 1.00 | 65.11 | O |
| ATOM | 24 | C3* | A | A | 2 | 0.426 | 16.922 | 45.140 | 1.00 | 58.72 | C |
| ATOM | 25 | O3* | A | A | 2 | −0.068 | 18.040 | 45.888 | 1.00 | 58.78 | O |
| ATOM | 26 | C2* | A | A | 2 | 1.242 | 17.377 | 43.946 | 1.00 | 58.54 | C |
| ATOM | 27 | C1* | A | A | 2 | 2.609 | 17.632 | 44.545 | 1.00 | 62.34 | C |
| ATOM | 28 | N9 | A | A | 2 | 3.677 | 17.404 | 43.548 | 1.00 | 60.64 | N |
| ATOM | 29 | C8 | A | A | 2 | 3.876 | 16.348 | 42.699 | 1.00 | 56.66 | C |
| ATOM | 30 | N7 | A | A | 2 | 4.938 | 16.475 | 41.940 | 1.00 | 56.50 | N |
| ATOM | 31 | C5 | A | A | 2 | 5.470 | 17.701 | 42.321 | 1.00 | 55.73 | C |
| ATOM | 32 | C6 | A | A | 2 | 6.607 | 18.401 | 41.878 | 1.00 | 50.84 | C |
| ATOM | 33 | N6 | A | A | 2 | 7.421 | 17.931 | 40.924 | 1.00 | 46.84 | N |
| ATOM | 34 | N1 | A | A | 2 | 6.866 | 19.593 | 42.453 | 1.00 | 45.50 | N |
| ATOM | 35 | C2 | A | A | 2 | 6.035 | 20.033 | 43.400 | 1.00 | 52.99 | C |
| ATOM | 36 | N3 | A | A | 2 | 4.937 | 19.469 | 43.901 | 1.00 | 61.07 | N |
| ATOM | 37 | C4 | A | A | 2 | 4.702 | 18.284 | 43.312 | 1.00 | 58.44 | C |
| ATOM | 38 | P | G | A | 3 | −1.420 | 18.799 | 45.467 | 1.00 | 62.88 | P |
| ATOM | 39 | O1P | G | A | 3 | −2.242 | 19.116 | 46.665 | 1.00 | 60.89 | O |
| ATOM | 40 | O2P | G | A | 3 | −2.044 | 18.102 | 44.304 | 1.00 | 63.90 | O |
| ATOM | 41 | O5* | G | A | 3 | −0.892 | 20.204 | 44.916 | 1.00 | 59.88 | O |
| ATOM | 42 | C5* | G | A | 3 | −0.140 | 21.053 | 45.790 | 1.00 | 54.35 | C |
| ATOM | 43 | C4* | G | A | 3 | 0.509 | 22.133 | 44.954 | 1.00 | 51.81 | C |
| ATOM | 44 | O4* | G | A | 3 | 1.646 | 21.581 | 44.253 | 1.00 | 49.02 | O |
| ATOM | 45 | C3* | G | A | 3 | −0.408 | 22.722 | 43.878 | 1.00 | 52.44 | C |
| ATOM | 46 | O3* | G | A | 3 | −0.605 | 24.100 | 44.197 | 1.00 | 57.65 | O |
| ATOM | 47 | C2* | G | A | 3 | 0.326 | 22.549 | 42.573 | 1.00 | 50.97 | C |
| ATOM | 48 | C1* | G | A | 3 | 1.744 | 22.206 | 42.973 | 1.00 | 52.16 | C |
| ATOM | 49 | N9 | G | A | 3 | 2.376 | 21.304 | 41.986 | 1.00 | 47.12 | N |
| ATOM | 50 | C8 | G | A | 3 | 1.974 | 20.060 | 41.563 | 1.00 | 44.62 | C |
| ATOM | 51 | N7 | G | A | 3 | 2.781 | 19.552 | 40.676 | 1.00 | 46.80 | N |
| ATOM | 52 | C5 | G | A | 3 | 3.768 | 20.510 | 40.504 | 1.00 | 42.66 | C |
| ATOM | 53 | C6 | G | A | 3 | 4.911 | 20.509 | 39.662 | 1.00 | 44.99 | C |
| ATOM | 54 | O6 | G | A | 3 | 5.272 | 19.617 | 38.881 | 1.00 | 49.39 | O |
| ATOM | 55 | N1 | G | A | 3 | 5.654 | 21.680 | 39.792 | 1.00 | 35.38 | N |
| ATOM | 56 | C2 | G | A | 3 | 5.327 | 22.717 | 40.631 | 1.00 | 41.37 | C |
| ATOM | 57 | N2 | G | A | 3 | 6.160 | 23.769 | 40.626 | 1.00 | 41.49 | N |
| ATOM | 58 | N3 | G | A | 3 | 4.264 | 22.726 | 41.419 | 1.00 | 46.18 | N |
| ATOM | 59 | C4 | G | A | 3 | 3.528 | 21.602 | 41.311 | 1.00 | 40.49 | C |
| ATOM | 60 | P | G | A | 4 | −1.270 | 25.169 | 43.217 | 1.00 | 58.80 | P |
| ATOM | 61 | O1P | G | A | 4 | −2.002 | 26.164 | 44.050 | 1.00 | 63.98 | O |
| ATOM | 62 | O2P | G | A | 4 | −1.975 | 24.491 | 42.091 | 1.00 | 61.28 | O |
| ATOM | 63 | O5* | G | A | 4 | −0.013 | 25.910 | 42.574 | 1.00 | 61.24 | O |
| ATOM | 64 | C5* | G | A | 4 | 0.682 | 26.949 | 43.274 | 1.00 | 55.91 | C |
| ATOM | 65 | C4* | G | A | 4 | 1.677 | 27.563 | 42.302 | 1.00 | 53.04 | C |
| ATOM | 66 | O4* | G | A | 4 | 2.540 | 26.491 | 41.840 | 1.00 | 51.36 | O |
| ATOM | 67 | C3* | G | A | 4 | 1.017 | 28.108 | 41.030 | 1.00 | 51.82 | C |
| ATOM | 68 | O3* | G | A | 4 | 0.892 | 29.530 | 41.149 | 1.00 | 50.17 | O |
| ATOM | 69 | C2* | G | A | 4 | 1.968 | 27.748 | 39.916 | 1.00 | 48.91 | C |
| ATOM | 70 | C1* | G | A | 4 | 2.874 | 26.691 | 40.478 | 1.00 | 50.21 | C |
| ATOM | 71 | N9 | G | A | 4 | 2.825 | 25.441 | 39.694 | 1.00 | 48.47 | N |
| ATOM | 72 | C8 | G | A | 4 | 1.982 | 24.362 | 39.817 | 1.00 | 48.31 | C |
| ATOM | 73 | N7 | G | A | 4 | 2.226 | 23.421 | 38.946 | 1.00 | 46.58 | N |
| ATOM | 74 | C5 | G | A | 4 | 3.299 | 23.908 | 38.201 | 1.00 | 47.64 | C |
| ATOM | 75 | C6 | G | A | 4 | 4.009 | 23.337 | 37.111 | 1.00 | 42.93 | C |
| ATOM | 76 | O6 | G | A | 4 | 3.841 | 22.248 | 36.553 | 1.00 | 42.92 | O |
| ATOM | 77 | N1 | G | A | 4 | 5.027 | 24.161 | 36.644 | 1.00 | 43.29 | N |
| ATOM | 78 | C2 | G | A | 4 | 5.322 | 25.397 | 37.173 | 1.00 | 43.23 | C |
| ATOM | 79 | N2 | G | A | 4 | 6.341 | 26.043 | 36.587 | 1.00 | 36.59 | N |
| ATOM | 80 | N3 | G | A | 4 | 4.670 | 25.941 | 38.185 | 1.00 | 37.48 | N |
| ATOM | 81 | C4 | G | A | 4 | 3.676 | 25.158 | 38.655 | 1.00 | 39.12 | C |
| ATOM | 82 | P | G | A | 5 | 0.180 | 30.382 | 39.989 | 1.00 | 55.07 | P |
| ATOM | 83 | O1P | G | A | 5 | −0.012 | 31.776 | 40.485 | 1.00 | 56.59 | O |
| ATOM | 84 | O2P | G | A | 5 | −1.005 | 29.649 | 39.456 | 1.00 | 50.85 | O |
| ATOM | 85 | O5* | G | A | 5 | 1.257 | 30.452 | 38.805 | 1.00 | 50.77 | O |
| ATOM | 86 | C5* | G | A | 5 | 2.305 | 31.419 | 38.870 | 1.00 | 48.88 | C |
| ATOM | 87 | C4* | G | A | 5 | 3.050 | 31.483 | 37.566 | 1.00 | 47.92 | C |
| ATOM | 88 | O4* | G | A | 5 | 3.557 | 30.176 | 37.218 | 1.00 | 47.71 | O |
| ATOM | 89 | C3* | G | A | 5 | 2.246 | 31.963 | 36.358 | 1.00 | 47.30 | C |
| ATOM | 90 | O3* | G | A | 5 | 3.097 | 32.806 | 35.564 | 1.00 | 46.12 | O |
| ATOM | 91 | C2* | G | A | 5 | 1.948 | 30.682 | 35.599 | 1.00 | 47.96 | C |
| ATOM | 92 | C1* | G | A | 5 | 3.179 | 29.837 | 35.883 | 1.00 | 45.01 | C |
| ATOM | 93 | N9 | G | A | 5 | 2.848 | 28.398 | 35.778 | 1.00 | 42.20 | N |
| ATOM | 94 | C8 | G | A | 5 | 1.904 | 27.679 | 36.472 | 1.00 | 38.19 | C |
| ATOM | 95 | N7 | G | A | 5 | 1.886 | 26.426 | 36.123 | 1.00 | 45.15 | N |
| ATOM | 96 | C5 | G | A | 5 | 2.864 | 26.301 | 35.148 | 1.00 | 38.50 | C |
| ATOM | 97 | C6 | G | A | 5 | 3.279 | 25.156 | 34.416 | 1.00 | 43.96 | C |

TABLE 2-continued

| | | | | | | | | | | | |
|---|---|---|---|---|---|---|---|---|---|---|---|
| ATOM | 98  | O6   | G  | A | 5 | 2.848  | 23.991 | 34.487 | 1.00 | 30.44 | O |
| ATOM | 99  | N1   | G  | A | 5 | 4.305  | 25.475 | 33.525 | 1.00 | 40.81 | N |
| ATOM | 100 | C2   | G  | A | 5 | 4.844  | 26.732 | 33.377 | 1.00 | 35.86 | C |
| ATOM | 101 | N2   | G  | A | 5 | 5.827  | 26.854 | 32.471 | 1.00 | 27.58 | N |
| ATOM | 102 | N3   | G  | A | 5 | 4.460  | 27.802 | 34.058 | 1.00 | 34.14 | N |
| ATOM | 103 | C4   | G  | A | 5 | 3.468  | 27.524 | 34.928 | 1.00 | 37.82 | C |
| ATOM | 104 | P    | +U | A | 6 | 2.610  | 34.326 | 35.309 | 1.00 | 50.87 | P |
| ATOM | 105 | O1P  | +U | A | 6 | 3.651  | 35.112 | 34.603 | 1.00 | 44.39 | O |
| ATOM | 106 | O2P  | +U | A | 6 | 1.232  | 34.262 | 34.741 | 1.00 | 61.43 | O |
| ATOM | 107 | O5*  | +U | A | 6 | 2.479  | 34.890 | 36.795 | 1.00 | 51.94 | O |
| ATOM | 108 | C5*  | +U | A | 6 | 3.573  | 35.515 | 37.472 | 1.00 | 41.00 | C |
| ATOM | 109 | C4*  | +U | A | 6 | 3.104  | 35.880 | 38.852 | 1.00 | 37.66 | C |
| ATOM | 110 | O4*  | +U | A | 6 | 2.711  | 34.692 | 39.570 | 1.00 | 44.90 | O |
| ATOM | 111 | C3*  | +U | A | 6 | 4.080  | 36.621 | 39.752 | 1.00 | 41.57 | C |
| ATOM | 112 | O3*  | +U | A | 6 | 3.482  | 37.868 | 40.151 | 1.00 | 47.62 | O |
| ATOM | 113 | C2*  | +U | A | 6 | 4.221  | 35.756 | 40.989. | 1.00 | 40.35 | C |
| ATOM | 114 | C1*  | +U | A | 6 | 2.931  | 34.958 | 40.960 | 1.00 | 47.46 | C |
| ATOM | 115 | N1   | +U | A | 6 | 2.959  | 33.677 | 41.704 | 1.00 | 53.94 | N |
| ATOM | 116 | C2   | +U | A | 6 | 1.959  | 33.453 | 42.612 | 1.00 | 56.99 | C |
| ATOM | 117 | O2   | +U | A | 6 | 1.052  | 34.232 | 42.852 | 1.00 | 58.16 | O |
| ATOM | 118 | N3   | +U | A | 6 | 2.031  | 32.247 | 43.275 | 1.00 | 54.96 | N |
| ATOM | 119 | C4   | +U | A | 6 | 3.001  | 31.282 | 43.097 | 1.00 | 52.31 | C |
| ATOM | 120 | O4   | +U | A | 6 | 2.993  | 30.233 | 43.731 | 1.00 | 55.87 | O |
| ATOM | 121 | C5   | +U | A | 6 | 4.012  | 31.603 | 42.122 | 1.00 | 46.55 | C |
| ATOM | 122 | C6   | +U | A | 6 | 3.962  | 32.764 | 41.470 | 1.00 | 47.43 | C |
| ATOM | 123 | P    | T  | A | 7 | 4.286  | 39.209 | 39.759 | 1.00 | 50.52 | P |
| ATOM | 124 | O1P  | T  | A | 7 | 3.393  | 40.383 | 39.971 | 1.00 | 54.30 | O |
| ATOM | 125 | O2P  | T  | A | 7 | 4.947  | 39.007 | 38.443 | 1.00 | 55.58 | O |
| ATOM | 126 | O5*  | T  | A | 7 | 5.442  | 39.249 | 40.854 | 1.00 | 38.59 | O |
| ATOM | 127 | C5*  | T  | A | 7 | 6.710  | 39.816 | 40.521 | 1.00 | 36.58 | C |
| ATOM | 128 | C4*  | T  | A | 7 | 7.643  | 39.596 | 41.691 | 1.00 | 43.06 | C |
| ATOM | 129 | O4*  | T  | A | 7 | 6.949  | 39.960 | 42.921 | 1.00 | 46.29 | O |
| ATOM | 130 | C3*  | T  | A | 7 | 7.978  | 38.109 | 41.924 | 1.00 | 47.67 | C |
| ATOM | 131 | O3*  | T  | A | 7 | 8.997  | 37.673 | 41.033 | 1.00 | 56.92 | O |
| ATOM | 132 | C2*  | T  | A | 7 | 8.452  | 38.198 | 43.368 | 1.00 | 49.69 | C |
| ATOM | 133 | C1*  | T  | A | 7 | 7.333  | 39.067 | 43.961 | 1.00 | 49.03 | C |
| ATOM | 134 | N1   | T  | A | 7 | 6.171  | 38.275 | 44.430 | 1.00 | 36.46 | N |
| ATOM | 135 | C2   | T  | A | 7 | 6.405  | 37.411 | 45.472 | 1.00 | 38.26 | C |
| ATOM | 136 | O2   | T  | A | 7 | 7.496  | 37.283 | 46.004 | 1.00 | 59.10 | O |
| ATOM | 137 | N3   | T  | A | 7 | 5.307  | 36.694 | 45.878 | 1.00 | 42.39 | N |
| ATOM | 138 | C4   | T  | A | 7 | 4.031  | 36.755 | 45.352 | 1.00 | 40.21 | C |
| ATOM | 139 | O4   | T  | A | 7 | 3.143  | 36.049 | 45.820 | 1.00 | 40.83 | O |
| ATOM | 140 | C5   | T  | A | 7 | 3.865  | 37.683 | 44.261 | 1.00 | 35.94 | C |
| ATOM | 141 | C5M  | T  | A | 7 | 2.511  | 37.816 | 43.631 | 1.00 | 44.83 | C |
| ATOM | 142 | C6   | T  | A | 7 | 4.934  | 38.389 | 43.858 | 1.00 | 35.82 | C |
| ATOM | 143 | P    | A  | A | 8 | 8.873  | 36.264 | 40.255 | 1.00 | 48.30 | P |
| ATOM | 144 | O1P  | A  | A | 8 | 10.016 | 36.130 | 39.312 | 1.00 | 71.33 | O |
| ATOM | 145 | O2P  | A  | A | 8 | 7.504  | 36.059 | 39.719 | 1.00 | 51.04 | O |
| ATOM | 146 | O5*  | A  | A | 8 | 9.058  | 35.192 | 41.427 | 1.00 | 50.73 | O |
| ATOM | 147 | C5*  | A  | A | 8 | 10.296 | 35.107 | 42.134 | 1.00 | 41.91 | C |
| ATOM | 148 | C4*  | A  | A | 8 | 10.422 | 33.742 | 42.767 | 1.00 | 40.92 | C |
| ATOM | 149 | O4*  | A  | A | 8 | 9.505  | 33.629 | 43.876 | 1.00 | 37.75 | O |
| ATOM | 150 | C3*  | A  | A | 8 | 10.067 | 32.580 | 41.828 | 1.00 | 45.32 | C |
| ATOM | 151 | O3*  | A  | A | 8 | 10.831 | 31.439 | 42.243 | 1.00 | 54.90 | O |
| ATOM | 152 | C2*  | A  | A | 8 | 8.598  | 32.342 | 42.121 | 1.00 | 37.44 | C |
| ATOM | 153 | C1*  | A  | A | 8 | 8.519  | 32.633 | 43.607 | 1.00 | 43.21 | C |
| ATOM | 154 | N9   | A  | A | 8 | 7.166  | 33.116 | 43.965 | 1.00 | 54.65 | N |
| ATOM | 155 | C8   | A  | A | 8 | 6.437  | 34.155 | 43.456 | 1.00 | 54.04 | C |
| ATOM | 156 | N7   | A  | A | 8 | 5.260  | 34.291 | 44.025 | 1.00 | 54.07 | N |
| ATOM | 157 | C5   | A  | A | 8 | 5.223  | 33.273 | 44.967 | 1.00 | 47.83 | C |
| ATOM | 158 | C6   | A  | A | 8 | 4.247  | 32.880 | 45.896 | 1.00 | 51.00 | C |
| ATOM | 159 | N6   | A  | A | 8 | 3.063  | 33.476 | 46.053 | 1.00 | 53.52 | N |
| ATOM | 160 | N1   | A  | A | 8 | 4.541  | 31.822 | 46.679 | 1.00 | 60.22 | N |
| ATOM | 161 | C2   | A  | A | 8 | 5.723  | 31.211 | 46.536 | 1.00 | 59.21 | C |
| ATOM | 162 | N3   | A  | A | 8 | 6.723  | 31.484 | 45.701 | 1.00 | 51.86 | N |
| ATOM | 163 | C4   | A  | A | 8 | 6.393  | 32.541 | 44.940 | 1.00 | 49.68 | C |
| ATOM | 164 | P    | G  | A | 9 | 12.260 | 31.151 | 41.543 | 1.00 | 48.96 | P |
| ATOM | 165 | O1P  | G  | A | 9 | 12.965 | 30.167 | 42.406 | 1.00 | 36.62 | O |
| ATOM | 166 | O2P  | G  | A | 9 | 12.936 | 32.444 | 41.214 | 1.00 | 49.58 | O |
| ATOM | 167 | O5*  | G  | A | 9 | 11.848 | 30.522 | 40.151 | 1.00 | 39.56 | O |
| ATOM | 168 | C5*  | G  | A | 9 | 11.303 | 29.220 | 39.947 | 1.00 | 43.67 | C |
| ATOM | 169 | C4*  | G  | A | 9 | 11.749 | 28.708 | 38.601 | 1.00 | 48.52 | C |
| ATOM | 170 | O4*  | G  | A | 9 | 11.593 | 27.277 | 38.507 | 1.00 | 49.60 | O |
| ATOM | 171 | C3*  | G  | A | 9 | 11.020 | 29.295 | 37.390 | 1.00 | 46.69 | C |
| ATOM | 172 | O3*  | G  | A | 9 | 11.967 | 29.386 | 36.312 | 1.00 | 40.33 | O |
| ATOM | 173 | C2*  | G  | A | 9 | 9.989  | 28.224 | 37.069 | 1.00 | 46.74 | C |
| ATOM | 174 | C1*  | G  | A | 9 | 10.726 | 26.945 | 37.425 | 1.00 | 45.38 | C |
| ATOM | 175 | N9   | G  | A | 9 | 9.770  | 25.882 | 37.801 | 1.00 | 41.51 | N |
| ATOM | 176 | C8   | G  | A | 9 | 8.793  | 25.871 | 38.764 | 1.00 | 38.04 | C |

TABLE 2-continued

| | | | | | | | | | | | |
|---|---|---|---|---|---|---|---|---|---|---|---|
| ATOM | 177 | N7 | G | A | 9 | 8.130 | 24.739 | 38.812 | 1.00 | 32.52 | N |
| ATOM | 178 | C5 | G | A | 9 | 8.714 | 23.971 | 37.821 | 1.00 | 32.46 | C |
| ATOM | 179 | C6 | G | A | 9 | 8.433 | 22.652 | 37.391 | 1.00 | 35.71 | C |
| ATOM | 180 | 06 | G | A | 9 | 7.570 | 21.898 | 37.841 | 1.00 | 34.32 | O |
| ATOM | 181 | N1 | G | A | 9 | 9.267 | 22.256 | 36.351 | 1.00 | 42.53 | N |
| ATOM | 182 | C2 | G | A | 9 | 10.254 | 23.025 | 35.786 | 1.00 | 45.60 | C |
| ATOM | 183 | N2 | G | A | 9 | 10.961 | 22.475 | 34.789 | 1.00 | 44.53 | N |
| ATOM | 184 | N3 | G | A | 9 | 10.530 | 24.259 | 36.175 | 1.00 | 49.91 | N |
| ATOM | 185 | C4 | G | A | 9 | 9.727 | 24.657 | 37.185 | 1.00 | 42.90 | C |
| ATOM | 186 | P | G | A | 10 | 11.500 | 30.127 | 34.954 | 1.00 | 48.05 | P |
| ATOM | 187 | O1P | G | A | 10 | 12.621 | 31.013 | 34.524 | 1.00 | 59.15 | O |
| ATOM | 188 | O2P | G | A | 10 | 10.132 | 30.674 | 35.139 | 1.00 | 48.00 | O |
| ATOM | 189 | O5* | G | A | 10 | 11.367 | 28.944 | 33.892 | 1.00 | 51.86 | O |
| ATOM | 190 | C5* | G | A | 10 | 12.500 | 28.125 | 33.610 | 1.00 | 52.62 | C |
| ATOM | 191 | C4* | G | A | 10 | 12.294 | 27.315 | 32.368 | 1.00 | 48.16 | C |
| ATOM | 192 | O4* | G | A | 10 | 11.666 | 26.056 | 32.673 | 1.00 | 45.31 | O |
| ATOM | 193 | C3* | G | A | 10 | 11.489 | 27.926 | 31.225 | 1.00 | 42.81 | C |
| ATOM | 194 | O3* | G | A | 10 | 12.100 | 27.502 | 29.997 | 1.00 | 48.62 | O |
| ATOM | 195 | C2* | G | A | 10 | 10.126 | 27.267 | 31.354 | 1.00 | 37.72 | C |
| ATOM | 196 | C1* | G | A | 10 | 10.460 | 25.904 | 31.913 | 1.00 | 44.04 | C |
| ATOM | 197 | N9 | G | A | 10 | 9.380 | 25.411 | 32.804 | 1.00 | 45.21 | N |
| ATOM | 198 | C8 | G | A | 10 | 8.767 | 26.066 | 33.849 | 1.00 | 38.07 | C |
| ATOM | 199 | N7 | G | A | 10 | 7.856 | 25.330 | 34.418 | 1.00 | 32.04 | N |
| ATOM | 200 | C5 | G | A | 10 | 7.886 | 24.136 | 33.703 | 1.00 | 30.37 | C |
| ATOM | 201 | C6 | G | A | 10 | 7.111 | 22.961 | 33.874 | 1.00 | 35.33 | C |
| ATOM | 202 | O6 | G | A | 10 | 6.227 | 22.759 | 34.720 | 1.00 | 39.49 | O |
| ATOM | 203 | N1 | G | A | 10 | 7.458 | 21.994 | 32.941 | 1.00 | 35.01 | N |
| ATOM | 204 | C2 | G | A | 10 | 8.418 | 22.118 | 31.967 | 1.00 | 35.34 | C |
| ATOM | 205 | N2 | G | A | 10 | 8.572 | 21.044 | 31.183 | 1.00 | 32.09 | N |
| ATOM | 206 | N3 | G | A | 10 | 9.149 | 23.209 | 31.796 | 1.00 | 38.06 | N |
| ATOM | 207 | C4 | G | A | 10 | 8.825 | 24.167 | 32.697 | 1.00 | 36.02 | C |
| ATOM | 208 | P | G | A | 11 | 11.530 | 28.040 | 28.592 | 1.00 | 53.82 | P |
| ATOM | 209 | O1P | G | A | 11 | 12.681 | 28.209 | 27.658 | 1.00 | 74.61 | O |
| ATOM | 210 | O2P | G | A | 11 | 10.577 | 29.152 | 28.799 | 1.00 | 45.32 | O |
| ATOM | 211 | O5* | G | A | 11 | 10.692 | 26.781 | 28.060 | 1.00 | 59.78 | O |
| ATOM | 212 | C5* | G | A | 11 | 11.391 | 25.576 | 27.728 | 1.00 | 47.81 | C |
| ATOM | 213 | C4* | G | A | 11 | 10.520 | 24.715 | 26.848 | 1.00 | 54.22 | C |
| ATOM | 214 | O4* | G | A | 11 | 9.626 | 23.932 | 27.676 | 1.00 | 55.95 | O |
| ATOM | 215 | C3* | G | A | 11 | 9.597 | 25.483 | 25.888 | 1.00 | 53.53 | C |
| ATOM | 216 | O3* | G | A | 11 | 9.290 | 24.609 | 24.793 | 1.00 | 60.94 | O |
| ATOM | 217 | C2* | G | A | 11 | 8.344 | 25.654 | 26.743 | 1.00 | 47.29 | C |
| ATOM | 218 | C1* | G | A | 11 | 8.273 | 24.299 | 27.426 | 1.00 | 47.17 | C |
| ATOM | 219 | N9 | G | A | 11 | 7.483 | 24.376 | 28.671 | 1.00 | 42.72 | N |
| ATOM | 220 | C8 | G | A | 11 | 7.367 | 25.401 | 29.573 | 1.00 | 40.62 | C |
| ATOM | 221 | N7 | G | A | 11 | 6.572 | 25.105 | 30.562 | 1.00 | 43.41 | N |
| ATOM | 222 | C5 | G | A | 11 | 6.133 | 23.812 | 30.307 | 1.00 | 41.67 | C |
| ATOM | 223 | C6 | G | A | 11 | 5.256 | 22.974 | 31.039 | 1.00 | 40.53 | C |
| ATOM | 224 | O6 | G | A | 11 | 4.640 | 23.164 | 32.101 | 1.00 | 47.61 | O |
| ATOM | 225 | N1 | G | A | 11 | 5.086 | 21.742 | 30.422 | 1.00 | 42.14 | N |
| ATOM | 226 | C2 | G | A | 11 | 5.688 | 21.365 | 29.248 | 1.00 | 46.94 | C |
| ATOM | 227 | N2 | G | A | 11 | 5.367 | 20.121 | 28.853 | 1.00 | 34.29 | N |
| ATOM | 228 | N3 | G | A | 11 | 6.510 | 22.137 | 28.556 | 1.00 | 47.55 | N |
| ATOM | 229 | C4 | G | A | 11 | 6.694 | 23.348 | 29.133 | 1.00 | 45.88 | C |
| ATOM | 230 | P | T | A | 12 | 10.157 | 24.600 | 23.439 | 1.00 | 67.04 | P |
| ATOM | 231 | O1P | T | A | 12 | 11.611 | 24.606 | 23.765 | 1.00 | 79.58 | O |
| ATOM | 232 | O2P | T | A | 12 | 9.645 | 25.651 | 22.520 | 1.00 | 72.18 | O |
| ATOM | 233 | O5* | T | A | 12 | 9.815 | 23.170 | 22.824 | 1.00 | 63.97 | O |
| ATOM | 234 | C5* | T | A | 12 | 8.917 | 22.999 | 21.725 | 0.50 | 66.01 | C |
| ATOM | 235 | C4* | T | A | 12 | 9.200 | 21.661 | 21.078 | 0.50 | 67.50 | C |
| ATOM | 236 | O4* | T | A | 12 | 9.803 | 20.786 | 22.067 | 0.50 | 70.71 | O |
| ATOM | 237 | C3* | T | A | 12 | 7.960 | 20.911 | 20.585 | 0.50 | 69.61 | C |
| ATOM | 238 | O3* | T | A | 12 | 7.725 | 21.218 | 19.202 | 0.50 | 84.76 | O |
| ATOM | 239 | C2* | T | A | 12 | 8.397 | 19.461 | 20.710 | 0.50 | 65.86 | C |
| ATOM | 240 | C1* | T | A | 12 | 9.235 | 19.489 | 21.979 | 0.50 | 60.85 | C |
| ATOM | 241 | N1 | T | A | 12 | 8.497 | 19.157 | 23.218 | 0.10 | 39.48 | N |
| ATOM | 242 | C2 | T | A | 12 | 8.641 | 17.877 | 23.695 | 0.10 | 39.48 | C |
| ATOM | 243 | O2 | T | A | 12 | 9.331 | 17.028 | 23.155 | 0.10 | 39.48 | O |
| ATOM | 244 | N3 | T | A | 12 | 7.934 | 17.624 | 24.847 | 0.10 | 39.48 | N |
| ATOM | 245 | C4 | T | A | 12 | 7.127 | 18.508 | 25.536 | 0.10 | 39.48 | C |
| ATOM | 246 | O4 | T | A | 12 | 6.557 | 18.133 | 26.557 | 0.10 | 39.48 | O |
| ATOM | 247 | C5 | T | A | 12 | 7.026 | 19.834 | 24.972 | 0.10 | 39.48 | C |
| ATOM | 248 | C5M | T | A | 12 | 6.174 | 20.859 | 25.651 | 0.10 | 39.48 | C |
| ATOM | 249 | C6 | T | A | 12 | 7.711 | 20.092 | 23.848 | 0.10 | 39.48 | C |
| TER | 250 | | T | A | 12 | | | | | | |
| HETATM | 251 | BR | BRO | A | 1 | 9.686 | 12.900 | 41.159 | 1.00 | 31.45 | BR |
| HETATM | 252 | BR | BRO | A | 6 | 5.356 | 30.330 | 41.838 | 1.00 | 36.46 | BR |
| ATOM | 253 | O5* | +U | B | 13 | 14.738 | 23.901 | 39.484 | 1.00 | 41.38 | O |
| ATOM | 254 | C5* | +U | B | 13 | 16.046 | 24.462 | 39.338 | 1.00 | 51.00 | C |
| ATOM | 255 | C4* | +U | B | 13 | 16.947 | 23.481 | 38.619 | 1.00 | 43.74 | C |

TABLE 2-continued

| ATOM | 256 | O4* | +U | B | 13 | 17.133 | 22.322 | 39.455 | 1.00 | 48.55 | O |
|---|---|---|---|---|---|---|---|---|---|---|---|
| ATOM | 257 | C3* | +U | B | 13 | 16.425 | 22.972 | 37.286 | 1.00 | 37.37 | C |
| ATOM | 258 | O3* | +U | B | 13 | 17.106 | 23.593 | 36.195 | 1.00 | 42.96 | O |
| ATOM | 259 | C2* | +U | B | 13 | 16.686 | 21.487 | 37.286 | 1.00 | 40.66 | C |
| ATOM | 260 | C1* | +U | B | 13 | 16.822 | 21.145 | 38.742 | 1.00 | 46.10 | C |
| ATOM | 261 | N1 | +U | B | 13 | 15.689 | 20.432 | 39.370 | 1.00 | 41.30 | N |
| ATOM | 262 | C2 | +U | B | 13 | 15.349 | 19.213 | 38.837 | 1.00 | 42.85 | C |
| ATOM | 263 | O2 | +U | B | 13 | 15.920 | 18.696 | 37.888 | 1.00 | 37.85 | O |
| ATOM | 264 | N3 | +U | B | 13 | 14.286 | 18.583 | 39.453 | 1.00 | 39.45 | N |
| ATOM | 265 | C4 | +U | B | 13 | 13.577 | 19.082 | 40.528 | 1.00 | 42.32 | C |
| ATOM | 266 | O4 | +U | B | 13 | 12.644 | 18.455 | 41.017 | 1.00 | 43.14 | O |
| ATOM | 267 | C5 | +U | B | 13 | 13.996 | 20.375 | 41.038 | 1.00 | 39.55 | C |
| ATOM | 268 | C6 | +U | B | 13 | 15.022 | 20.990 | 40.445 | 1.00 | 36.79 | C |
| ATOM | 269 | P | A | B | 14 | 16.398 | 23.721 | 34.755 | 1.00 | 44.99 | P |
| ATOM | 270 | O1P | A | B | 14 | 17.198 | 24.625 | 33.887 | 1.00 | 57.21 | O |
| ATOM | 271 | O2P | A | B | 14 | 14.948 | 24.024 | 34.952 | 1.00 | 51.93 | O |
| ATOM | 272 | O5* | A | B | 14 | 16.474 | 22.261 | 34.131 | 1.00 | 42.72 | O |
| ATOM | 273 | C5* | A | B | 14 | 17.649 | 21.459 | 34.134 | 1.00 | 37.36 | C |
| ATOM | 274 | C4* | A | B | 14 | 17.411 | 20.198 | 33.337 | 1.00 | 41.16 | C |
| ATOM | 275 | O4* | A | B | 14 | 16.649 | 19.258 | 34.127 | 1.00 | 39.81 | O |
| ATOM | 276 | C3* | A | B | 14 | 16.575 | 20.391 | 32.063 | 1.00 | 43.21 | C |
| ATOM | 277 | O3* | A | B | 14 | 16.833 | 19.266 | 31.207 | 1.00 | 45.11 | O |
| ATOM | 278 | C2* | A | B | 14 | 15.155 | 20.278 | 32.613 | 1.00 | 44.14 | C |
| ATOM | 279 | C1* | A | B | 14 | 15.316 | 19.154 | 33.618 | 1.00 | 44.60 | C |
| ATOM | 280 | N9 | A | B | 14 | 14.319 | 19.276 | 34.701 | 1.00 | 48.92 | N |
| ATOM | 281 | C8 | A | B | 14 | 14.030 | 20.347 | 35.513 | 1.00 | 48.42 | C |
| ATOM | 282 | N7 | A | B | 14 | 13.076 | 20.098 | 36.377 | 1.00 | 47.66 | N |
| ATOM | 283 | C5 | A | B | 14 | 12.718 | 18.779 | 36.115 | 1.00 | 43.26 | C |
| ATOM | 284 | C6 | A | B | 14 | 11.765 | 17.920 | 36.686 | 1.00 | 44.15 | C |
| ATOM | 285 | N6 | A | B | 14 | 10.951 | 18.267 | 37.690 | 1.00 | 37.45 | N |
| ATOM | 286 | N1 | A | B | 14 | 11.677 | 16.670 | 36.179 | 1.00 | 49.73 | N |
| ATOM | 287 | C2 | A | B | 14 | 12.482 | 16.299 | 35.173 | 1.00 | 39.57 | C |
| ATOM | 288 | N3 | A | B | 14 | 13.416 | 17.026 | 34.558 | 1.00 | 39.04 | N |
| ATOM | 289 | C4 | A | B | 14 | 13.481 | 18.260 | 35.081 | 1.00 | 42.44 | C |
| ATOM | 290 | P | G | B | 15 | 16.479 | 19.427 | 29.640 | 1.00 | 54.79 | P |
| ATOM | 291 | O1P | G | B | 15 | 17.492 | 18.662 | 28.862 | 1.00 | 89.72 | O |
| ATOM | 292 | O2P | G | B | 15 | 16.229 | 20.857 | 29.333 | 1.00 | 54.18 | O |
| ATOM | 293 | O5* | G | B | 15 | 15.085 | 18.666 | 29.478 | 1.00 | 48.93 | O |
| ATOM | 294 | C5* | G | B | 15 | 15.042 | 17.274 | 29.784 | 1.00 | 47.43 | C |
| ATOM | 295 | C4* | G | B | 15 | 13.624 | 16.794 | 29.840 | 1.00 | 47.26 | C |
| ATOM | 296 | O4* | G | B | 15 | 13.032 | 17.107 | 31.125 | 1.00 | 41.98 | O |
| ATOM | 297 | C3* | G | B | 15 | 12.665 | 17.345 | 28.779 | 1.00 | 51.65 | C |
| ATOM | 298 | O3* | G | B | 15 | 11.916 | 16.222 | 28.280 | 1.00 | 60.02 | O |
| ATOM | 299 | C2* | G | B | 15 | 11.717 | 18.229 | 29.591 | 1.00 | 43.80 | C |
| ATOM | 300 | C1* | G | B | 15 | 11.659 | 17.443 | 30.890 | 1.00 | 39.34 | C |
| ATOM | 301 | N9 | G | B | 15 | 11.094 | 18.244 | 31.986 | 1.00 | 39.02 | N |
| ATOM | 302 | C8 | G | B | 15 | 11.324 | 19.551 | 32.339 | 1.00 | 36.09 | C |
| ATOM | 303 | N7 | G | B | 15 | 10.631 | 19.913 | 33.381 | 1.00 | 42.10 | N |
| ATOM | 304 | C5 | G | B | 15 | 9.899 | 18.788 | 33.740 | 1.00 | 46.08 | C |
| ATOM | 305 | C6 | G | B | 15 | 8.970 | 18.572 | 34.792 | 1.00 | 45.19 | C |
| ATOM | 306 | O6 | G | B | 15 | 8.582 | 19.360 | 35.660 | 1.00 | 35.52 | O |
| ATOM | 307 | N1 | G | B | 15 | 8.460 | 17.279 | 34.793 | 1.00 | 41.08 | N |
| ATOM | 308 | C2 | G | B | 15 | 8.810 | 16.312 | 33.882 | 1.00 | 44.54 | C |
| ATOM | 309 | N2 | G | B | 15 | 8.208 | 15.125 | 34.052 | 1.00 | 58.92 | N |
| ATOM | 310 | N3 | G | B | 15 | 9.673 | 16.494 | 32.898 | 1.00 | 43.64 | N |
| ATOM | 311 | C4 | G | B | 15 | 10.176 | 17.745 | 32.884 | 1.00 | 41.82 | C |
| ATOM | 312 | P | G | B | 16 | 11.403 | 16.178 | 26.756 | 1.00 | 62.96 | P |
| ATOM | 313 | O1P | G | B | 16 | 12.335 | 15.323 | 25.972 | 1.00 | 80.31 | O |
| ATOM | 314 | O2P | G | B | 16 | 11.123 | 17.559 | 26.289 | 1.00 | 62.58 | O |
| ATOM | 315 | O5* | G | B | 16 | 10.001 | 15.407 | 26.899 | 1.00 | 60.22 | O |
| ATOM | 316 | C5* | G | B | 16 | 9.763 | 14.667 | 28.095 | 1.00 | 61.54 | C |
| ATOM | 317 | C4* | G | B | 16 | 8.323 | 14.306 | 28.295 | 1.00 | 67.57 | C |
| ATOM | 318 | O4* | G | B | 16 | 7.900 | 14.623 | 29.638 | 1.00 | 66.85 | O |
| ATOM | 319 | C3* | G | B | 16 | 7.287 | 14.883 | 27.351 | 1.00 | 68.25 | C |
| ATOM | 320 | O3* | G | B | 16 | 6.519 | 13.823 | 26.764 | 1.00 | 76.00 | O |
| ATOM | 321 | C2* | G | B | 16 | 6.392 | 15.750 | 28.201 | 1.00 | 59.82 | C |
| ATOM | 322 | C1* | G | B | 16 | 6.722 | 15.395 | 29.631 | 1.00 | 59.28 | C |
| ATOM | 323 | N9 | G | B | 16 | 6.813 | 16.618 | 30.456 | 1.00 | 54.53 | N |
| ATOM | 324 | C8 | G | B | 16 | 7.687 | 17.671 | 30.393 | 1.00 | 54.22 | C |
| ATOM | 325 | N7 | G | B | 16 | 7.459 | 18.589 | 31.299 | 1.00 | 47.73 | N |
| ATOM | 326 | C5 | G | B | 16 | 6.364 | 18.109 | 32.004 | 1.00 | 51.97 | C |
| ATOM | 327 | C6 | G | B | 16 | 5.641 | 18.642 | 33.102 | 1.00 | 55.57 | C |
| ATOM | 328 | O6 | G | B | 16 | 5.826 | 19.702 | 33.714 | 1.00 | 61.57 | O |
| ATOM | 329 | N1 | G | B | 16 | 4.593 | 17.815 | 33.502 | 1.00 | 54.46 | N |
| ATOM | 330 | C2 | G | B | 16 | 4.278 | 16.614 | 32.912 | 1.00 | 56.72 | C |
| ATOM | 331 | N2 | G | B | 16 | 3.235 | 15.940 | 33.420 | 1.00 | 63.09 | N |
| ATOM | 332 | N3 | G | B | 16 | 4.940 | 16.104 | 31.889 | 1.00 | 51.64 | N |
| ATOM | 333 | C4 | G | B | 16 | 5.957 | 16.893 | 31.491 | 1.00 | 50.12 | C |
| ATOM | 334 | P | G | B | 17 | 5.095 | 14.141 | 26.082 | 1.00 | 79.89 | P |

TABLE 2-continued

| | | | | | | | | | | | |
|---|---|---|---|---|---|---|---|---|---|---|---|
| ATOM | 335 | O1P | G | B | 17 | 4.667 | 12.944 | 25.300 | 1.00 | 86.80 | O |
| ATOM | 336 | O2P | G | B | 17 | 5.117 | 15.462 | 25.398 | 1.00 | 53.60 | O |
| ATOM | 337 | O5* | G | B | 17 | 4.092 | 14.257 | 27.323 | 1.00 | 86.50 | O |
| ATOM | 338 | C5* | G | B | 17 | 3.617 | 13.068 | 27.954 | 1.00 | 88.97 | C |
| ATOM | 339 | C4* | G | B | 17 | 2.153 | 13.177 | 28.283 | 1.00 | 89.63 | C |
| ATOM | 340 | O4* | G | B | 17 | 1.964 | 14.077 | 29.400 | 1.00 | 91.33 | O |
| ATOM | 341 | C3* | G | B | 17 | 1.250 | 13.731 | 27.176 | 1.00 | 87.59 | C |
| ATOM | 342 | O3* | G | B | 17 | −0.078 | 13.223 | 27.383 | 1.00 | 88.64 | O |
| ATOM | 343 | C2* | G | B | 17 | 1.268 | 15.226 | 27.453 | 1.00 | 83.36 | C |
| ATOM | 344 | C1* | G | B | 17 | 1.361 | 15.289 | 28.961 | 1.00 | 84.02 | C |
| ATOM | 345 | N9 | G | B | 17 | 2.129 | 16.475 | 29.396 | 1.00 | 71.28 | N |
| ATOM | 346 | C8 | G | B | 17 | 3.299 | 16.998 | 28.914 | 1.00 | 61.45 | C |
| ATOM | 347 | N7 | G | B | 17 | 3.671 | 18.066 | 29.566 | 1.00 | 66.87 | N |
| ATOM | 348 | C5 | G | B | 17 | 2.693 | 18.263 | 30.535 | 1.00 | 64.75 | C |
| ATOM | 349 | C6 | G | B | 17 | 2.548 | 19.256 | 31.539 | 1.00 | 59.98 | C |
| ATOM | 350 | O6 | G | B | 17 | 3.281 | 20.218 | 31.805 | 1.00 | 61.09 | O |
| ATOM | 351 | N1 | G | B | 17 | 1.398 | 19.060 | 32.299 | 1.00 | 57.16 | N |
| ATOM | 352 | C2 | G | B | 17 | 0.503 | 18.036 | 32.110 | 1.00 | 53.55 | C |
| ATOM | 353 | N2 | G | B | 17 | −0.550 | 18.001 | 32.933 | 1.00 | 50.77 | N |
| ATOM | 354 | N3 | G | B | 17 | 0.621 | 17.105 | 31.183 | 1.00 | 55.85 | N |
| ATOM | 355 | C4 | G | B | 17 | 1.732 | 17.281 | 30.439 | 1.00 | 64.36 | C |
| ATOM | 356 | P | +U | B | 18 | −0.802 | 12.350 | 26.237 | 1.00 | 75.01 | P |
| ATOM | 357 | O1P | +U | B | 18 | −1.906 | 11.566 | 26.857 | 1.00 | 97.23 | O |
| ATOM | 358 | O2P | +U | B | 18 | −1.123 | 13.230 | 25.074 | 1.00 | 63.36 | O |
| ATOM | 359 | O5* | +U | B | 18 | 0.333 | 11.331 | 25.776 | 0.00 | 39.48 | O |
| ATOM | 360 | C5* | +U | B | 18 | 0.038 | 9.935 | 25.731 | 0.00 | 39.48 | C |
| ATOM | 361 | C4* | +U | B | 18 | 0.834 | 9.299 | 24.616 | 0.00 | 39.48 | C |
| ATOM | 362 | O4* | +U | B | 18 | 2.070 | 10.012 | 24.429 | 0.00 | 39.48 | O |
| ATOM | 363 | C3* | +U | B | 18 | 1.207 | 7.847 | 24.848 | 0.00 | 39.48 | C |
| ATOM | 364 | O3* | +U | B | 18 | 0.694 | 6.935 | 23.891 | 0.00 | 39.48 | O |
| ATOM | 365 | C2* | +U | B | 18 | 2.702 | 7.781 | 24.886 | 0.00 | 39.48 | C |
| ATOM | 366 | C1* | +U | B | 18 | 3.037 | 9.026 | 24.102 | 0.00 | 39.48 | C |
| ATOM | 367 | N1 | +U | B | 18 | 4.395 | 9.573 | 24.231 | 0.00 | 39.48 | N |
| ATOM | 368 | C2 | +U | B | 18 | 5.049 | 9.750 | 23.022 | 0.00 | 39.48 | C |
| ATOM | 369 | O2 | +U | B | 18 | 4.532 | 9.468 | 21.967 | 0.00 | 39.48 | O |
| ATOM | 370 | N3 | +U | B | 18 | 6.281 | 10.250 | 23.176 | 0.00 | 39.48 | N |
| ATOM | 371 | C4 | +U | B | 18 | 6.916 | 10.588 | 24.359 | 0.00 | 39.48 | C |
| ATOM | 372 | O4 | +U | B | 18 | 8.053 | 11.038 | 24.304 | 0.00 | 39.48 | O |
| ATOM | 373 | C5 | +U | B | 18 | 6.182 | 10.387 | 25.584 | 0.00 | 39.48 | C |
| ATOM | 374 | C6 | +U | B | 18 | 4.944 | 9.882 | 25.449 | 0.00 | 39.48 | C |
| ATOM | 375 | P | T | B | 19 | −0.482 | 5.915 | 24.387 | 0.00 | 39.48 | P |
| ATOM | 376 | O1P | T | B | 19 | −1.068 | 5.268 | 23.182 | 0.00 | 39.48 | O |
| ATOM | 377 | O2P | T | B | 19 | −1.376 | 6.671 | 25.309 | 0.00 | 39.48 | O |
| ATOM | 378 | O5* | T | B | 19 | 0.262 | 4.799 | 25.236 | 0.00 | 39.48 | O |
| ATOM | 379 | C5* | T | B | 19 | −0.377 | 4.254 | 26.394 | 0.00 | 39.48 | C |
| ATOM | 380 | C4* | T | B | 19 | 0.637 | 3.500 | 27.219 | 0.00 | 39.48 | C |
| ATOM | 381 | O4* | T | B | 19 | 1.410 | 2.630 | 26.341 | 0.00 | 39.48 | O |
| ATOM | 382 | C3* | T | B | 19 | 1.701 | 4.394 | 27.883 | 0.00 | 39.48 | C |
| ATOM | 383 | O3* | T | B | 19 | 1.235 | 4.893 | 29.135 | 0.00 | 39.48 | O |
| ATOM | 384 | C2* | T | B | 19 | 2.818 | 3.376 | 28.081 | 0.00 | 39.48 | C |
| ATOM | 385 | C1* | T | B | 19 | 2.778 | 2.683 | 26.719 | 0.00 | 39.48 | C |
| ATOM | 386 | N1 | T | B | 19 | 3.627 | 3.305 | 25.697 | 0.00 | 39.48 | N |
| ATOM | 387 | C2 | T | B | 19 | 4.982 | 3.204 | 26.026 | 0.00 | 39.48 | C |
| ATOM | 388 | O2 | T | B | 19 | 5.327 | 2.659 | 27.035 | 0.00 | 39.48 | O |
| ATOM | 389 | N3 | T | B | 19 | 5.754 | 3.766 | 25.130 | 0.00 | 39.48 | N |
| ATOM | 390 | C4 | T | B | 19 | 5.416 | 4.398 | 23.941 | 0.00 | 39.48 | C |
| ATOM | 391 | O4 | T | B | 19 | 6.309 | 4.851 | 23.229 | 0.00 | 39.48 | O |
| ATOM | 392 | C5 | T | B | 19 | 4.007 | 4.479 | 23.648 | 0.00 | 39.48 | C |
| ATOM | 393 | C5M | T | B | 19 | 3.572 | 5.159 | 22.376 | 0.00 | 39.48 | C |
| ATOM | 394 | C6 | T | B | 19 | 3.183 | 3.914 | 24.565 | 0.00 | 39.48 | C |
| ATOM | 395 | P | A | B | 20 | 1.308 | 6.466 | 29.469 | 0.00 | 39.48 | P |
| ATOM | 396 | O1P | A | B | 20 | 0.459 | 6.764 | 30.654 | 0.00 | 39.48 | O |
| ATOM | 397 | O2P | A | B | 20 | 1.104 | 7.257 | 28.225 | 0.00 | 39.48 | O |
| ATOM | 398 | O5* | A | B | 20 | 2.838 | 6.641 | 29.902 | 0.00 | 39.48 | O |
| ATOM | 399 | C5* | A | B | 20 | 3.419 | 5.748 | 30.857 | 0.00 | 39.48 | C |
| ATOM | 400 | C4* | A | B | 20 | 4.707 | 6.363 | 31.379 | 0.00 | 39.48 | C |
| ATOM | 401 | O4* | A | B | 20 | 5.753 | 6.057 | 30.429 | 0.00 | 39.48 | O |
| ATOM | 402 | C3* | A | B | 20 | 4.632 | 7.891 | 31.445 | 0.00 | 39.48 | C |
| ATOM | 403 | O3* | A | B | 20 | 5.427 | 8.354 | 32.539 | 0.00 | 39.48 | O |
| ATOM | 404 | C2* | A | B | 20 | 5.183 | 8.322 | 30.108 | 0.00 | 39.48 | C |
| ATOM | 405 | C1* | A | B | 20 | 6.214 | 7.251 | 29.808 | 0.00 | 39.48 | C |
| ATOM | 406 | N9 | A | B | 20 | 6.377 | 7.089 | 28.348 | 0.00 | 39.48 | N |
| ATOM | 407 | C8 | A | B | 20 | 5.454 | 6.768 | 27.387 | 0.00 | 39.48 | C |
| ATOM | 408 | N7 | A | B | 20 | 5.959 | 6.711 | 26.177 | 0.00 | 39.48 | N |
| ATOM | 409 | C5 | A | B | 20 | 7.300 | 7.015 | 26.363 | 0.00 | 39.48 | C |
| ATOM | 410 | C6 | A | B | 20 | 8.381 | 7.121 | 25.474 | 0.00 | 39.48 | C |
| ATOM | 411 | N6 | A | B | 20 | 8.278 | 6.923 | 24.159 | 0.00 | 39.48 | N |
| ATOM | 412 | N1 | A | B | 20 | 9.584 | 7.442 | 26.001 | 0.00 | 39.48 | N |
| ATOM | 413 | C2 | A | B | 20 | 9.697 | 7.642 | 27.317 | 0.00 | 39.48 | C |

TABLE 2-continued

| | | | | | | | | | | | |
|---|---|---|---|---|---|---|---|---|---|---|---|
| ATOM | 414 | N3 | A | B | 20 | 8.752 | 7.571 | 28.254 | 0.00 | 39.48 | N |
| ATOM | 415 | C4 | A | B | 20 | 7.574 | 7.251 | 27.698 | 0.00 | 39.48 | C |
| ATOM | 416 | P | G | B | 21 | 4.636 | 8.623 | 33.925 | 1.00 | 82.34 | P |
| ATOM | 417 | O1P | G | B | 21 | 5.546 | 8.375 | 35.076 | 1.00 | 109.71 | O |
| ATOM | 418 | O2P | G | B | 21 | 3.335 | 7.897 | 33.895 | 1.00 | 93.38 | O |
| ATOM | 419 | O5* | G | B | 21 | 4.332 | 10.188 | 33.840 | 1.00 | 83.27 | O |
| ATOM | 420 | C5* | G | B | 21 | 2.997 | 10.684 | 33.918 | 1.00 | 81.10 | C |
| ATOM | 421 | C4* | G | B | 21 | 2.520 | 10.711 | 35.350 | 1.00 | 74.34 | C |
| ATOM | 422 | O4* | G | B | 21 | 3.616 | 11.024 | 36.234 | 1.00 | 75.57 | O |
| ATOM | 423 | C3* | G | B | 21 | 1.408 | 11.702 | 35.655 | 1.00 | 69.75 | C |
| ATOM | 424 | O3* | G | B | 21 | 0.242 | 10.989 | 36.088 | 1.00 | 67.91 | O |
| ATOM | 425 | C2* | G | B | 21 | 1.914 | 12.576 | 36.772 | 1.00 | 70.80 | C |
| ATOM | 426 | C1* | G | B | 21 | 3.366 | 12.224 | 36.936 | 1.00 | 68.38 | C |
| ATOM | 427 | N9 | G | B | 21 | 4.242 | 13.338 | 36.528 | 1.00 | 58.81 | N |
| ATOM | 428 | C8 | G | B | 21 | 5.258 | 13.382 | 35.609 | 1.00 | 52.20 | C |
| ATOM | 429 | N7 | G | B | 21 | 5.817 | 14.560 | 35.515 | 1.00 | 48.15 | N |
| ATOM | 430 | C5 | G | B | 21 | 5.121 | 15.340 | 36.432 | 1.00 | 53.76 | C |
| ATOM | 431 | C6 | G | B | 21 | 5.265 | 16.707 | 36.786 | 1.00 | 51.12 | C |
| ATOM | 432 | O6 | G | B | 21 | 6.076 | 17.515 | 36.328 | 1.00 | 50.74 | O |
| ATOM | 433 | N1 | G | B | 21 | 4.356 | 17.100 | 37.762 | 1.00 | 53.13 | N |
| ATOM | 434 | C2 | G | B | 21 | 3.417 | 16.268 | 38.328 | 1.00 | 55.33 | C |
| ATOM | 435 | N2 | G | B | 21 | 2.616 | 16.805 | 39.256 | 1.00 | 39.97 | N |
| ATOM | 436 | N3 | G | B | 21 | 3.268 | 14.994 | 38.012 | 1.00 | 55.10 | N |
| ATOM | 437 | C4 | G | B | 21 | 4.147 | 14.602 | 37.065 | 1.00 | 54.88 | C |
| ATOM | 438 | P | G | B | 22 | −1.192 | 11.474 | 35.535 | 1.00 | 72.19 | P |
| ATOM | 439 | O1P | G | B | 22 | −2.227 | 10.531 | 36.042 | 1.00 | 72.91 | O |
| ATOM | 440 | O2P | G | B | 22 | −1.102 | 11.722 | 34.067 | 1.00 | 70.22 | O |
| ATOM | 441 | O5* | G | B | 22 | −1.427 | 12.903 | 36.217 | 1.00 | 67.49 | O |
| ATOM | 442 | C5* | G | B | 22 | −1.288 | 13.056 | 37.625 | 1.00 | 64.02 | C |
| ATOM | 443 | C4* | G | B | 22 | −2.015 | 14.256 | 38.150 | 1.00 | 61.74 | C |
| ATOM | 444 | O4* | G | B | 22 | −1.093 | 15.342 | 38.397 | 1.00 | 58.52 | O |
| ATOM | 445 | C3* | G | B | 22 | −3.121 | 14.854 | 37.283 | 1.00 | 61.49 | C |
| ATOM | 446 | O3* | G | B | 22 | −4.097 | 15.455 | 38.154 | 1.00 | 70.14 | O |
| ATOM | 447 | C2* | G | B | 22 | −2.399 | 15.950 | 36.521 | 1.00 | 59.65 | C |
| ATOM | 448 | C1* | G | B | 22 | −1.345 | 16.419 | 37.501 | 1.00 | 58.00 | C |
| ATOM | 449 | N9 | G | B | 22 | −0.114 | 16.830 | 36.789 | 1.00 | 54.08 | N |
| ATOM | 450 | C8 | G | B | 22 | 0.627 | 16.132 | 35.861 | 1.00 | 52.13 | C |
| ATOM | 451 | N7 | G | B | 22 | 1.660 | 16.800 | 35.434 | 1.00 | 50.04 | N |
| ATOM | 452 | C5 | G | B | 22 | 1.596 | 18.009 | 36.121 | 1.00 | 55.19 | C |
| ATOM | 453 | C6 | G | B | 22 | 2.453 | 19.139 | 36.070 | 1.00 | 50.39 | C |
| ATOM | 454 | O6 | G | B | 22 | 3.470 | 19.277 | 35.375 | 1.00 | 51.75 | O |
| ATOM | 455 | N1 | G | B | 22 | 2.032 | 20.153 | 36.924 | 1.00 | 43.28 | N |
| ATOM | 456 | C2 | G | B | 22 | 0.921 | 20.089 | 37.729 | 1.00 | 45.35 | C |
| ATOM | 457 | N2 | G | B | 22 | 0.673 | 21.168 | 38.486 | 1.00 | 41.81 | N |
| ATOM | 458 | N3 | G | B | 22 | 0.113 | 19.044 | 37.786 | 1.00 | 51.13 | N |
| ATOM | 459 | C4 | G | B | 22 | 0.501 | 18.042 | 36.965 | 1.00 | 53.95 | C |
| ATOM | 460 | P | G | B | 23 | −5.530 | 15.862 | 37.530 | 1.00 | 71.41 | P |
| ATOM | 461 | O1P | G | B | 23 | −6.598 | 15.463 | 38.487 | 1.00 | 80.85 | O |
| ATOM | 462 | O2P | G | B | 23 | −5.592 | 15.377 | 36.126 | 1.00 | 54.14 | O |
| ATOM | 463 | O5* | G | B | 23 | −5.502 | 17.463 | 37.512 | 1.00 | 66.09 | O |
| ATOM | 464 | C5* | G | B | 23 | −4.730 | 18.127 | 38.506 | 1.00 | 70.38 | C |
| ATOM | 465 | C4* | G | B | 23 | −5.115 | 19.562 | 38.686 | 1.00 | 73.91 | C |
| ATOM | 466 | O4* | G | B | 23 | −3.977 | 20.425 | 38.430 | 1.00 | 69.72 | O |
| ATOM | 467 | C3* | G | B | 23 | −6.217 | 20.137 | 37.785 | 1.00 | 70.57 | C |
| ATOM | 468 | O3* | G | B | 23 | −6.682 | 21.340 | 38.426 | 1.00 | 73.25 | O |
| ATOM | 469 | C2* | G | B | 23 | −5.412 | 20.526 | 36.550 | 1.00 | 64.87 | C |
| ATOM | 470 | C1* | G | B | 23 | −4.118 | 21.039 | 37.153 | 1.00 | 64.29 | C |
| ATOM | 471 | N9 | G | B | 23 | −2.973 | 20.715 | 36.273 | 1.00 | 57.79 | N |
| ATOM | 472 | C8 | G | B | 23 | −2.756 | 19.608 | 35.493 | 1.00 | 60.11 | C |
| ATOM | 473 | N7 | G | B | 23 | −1.624 | 19.663 | 34.845 | 1.00 | 61.51 | N |
| ATOM | 474 | C5 | G | B | 23 | −1.065 | 20.877 | 35.222 | 1.00 | 59.84 | C |
| ATOM | 475 | C6 | G | B | 23 | 0.165 | 21.477 | 34.835 | 1.00 | 50.33 | C |
| ATOM | 476 | O6 | G | B | 23 | 1.013 | 21.023 | 34.058 | 1.00 | 45.98 | O |
| ATOM | 477 | N1 | G | B | 23 | 0.346 | 22.710 | 35.451 | 1.00 | 44.69 | N |
| ATOM | 478 | C2 | G | B | 23 | −0.551 | 23.279 | 36.324 | 1.00 | 46.78 | C |
| ATOM | 479 | N2 | G | B | 23 | −0.204 | 24.473 | 36.817 | 1.00 | 44.01 | N |
| ATOM | 480 | N3 | G | B | 23 | −1.703 | 22.737 | 36.698 | 1.00 | 47.00 | N |
| ATOM | 481 | C4 | G | B | 23 | −1.891 | 21.539 | 36.107 | 1.00 | 55.06 | C |
| ATOM | 482 | P | T | B | 24 | −8.128 | 21.961 | 38.114 | 1.00 | 73.74 | P |
| ATOM | 483 | O1P | T | B | 24 | −8.746 | 22.436 | 39.387 | 1.00 | 52.86 | O |
| ATOM | 484 | O2P | T | B | 24 | −8.880 | 21.026 | 37.234 | 1.00 | 46.81 | O |
| ATOM | 485 | O5* | T | B | 24 | −7.802 | 23.272 | 37.253 | 1.00 | 77.25 | O |
| ATOM | 486 | C5* | T | B | 24 | −6.750 | 24.137 | 37.687 | 1.00 | 85.78 | C |
| ATOM | 487 | C4* | T | B | 24 | −6.374 | 25.095 | 36.589 | 1.00 | 88.60 | C |
| ATOM | 488 | O4* | T | B | 24 | −5.152 | 24.663 | 35.940 | 1.00 | 85.23 | O |
| ATOM | 489 | C3* | T | B | 24 | −7.410 | 25.284 | 35.485 | 1.00 | 87.84 | C |
| ATOM | 490 | O3* | T | B | 24 | −7.620 | 26.674 | 35.222 | 1.00 | 76.52 | O |
| ATOM | 491 | C2* | T | B | 24 | −6.800 | 24.574 | 34.290 | 1.00 | 82.67 | C |
| ATOM | 492 | C1* | T | B | 24 | −5.316 | 24.791 | 34.531 | 1.00 | 78.81 | C |

TABLE 2-continued

| | | | | | | | | | | | |
|---|---|---|---|---|---|---|---|---|---|---|---|
| ATOM | 493 | N1 | T | B | 24 | −4.404 | 23.880 | 33.815 | 1.00 | 67.59 | N |
| ATOM | 494 | C2 | T | B | 24 | −3.103 | 24.313 | 33.672 | 1.00 | 57.03 | C |
| ATOM | 495 | O2 | T | B | 24 | −2.726 | 25.389 | 34.113 | 1.00 | 55.18 | O |
| ATOM | 496 | N3 | T | B | 24 | −2.290 | 23.438 | 33.001 | 1.00 | 45.17 | N |
| ATOM | 497 | C4 | T | B | 24 | −2.623 | 22.210 | 32.472 | 1.00 | 50.99 | C |
| ATOM | 498 | O4 | T | B | 24 | −1.772 | 21.533 | 31.891 | 1.00 | 54.38 | O |
| ATOM | 499 | C5 | T | B | 24 | −4.003 | 21.825 | 32.661 | 1.00 | 56.41 | C |
| ATOM | 500 | C5M | T | B | 24 | −4.449 | 20.504 | 32.115 | 1.00 | 56.99 | C |
| ATOM | 501 | C6 | T | B | 24 | −4.814 | 22.671 | 33.316 | 1.00 | 62.36 | C |
| TER | 502 | | T | B | 24 | | | | | | |
| HETATM | 503 | BR | BRO | B | 13 | 13.009 | 21.025 | 42.499 | 1.00 | 19.10 | BR |
| HETATM | 504 | BR | BRO | B | 18 | 6.991 | 10.824 | 27.226 | 0.00 | 39.48 | BR |
| HETATM | 505 | K | K | | 25 | 3.714 | 21.764 | 33.996 | 1.00 | 43.74 | K |
| HETATM | 506 | K | K | | 26 | 5.964 | 20.373 | 36.261 | 1.00 | 42.15 | K |
| HETATM | 507 | NA | NA | | 27 | 0.295 | 36.246 | 45.907 | 1.00 | 62.13 | NA |
| HETATM | 508 | O | HOH | | 2001 | 7.887 | 28.235 | 41.708 | 1.00 | 45.10 | O |
| HETATM | 509 | O | HOH | | 2002 | 6.482 | 29.211 | 35.302 | 1.00 | 53.48 | O |
| HETATM | 510 | O | HOH | | 2003 | 6.461 | 33.641 | 39.454 | 1.00 | 44.32 | O |
| HETATM | 511 | O | HOH | | 2004 | 13.380 | 25.172 | 36.896 | 1.00 | 44.21 | O |
| HETATM | 512 | O | HOH | | 2005 | 13.358 | 23.802 | 33.146 | 1.00 | 44.20 | O |
| HETATM | 513 | O | HOH | | 2006 | −1.980 | 21.350 | 40.062 | 1.00 | 54.69 | O |
| HETATM | 514 | O | HOH | | 2007 | 8.226 | 31.736 | 38.909 | 1.00 | 55.42 | O |
| HETATM | 515 | O | HOH | | 2008 | 7.774 | 28.642 | 28.627 | 1.00 | 39.66 | O |
| HETATM | 516 | O | HOH | | 2009 | −1.098 | 18.618 | 41.342 | 1.00 | 57.91 | O |
| HETATM | 517 | O | HOH | | 2010 | −0.552 | 33.274 | 46.254 | 1.00 | 51.38 | O |
| HETATM | 518 | O | HOH | | 2011 | 17.166 | 23.891 | 31.031 | 1.00 | 58.75 | O |
| HETATM | 519 | O | HOH | | 2012 | −0.615 | 26.954 | 34.209 | 1.00 | 50.96 | O |
| HETATM | 520 | O | HOH | | 2013 | 6.039 | 26.880 | 42.514 | 1.00 | 49.34 | O |
| HETATM | 521 | O | HOH | | 2014 | −8.336 | 21.572 | 35.075 | 1.00 | 60.27 | O |
| HETATM | 522 | O | HOH | | 2015 | 4.415 | 28.264 | 44.052 | 1.00 | 49.22 | O |
| HETATM | 523 | O | HOH | | 2016 | 1.131 | 40.396 | 40.615 | 1.00 | 46.82 | O |
| HETATM | 524 | O | HOH | | 2017 | −1.579 | 28.659 | 36.612 | 1.00 | 49.01 | O |
| HETATM | 525 | O | HOH | | 2018 | 3.519 | 7.578 | 36.163 | 1.00 | 59.59 | O |
| HETATM | 526 | O | HOH | | 2019 | 4.349 | 20.948 | 45.910 | 0.50 | 43.23 | O |
| HETATM | 527 | O | HOH | | 2020 | 7.043 | 29.041 | 31.805 | 1.00 | 51.58 | O |
| HETATM | 528 | O | HOH | | 2021 | −5.076 | 17.402 | 34.878 | 1.00 | 59.36 | O |
| HETATM | 529 | O | HOH | | 2022 | −3.463 | 28.391 | 40.841 | 1.00 | 57.89 | O |
| HETATM | 530 | O | HOH | | 2023 | 0.866 | 32.175 | 48.236 | 0.50 | 43.30 | O |
| HETATM | 531 | O | HOH | | 2024 | 12.465 | 16.504 | 42.911 | 1.00 | 51.13 | O |
| HETATM | 532 | O | HOH | | 2025 | −2.111 | 16.072 | 31.399 | 0.50 | 52.42 | O |
| HETATM | 533 | O | HOH | | 2026 | 6.358 | 37.510 | 37.221 | 1.00 | 54.58 | O |
| HETATM | 534 | O | HOH | | 2027 | 12.809 | 22.217 | 30.653 | 0.50 | 38.21 | O |
| HETATM | 535 | O | HOH | | 2028 | 15.058 | 15.438 | 32.787 | 0.50 | 36.25 | O |
| HETATM | 536 | O | HOH | | 2029 | 8.158 | 28.892 | 39.525 | 1.00 | 56.54 | O |
| HETATM | 537 | O | HOH | | 2030 | 10.518 | 14.183 | 32.051 | 1.00 | 52.85 | O |
| HETATM | 538 | O | HOH | | 2031 | −3.663 | 29.537 | 35.671 | 1.00 | 57.28 | O |
| HETATM | 539 | O | HOH | | 2032 | 0.294 | 15.795 | 40.495 | 1.00 | 69.10 | O |
| HETATM | 540 | O | HOH | | 2033 | −5.135 | 27.848 | 36.419 | 1.00 | 57.53 | O |
| HETATM | 541 | O | HOH | | 2034 | 1.890 | 13.085 | 39.524 | 1.00 | 54.99 | O |
| HETATM | 542 | O | HOH | | 2035 | 0.942 | 28.780 | 46.202 | 1.00 | 56.51 | O |
| HETATM | 543 | O | HOH | | 2036 | 6.865 | 27.447 | 45.381 | 1.00 | 58.67 | O |
| HETATM | 544 | O | HOH | | 2037 | −0.297 | 34.131 | 39.438 | 1.  00 | 55.19 | O |
| HETATM | 545 | O | HOH | | 2038 | 3.469 | 39.335 | 36.716 | 1.00 | 64.80 | O |
| HETATM | 546 | O | HOH | | 2039 | 3.901 | 35.485 | 30.001 | 0.50 | 51.39 | O |
| HETATM | 547 | O | HOH | | 2040 | 10.583 | 33.364 | 38.150 | 1.00 | 56.14 | O |
| HETATM | 548 | O | HOH | | 2041 | −4.392 | 10.891 | 25.149 | 1.00 | 71.31 | O |
| HETATM | 549 | O | HOH | | 2042 | 6.159 | 28.805 | 37.828 | 1.00 | 60.90 | O |
| HETATM | 550 | O | HOH | | 2043 | 0.016 | 26.327 | 46.714 | 1.00 | 63.94 | O |
| HETATM | 551 | O | HOH | | 2044 | 5.670 | 13.282 | 31.137 | 0.50 | 48.51 | O |
| HETATM | 552 | O | HOH | | 2045 | 17.533 | 17.630 | 35.756 | 1.00 | 66.52 | O |
| HETATM | 553 | O | HOH | | 2046 | −1.368 | 25.249 | 39.280 | 0.50 | 52.20 | O |
| HETATM | 554 | O | HOH | | 2047 | −2.533 | 13.674 | 44.574 | 0.50 | 58.50 | O |
| HETATM | 555 | O | HOH | | 2048 | −1.167 | 12.708 | 29.683 | 1.00 | 69.54 | O |
| HETATM | 556 | O | HOH | | 2049 | 14.771 | 28.329 | 39.359 | 1.00 | 78.99 | O |
| HETATM | 557 | O | HOH | | 2050 | 0.320 | 7.526 | 33.497 | 1.00 | 79.96 | O |
| CONECT | 15 | 251 | | | | | | | | | |
| CONECT | 121 | 252 | | | | | | | | | |
| CONECT | 251 | 15 | | | | | | | | | |
| CONECT | 252 | 121 | | | | | | | | | |
| C0NECT | 267 | 503 | | | | | | | | | |
| CONECT | 373 | 504 | | | | | | | | | |
| CONECT | 503 | 267 | | | | | | | | | |
| CONECT | 504 | 373 | | | | | | | | | |
| MASTER | 220 | 0 | 7 | 0 | 0 | 0 | 0 | 6 | 555 | 2 | 8 | 2 |
| END | | | | | | | | | | | |

The invention claimed is:

1. A crystal of a G-quadruplex of SEQ ID NO:1 and BRACO19 having the space group P6 and the unit cell dimensions of a=b=56.7 Å and c=42.1 Å and α=β=90° and γ=120°.

2. A method for producing a crystal of claim 1 comprising crystallizing a G-quadruplex of SEQ ID NO:1 by the hanging drop method at 285° K in a solution of 300 mM KI, 15% v/v PEG 400, 1.7 mM DNA, 2 mM BRACO19, and 50 mM potassium cacodylate at pH 6.5.

* * * * *